US012753221B2

(12) United States Patent
Yao et al.

(10) Patent No.: US 12,753,221 B2
(45) Date of Patent: *Oct. 6, 2026

(54) COMBINED CHIMERIC ANTIGEN RECEPTOR TARGETING CD19 AND CD20 AND APPLICATION THEREOF

(71) Applicant: AbelZeta, Inc., Rockville, MD (US)

(72) Inventors: Yihong Yao, Rockville, MD (US); Yanfeng Li, Shanghai (CN); Yutian Wei, Shanghai (CN); Shigui Zhu, Rockville, MD (US); Xin Yao, Rockville, MD (US); Jiaqi Huang, Rockville, MD (US)

(73) Assignee: AbelZeta Inc., Rockville, MD (US)

( * ) Notice: Subject to any disclaimer, the term of this patent is extended or adjusted under 35 U.S.C. 154(b) by 808 days.

This patent is subject to a terminal disclaimer.

(21) Appl. No.: 18/183,681

(22) Filed: Mar. 14, 2023

(65) Prior Publication Data

US 2024/0139243 A1 May 2, 2024

Related U.S. Application Data

(63) Continuation of application No. 17/750,658, filed on May 23, 2022, now Pat. No. 11,633,430, which is a continuation of application No. 17/475,766, filed on Sep. 15, 2021, now Pat. No. 11,439,665, which is a continuation of application No. 16/877,069, filed on May 18, 2020, now Pat. No. 11,207,349.

(30) Foreign Application Priority Data

Mar. 17, 2020 (CN) ........................ 202010188038.1

(51) Int. Cl.

| | |
|---|---|
| ***C07K 14/705*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***A61P 35/02*** | (2006.01) |
| ***C07K 14/47*** | (2006.01) |
| ***C07K 16/28*** | (2006.01) |
| ***C12N 5/0783*** | (2010.01) |

(52) U.S. Cl.

CPC ........ *C07K 14/70596* (2013.01); *A61K 40/11* (2025.01); *A61K 40/31* (2025.01); *A61K 40/4211* (2025.01); *A61K 40/4221* (2025.01); *A61P 35/00* (2018.01); *C12N 5/0636* (2013.01); *A61K 2239/29* (2023.05)

(58) Field of Classification Search

None

See application file for complete search history.

(56) References Cited

U.S. PATENT DOCUMENTS

| | | | |
|---|---|---|---|
| 6,074,841 | A † | 6/2000 | Gearing |
| 6,410,319 | B1 | 6/2002 | Raubitschek et al. |
| 7,446,179 | B2 | 11/2008 | Jensen et al. |
| 7,446,190 | B2 | 11/2008 | Sadelain et al. |
| 7,462,352 | B2 | 12/2008 | Hansen et al. |
| 8,287,864 | B2 | 10/2012 | Goldenberg et al. |
| 8,329,181 | B2 | 12/2012 | Martin et al. |
| 8,389,282 | B2 | 3/2013 | Sadelain et al. |
| 8,399,645 | B2 | 3/2013 | Campana et al. |
| 8,529,902 | B2 † | 9/2013 | Teeling |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,328,156 | B2 | 5/2016 | June et al. |
| 9,447,194 | B2 | 9/2016 | Jensen |
| 9,464,140 | B2 | 10/2016 | June et al. |

(Continued)

FOREIGN PATENT DOCUMENTS

| | | |
|---|---|---|
| CN | 101544694 A | 9/2009 |
| CN | 106279434 A | 1/2017 |

(Continued)

OTHER PUBLICATIONS

US 11,419,896 B2, 08/2022, Yao et al. (withdrawn)

Zhu et al, "Closed-system manufacturing of CD19 and dual-targeted CD20/19 chimeric antigen receptor T cells using the CliniMACS Prodigy device at an academic medical center", Cytotherapy, 2018, vol. 20, pp. 394-406.

(Continued)

*Primary Examiner* — Ilia I Ouspenski

(74) *Attorney, Agent, or Firm* — LEASON ELLIS LLP

(57) ABSTRACT

The present invention provides a combined chimeric antigen receptor targeting CD19 and CD20 and application thereof. Specifically, the present invention provides a combined chimeric antigen receptor targeting CD19 and CD20, which comprises a scFv targeting CD19 and CD20, a hinge region, a transmembrane region, and an intracellular signaling domain. The present invention provides a nucleic acid molecule encoding the chimeric antigen receptor and a corresponding expression vector, a CAR-T cell, and applications thereof. The experimental results show that the chimeric antigen receptor provided by the present invention shows extremely high killing ability against tumor cells. The chimeric antigen receptor of the present invention targets CD19 and/or CD20 positive cells and can be used to treat CD19 and/or CD20 positive B-cell lymphoma, leukemia and other diseases.

18 Claims, 19 Drawing Sheets

Specification includes a Sequence Listing.

(56) References Cited

U.S. PATENT DOCUMENTS

| | | | |
|---|---|---|---|
| 9,481,728 | B2 | 11/2016 | June et al. |
| 9,499,629 | B2 | 11/2016 | June et al. |
| 9,518,123 | B2 | 12/2016 | June et al. |
| 9,540,445 | B2 | 1/2017 | June et al. |
| 9,605,049 | B2 | 3/2017 | Campana et al. |
| 9,662,354 | B2 | 5/2017 | Hyde et al. |
| 9,834,590 | B2 | 12/2017 | Campana et al. |
| 9,856,322 | B2 | 1/2018 | Campana et al. |
| 9,919,061 | B2 | 3/2018 | Mcdonagh et al. |
| 10,040,827 | B2 | 8/2018 | Delecluse et al. |
| 10,189,903 | B2 | 1/2019 | Jensen |
| 10,221,245 | B2 | 3/2019 | Brogdon et al. |
| 10,287,350 | B2 | 5/2019 | Kochenderfer |
| 10,442,867 | B2 | 10/2019 | Orentas et al. |
| 10,457,730 | B2 | 10/2019 | Puléet al. |
| 10,493,139 | B2 | 12/2019 | Wu et al. |
| 10,501,539 | B2 | 12/2019 | Schneider et al. |
| 10,507,219 | B2 | 12/2019 | Gilbert |
| 10,525,083 | B2 | 1/2020 | Brannetti et al. |
| 10,533,055 | B2 | 1/2020 | Chen et al. |
| 10,603,380 | B2 | 3/2020 | Wilzius |
| 10,639,329 | B2 | 5/2020 | Dropulic et al. |
| 10,736,918 | B2 | 8/2020 | Jensen et al. |
| 11,026,976 | B2 | 6/2021 | Brannetti et al. |
| 11,066,457 | B2 | 7/2021 | Yao et al. |
| 11,207,349 | B2 | 12/2021 | Yao et al. |
| 11,439,665 | B2 | 9/2022 | Yao et al. |
| 11,472,858 | B2 | 10/2022 | Yao et al. |
| 11,608,369 | B2 | 3/2023 | Yao et al. |
| 11,618,778 | B2 | 4/2023 | Yao et al. |
| 11,633,430 | B2 | 4/2023 | Yao et al. |
| 11,890,300 | B2 | 2/2024 | Lock et al. |
| 11,890,301 | B2 | 2/2024 | June et al. |
| 12,053,491 | B2 | 8/2024 | Chen et al. |
| 12,448,432 | B2 * | 10/2025 | Yao .................... C07K 14/7051 |
| 12,458,667 | B2 | 11/2025 | Yao et al. |
| 2004/0167319 | A1 | 8/2004 | Teeling |
| 2009/0148447 | A1 | 6/2009 | Ledbetter |
| 2011/0091473 | A1 | 4/2011 | Golab |
| 2013/0004480 | A1 | 1/2013 | Parren |
| 2013/0224205 | A1 | 8/2013 | Hofmeister |
| 2014/0093454 | A1 | 4/2014 | Teeling et al. |
| 2014/0154253 | A1 | 6/2014 | Ng |
| 2015/0038684 | A1 | 2/2015 | Jensen |
| 2015/0306141 | A1 | 10/2015 | Jensen et al. |
| 2016/0145337 | A1 | 5/2016 | Galetto et al. |
| 2016/0152723 | A1 | 6/2016 | Chen et al. |
| 2016/0158359 | A1 | 6/2016 | Gilbert |
| 2016/0333108 | A1 | 11/2016 | Forman |
| 2016/0362472 | A1 | 12/2016 | Bitter |
| 2017/0073664 | A1 | 3/2017 | Mccafferty et al. |
| 2017/0267756 | A1 | 9/2017 | Riddell et al. |
| 2017/0275382 | A1 | 9/2017 | Poma |
| 2017/0355767 | A1 | 12/2017 | Engelberts et al. |
| 2017/0368098 | A1 † | 12/2017 | Chen |
| 2018/0044415 | A1 | 2/2018 | Escarpe |
| 2018/0044417 | A1 | 2/2018 | Puléet al. |
| 2018/0085401 | A1 | 3/2018 | Wu et al. |
| 2018/0118823 | A1 | 5/2018 | Thompson |
| 2018/0125892 | A1 | 5/2018 | Brannetti et al. |
| 2018/0142034 | A1 | 5/2018 | Chang |
| 2018/0142035 | A1 | 5/2018 | Lobb |
| 2018/0153977 | A1 | 6/2018 | Wu et al. |
| 2018/0230225 | A1 | 8/2018 | Fan et al. |
| 2018/0243341 | A1 | 8/2018 | June et al. |
| 2018/0258391 | A1 | 9/2018 | June et al. |
| 2018/0265585 | A1 | 9/2018 | Kong |
| 2018/0312588 | A1 | 11/2018 | Wilzius et al. |
| 2018/0319862 | A1 | 11/2018 | Thompson et al. |
| 2018/0355052 | A1 | 12/2018 | Orentas et al. |
| 2018/0355318 | A1 | 12/2018 | Delaney et al. |
| 2019/0106501 | A1 | 4/2019 | Press |
| 2019/0107537 | A1 | 4/2019 | Chaudhary |
| 2019/0112380 | A1 | 4/2019 | Chaudhary |
| 2019/0119382 | A1 | 4/2019 | Jensen |
| 2019/0135940 | A1 | 5/2019 | Brogdon et al. |
| 2019/0144515 | A1 | 5/2019 | Sievers et al. |
| 2019/0169289 | A1 | 6/2019 | Young et al. |
| 2019/0321404 | A1 | 10/2019 | Fan et al. |
| 2020/0002400 | A1 | 1/2020 | Yao et al. |
| 2020/0040096 | A1 | 2/2020 | Forman et al. |
| 2020/0078405 | A1 | 3/2020 | Jensen et al. |
| 2020/0093861 | A1 | 3/2020 | Klein et al. |
| 2020/0109210 | A1 | 4/2020 | Orentas et al. |
| 2020/0215108 | A1 | 7/2020 | Jensen |
| 2020/0216534 | A1 | 7/2020 | Davila |
| 2020/0246382 | A1 | 8/2020 | Perez et al. |
| 2020/0289517 | A1 | 9/2020 | He |
| 2020/0306375 | A1 | 10/2020 | Lobb et al. |
| 2020/0308223 | A1 | 10/2020 | Chang |
| 2021/0079111 | A1 | 3/2021 | Zhang et al. |
| 2021/0290673 | A1 | 9/2021 | Yao |
| 2021/0363245 | A1 | 11/2021 | Kochenderfer et al. |
| 2021/0388100 | A1 | 12/2021 | Satpayev et al. |
| 2022/0249568 | A1 | 8/2022 | Yao et al. |
| 2022/0281945 | A1 | 9/2022 | Yao et al. |
| 2022/0340640 | A1 | 10/2022 | Yao et al. |
| 2023/0036065 | A1 | 2/2023 | McCreedy, Jr. et al. |
| 2023/0104705 | A1 | 4/2023 | Yao et al. |
| 2023/0212255 | A1 | 7/2023 | Yao et al. |
| 2023/0242613 | A1 | 8/2023 | Yao et al. |
| 2024/0034802 | A1 | 2/2024 | Orentas et al. |
| 2024/0115605 | A1 | 4/2024 | Yao et al. |
| 2025/0144144 | A1 | 5/2025 | Chen et al. |
| 2025/0262243 | A1 | 8/2025 | Yao et al. |

FOREIGN PATENT DOCUMENTS

| | | | |
|---|---|---|---|
| CN | 107868791 | A | 4/2018 |
| CN | 107936120 | A | 4/2018 |
| CN | 108017717 | A | 5/2018 |
| CN | 108285486 | A | 7/2018 |
| CN | 108395482 | A | 8/2018 |
| CN | 108472346 | A | 8/2018 |
| CN | 108715616 | A | 10/2018 |
| CN | 109423495 | A | 3/2019 |
| CN | 109536455 | A | 3/2019 |
| CN | 109575143 | A | 4/2019 |
| CN | 110062768 | A | 7/2019 |
| CN | 110606893 | A | 12/2019 |
| CN | 110845623 | A | 2/2020 |
| CN | 112390891 | A | 2/2021 |
| CN | 112608387 | A | 4/2021 |
| EP | 3989986 | A1 | 5/2022 |
| JP | 2015-092865 | A | 5/2015 |
| JP | 2018-508215 | A | 3/2018 |
| WO | 2000/023573 | A2 | 4/2000 |
| WO | 2012/079000 | A1 | 6/2012 |
| WO | 2013/123061 | A1 | 8/2013 |
| WO | 2014/012085 | A2 | 1/2014 |
| WO | 2016/014576 | A1 | 1/2016 |
| WO | 2016/097231 | A2 | 6/2016 |
| WO | 2016/100232 | A1 | 6/2016 |
| WO | 2016/120216 | A1 | 8/2016 |
| WO | 2016/126608 | A1 | 8/2016 |
| WO | 2016/139487 | A1 | 9/2016 |
| WO | 2016/164731 | A2 | 10/2016 |
| WO | 2016/166521 | A1 | 10/2016 |
| WO | 2016/179319 | A1 | 11/2016 |
| WO | 2016/201394 | A1 | 12/2016 |
| WO | 2017/025038 | A1 | 2/2017 |
| WO | 2017/149515 | A1 | 9/2017 |
| WO | 2018/067992 | A1 | 4/2018 |
| WO | 2018/068766 | A1 | 4/2018 |
| WO | 2018/121604 | A1 | 7/2018 |
| WO | 2018/145649 | A1 | 8/2018 |
| WO | 2019/028051 | A1 | 2/2019 |
| WO | 2019/075395 | A1 | 4/2019 |
| WO | 2019/126724 | A1 | 6/2019 |
| WO | 2019/128952 | A1 | 7/2019 |
| WO | 2019/129177 | A1 | 7/2019 |
| WO | 2019/154313 | A1 | 8/2019 |
| WO | 2019/178576 | A1 | 9/2019 |
| WO | 2019/206326 | A1 | 10/2019 |

(56) References Cited

FOREIGN PATENT DOCUMENTS

| | | | |
|---|---|---|---|
| WO | 2019/210153 | A1 | 10/2019 |
| WO | 2019/223226 | A1 | 11/2019 |
| WO | 2019/232444 | A1 | 12/2019 |
| WO | 2020/010235 | A1 | 1/2020 |
| WO | 2020/033273 | A1 | 2/2020 |
| WO | 2020/061796 | A1 | 4/2020 |
| WO | 2020072536 | A1 | 4/2020 |
| WO | 2020/151752 | A1 | 7/2020 |
| WO | 2020/210665 | A1 | 10/2020 |
| WO | 2021/188681 | A1 | 9/2021 |

OTHER PUBLICATIONS

International Search Report and Written Opinion in PCT/CN2020/109645, mailed on Dec. 16, 2020.

GenBank Accession No. AMZ04821, bi-specific chimeric antigen receptor 20-19 Short, partial [synthetic construct]. Apr. 24, 2016 [online]. [Retrieved on Jul. 22, 2021]. Retrieved from the internet: URL: https://www.ncbi.nlm.nih.gov/protein/AMZ04821.

International Search Report and Written Opinion in PCT/US21/22779, mailed on Aug. 9, 2021.

Chavez et al., CAR T-cell therapy for B-cell lymphomas: clinical trial results of available products, Ther. Adv. Hematol. 2019, vol. 10: 1-20.

Zah et al., T cells expressing CD19/CD20 bi-specific chimeric antigen receptors prevent antigen escape by malignant B cells, Cancer Immunol. Res. 2016, 4(6): 498-508.

Makita et al. "Clinical development of anti-CD19 chimeric antigen receptor T-cell therapy for B-cell non-Hodgkin lymphoma" Cancer Sci (2017) 108: 1109-1118.

Martyniszyn et al. "CD20-CD19 Bispecific CART Cells for the Treatment of B-Cell Malignancies" Human Gene Therapy (2017) vol. 28, No. 12, pp. 1147-1157.

Wang et al. "Effective response and delayed toxicities of refractory advanced diffuse large B-cell lymphoma treated by CD20-directed chimeric antigen receptor-modified T cells" Clinical Immunology (2014) 155, 160-175.

Watanabe et al. "Target Antigen Density Governs the Efficacy of Anti-CD20-CD28-CD3z Chimeric Antigen Receptor-Modified Effector CD8+ T Cells" J Immunol 2015; 194: 911-920.

Zah et al. "Addendum: T cells expressing CD19/CD20 bi-specific chimeric antigen receptors prevent antigen escape by malignant B cells" Cancer Immunology Research (2016) vol. 4, No. 7, pp. 639-641.

Zhou et al. "The efficacy and safety of anti-CD19/CD20chimeric antigen receptor T cells immunotherapy in relapsed or refractory B-cell malignancies: a meta-analysis"BMC Cancer (2018) 18:929.

Buehler et al, "Influence of Structural Variations on Biological Activity of Anti-PSMA scFv and Immunotoxins Targeting Prostate Cancer", Anticancer Research, 30: 3373-3380 (2010).

Kim et al, "Improving the Productivity of Single-Chain Fv Antibody Against c-Met by Rearranging the Order of its Variable Domains", J. Microbiol. Biotechnol. (2008), 18(6), 1186-1190.

Kipriyanov et al, "Effect of Domain Order on the Activity of Bacterially Produced Bispecific Single-chain Fv Antibodies": J. Mol. Biol. (2003) 330, 99-111.

Schneider et al: "A tandem CD19/CD20 CAR lentiviral vector drives on-target and off-target antigen modulation in leukemia cell lines", Journal for Immunotherapy of Cancer, vol. 5, No. 1, 2017, pp. 1-17.

Chuan et al: Optimized tandem CD19/CD20 CAR-engineered T cells in refractory/relapsed B cell lymphoma', BLOOD, 2020, 136(14):1632-1644.

Liang et al: "Safety and efficacy of a novel anti-CD20/CD19 bi-specific CAR T-cell therapy (C-CAR039) in relapsed or refractory (r/r) B-cell non-Hodgkin lymphoma (B-NHL).", Journal of Clinical Oncology, vol. 39, No. 15_suppl, 2021, pp. 2507-2507.

Jayaraman et al., CAR-T design: Elements and their synergistic function. EBioMedicine. Aug. 2020; 58:102931, 12 pages.

ClinicalTrials.gov, NCT03019055, Study of CAR-20/19-T Cells in Patients With Relapsed Refractory B Cell. 15 pages, Jul. 27, 2023.

Li et al., Clinical Responses and Pharmacokinetics of fully human BCMA Targeting Car T Cell Therapy in Relapsed/Refractory Multiple Myeloma. 17th International Myeloma Workshop. pp. e23-e24, Abstract 0AB-033, Sep. 12-15, 2019.

Raje et al., Anti-BCMA CAR T-Cell Therapy bb2121 in Relapsed or Refractory Multiple Myeloma. N Engl J Med. May 2, 2019;380(18):1726-1737.

Belovezhec, Design and Comparative Analysis of CD20-Specific Chimeric Antigen Receptors. Proceedings of XIV International Conference of Students, Graduate Students and Young Scientists. Perspectives in Fundamental Sciences. Biology and Basic Medical Sciences, vol. 4, pp. 22-24, Apr. 25-28, 2017.

Budde et al., Combining a CD20 chimeric antigen receptor and an inducible caspase 9 suicide switch to improve the efficacy and safety of T cell adoptive immunotherapy for lymphoma. PLoS One. Dec. 17, 2013;8(12):e82742, 10 pages.

Cao et al., Efficiency and safety of autologous chimeric antigen receptor T-cells therapy used for patients with lymphoma: A systematic review and meta-analysis. Medicine (Baltimore). Oct. 2019; 98(42):e17506, 8 pages.

Casan et al., Anti-CD20 monoclonal antibodies: reviewing a revolution. Hum Vaccin Immunother. 2018;14(12):2820-2841.

Chow et al., Outcomes of patients with large B-cell lymphomas and progressive disease following CD19-specific CAR T-cell therapy. Am J Hematol. Aug. 2019;94(8):E209-E213.

Chuda et al., Ofatumumab: A Novel Anti-CD20 Monoclonal Antibody for the Treatment of Chronic Lymphocytic Leukemia. Current Drug Therapy. 2012;7:281-289.

Dondelinger et al., Understanding the Significance and Implications of Antibody Numbering and Antigen-Binding Surface/Residue Definition. Front Immunol. Oct. 16, 2018;9:2278, 15 pages.

Fesnak et al., Engineered T cells: the promise and challenges of cancer immunotherapy. Nat Rev Cancer. Aug. 23, 2016;16(9):566-81.

GenBank Accession No. AA022134, mh79f12.r1 Soares mouse placenta 4NbMP13.5 14.5 Mus musculus cDNA clone IMAGE:457199 5' similar to SW:YBC6_YEAST P38203 Hypothetical 11.2 KD Protein in RPL19-MCM2 Intergenic Region. [2] PIR:S45760, mRNA sequence. 3 pages, Jan. 21, 1997.

GenBank Accession No. AKH40187, C2B8, partial [synthetic construct]. 7 pages, Jul. 28, 2015.

GenBank Accession No. AMZ04820, bi-specific chimeric antigen receptor 20-19 Long, partial [synthetic construct]. 10 pages, Apr. 24, 2016.

GenBank Accession No. ANS59202, Dsg3 EC1-3 CAAR [synthetic construct]. 2 pages, Jul. 19, 2016.

Ghafouri et al., CD19/CD20 bispecific chimeric antigen receptor (CAR) in naive/memory T-cells for the treatment of relapsed or refractory B-cell lymphomas. Jul. 1, 2021;81(13):Abstract CT007.

Hallek, Chronic lymphocytic leukemia: 2017 update on diagnosis, risk stratification, and treatment. Am J Hematol. Sep. 2017;92(9):946-965.

Hamdy et al., Sheep red blood cells armed with anti-CD20 single-chain variable fragments (scFvs) fused to a glycosylphosphatidylinositol (GPI) anchor: a strategy to target CD20-positive tumor cells. J Immunol Methods. Feb. 2005;297(1-2):109-24.

Jabbour et al., Monoclonal antibodies in acute lymphoblastic leukemia. Blood. Jun. 25, 2015;125(26):4010-6.

Jensen et al., CD20 is a molecular target for scFvFc:zeta receptor redirected T cells: implications for cellular immunotherapy of CD20+ malignancy. Biol Blood Marrow Transplant. 1998;4(2):75-83.

Jonnalagadda et al., Chimeric antigen receptors with mutated IgG4 Fc spacer avoid fc receptor binding and improve T cell persistence and antitumor efficacy. Mol Ther. Apr. 2015;23(4):757-68.

Korycka-Wolowiec et al., Ofatumumab for treating chronic lymphocytic leukemia: a safety profile. Expert Opin Drug Saf. 2015;14(12):1945-59.

Ku et al., Tumour cell surface antigen targeted therapies in B-cell lymphomas: Beyond rituximab. Blood Rev. Jan. 2017;31(1):23-35.

(56) References Cited

OTHER PUBLICATIONS

Kunik et al., Structural consensus among antibodies defines the antigen binding site. PLoS Comput Biol. 2012;8(2):e1002388.
Kussie et al., A single engineered amino acid substitution changes antibody fine specificity. J Immunol. Jan. 1, 1994;152(1):146-52.
Lin, Ofatumumab: a novel monoclonal anti-CD20 antibody. Pharmgenomics Pers Med. 2010;3:51-9.
Liu et al., Fine mapping of the antigen-antibody interaction of scFv215, a recombinant antibody inhibiting RNA polymerase II from *Drosophila melanogaster*. J Mol Recognit. Mar.-Apr. 1999;12(2):103-11.
Lopez-Atalyaya et al., Development and maintenance of the brain's immune toolkit: Microglia and non-parenchymal brain macrophages. Dev Neurobiol. Jun. 2018;78(6):561-579.
Lulla et al., The use of chimeric antigen receptor T cells in patients with non-Hodgkin lymphoma. Clin Adv Hematol Oncol. May 2018;16(5):375-386.
Nakagawa et al., *Staphylococcus aureus* Virulent PSMa Peptides Induce Keratinocyte Alarmin Release to Orchestrate IL-17-Dependent Skin Inflammation. Cell Host Microbe. Nov. 8, 2017;22(5):667-677.
Panka et al., Variable region framework differences result in decreased or increased affinity of variant anti-digoxin antibodies. Proc Natl Acad Sci U S A. May 1988;85(9):3080-4.
Patel et al., Expanding the Role of CAR-T Cell Therapy to Systemic Lupus Erythematosus. EMJ Hematol. 2020;8(1):105-112.
Ramos et al., CAR-T Cell Therapy for Lymphoma. Annu Rev Med. 2016;67:165-83.
Riaz et al., Anti-CD 19 and anti-CD 20 CAR-modified T cells for B-cell malignancies: a systematic review and meta-analysis. Immunotherapy. Sep. 2017;9(12):979-993.
Rudikoff et al., Single amino acid substitution altering antigen-binding specificity. Proc Natl Acad Sci U S A. Mar. 1982;79(6):1979-83.
Rufener et al., Preserved Activity of CD20-Specific Chimeric Antigen Receptor-Expressing T Cells in the Presence of Rituximab. Cancer Immunol Res. Jun. 2016;4(6):509-19.
Sela-Culang et al., The structural basis of antibody-antigen recognition. Front Immunol. Oct. 8, 2013;4:302.
Shah et al., Bispecific anti-CD20, anti-CD19 CAR T cells for relapsed B cell malignancies: a phase 1 dose escalation and expansion trial. Nat Med. Oct. 2020;26(10):1569-1575.
Shetty et al., Liver sinusoidal endothelial cells—gatekeepers of hepatic immunity. Nat Rev Gastroenterol Hepatol. Sep. 2018;15(9):555-567.
Teeling et al., Characterization of new human CD20 monoclonal antibodies with potent cytolytic activity against non-Hodgkin lymphomas. Blood. Sep. 15, 2004;104(6):1793-800.
Teeling et al., The biological activity of human CD20 monoclonal antibodies is linked to unique epitopes on CD20. J Immunol. Jul. 1, 2006;177(1):362-71.
Till et al., Adoptive immunotherapy for indolent non-Hodgkin lymphoma and mantle cell lymphoma using genetically modified autologous CD20-specific T cells. Blood. Sep. 15, 2008;112(6):2261-71.
Till et al., CD20-specific adoptive immunotherapy for lymphoma using a chimeric antigen receptor with both CD28 and 4-1BB domains: pilot clinical trial results. Blood. Apr. 26, 2012;119(17):3940-50.
Wark et al., Latest technologies for the enhancement of antibody affinity. Adv Drug Deliv Rev. Aug. 7, 2006;58(5-6):657-70.
Wong et al., Structural requirements for a specificity switch and for maintenance of affinity using mutational analysis of a phage-displayed anti-arsonate antibody of Fab heavy chain first complementarity-determining region. J Immunol. Jun. 15, 1998;160(12):5990-7.
Wu et al., Multimerization of a chimeric anti-CD20 single-chain Fv-Fc fusion protein is mediated through variable domain exchange. Protein Eng. Dec. 2001;14(12):1025-33.
Zhang et al., Treatment of CD20-directed Chimeric Antigen Receptor-modified T cells in patients with relapsed or refractory B-cell non-Hodgkin lymphoma: an early phase lla trial report. Signal Transduct Target Ther. Mar. 11, 2016;1:16002, 9 pages.
European Office Action for Application No. 18751050.8, dated Oct. 15, 2020, 14 pages.
International Search Report and Written Opinion for Application No. PCT/CN2018/075867, dated May 9, 2018, 14 pages.
International Search Report and Written Opinion for Application No. PCT/US2022/013875, dated Jul. 8, 2022, 10 pages.
Dudek et al., Mitochondrial protein import: common principles and physiological networks. Biochim Biophys Acta. Feb. 2013;1833(2):274-85.
Edwards et al., The remarkable flexibility of the human antibody repertoire; isolation of over one thousand different antibodies to a single protein, BLyS. J Mol Biol. Nov. 14, 2003;334(1):103-18.
Goel et al., Plasticity within the antigen-combining site may manifest as molecular mimicry in the humoral immune response. J Immunol. Dec. 15, 2004;173(12):7358-67.
Guedan et al., Engineering and Design of Chimeric Antigen Receptors. Mol Ther Methods Clin Dev. Mar. 15, 2019;12:145-156.
Kosugi et al., Six classes of nuclear localization signals specific to different binding grooves of importin alpha. J Biol Chem. Jan. 2, 2009;284(1):478-485.
Sadelain et al., The basic principles of chimeric antigen receptor design. Cancer Discov. Apr. 2013;3(4):388-98.
U.S. Appl. No. 17/475,766, filed Sep. 15, 2021, U.S. Pat. No. 11,439,665.
U.S. Appl. No. 17/721,647, filed Apr. 15, 2022, 2022-0249568.
U.S. Appl. No. 17/750,658, filed May 23, 2022, U.S. Pat. No. 11,633,430.
U.S. Appl. No. 17/911,502, filed Sep. 14, 2022, 2023-0104705.
U.S. Appl. No. 17/911,524, filed Sep. 14, 2022, 2023-0212255.
U.S. Appl. No. 16/877,069, filed May 18, 2020, U.S. Pat. No. 11,207,349.
U.S. Appl. No. 16/484,482, filed Aug. 8, 2019, U.S. Pat. No. 11,066,457.
U.S. Appl. No. 17/352,915, filed Jun. 21, 2021, U.S. Pat. No. 11,472,858.
U.S. Appl. No. 17/723,859, filed Apr. 19, 2022, U.S. Pat. No. 11,618,778.
U.S. Appl. No. 17/750,855, filed May 23, 2022, U.S. Pat. No. 11,608,369.
U.S. Appl. No. 17/831,637, filed Jun. 3, 2022, 2022-0340640.
U.S. Appl. No. 18/173,187, filed Feb. 23, 2023, 2023-0242613.
U.S. Appl. No. 18/263,050, filed Jul. 26, 2023, 2024-0115605.
Zah, Eugenia, et al. "T Cells Expressing CD19/CD20 Bispecific Chimeric Antigen Receptors Prevent Antigen Escape by Malignant B Cells," (2016) Cancer Immunol. Res: 4(6):498-508.†
Du, Jiamu, et al. "Structure of the Fab fragment of therapeutic antibody Ofatumumab provides insights into the recognition mechanism with CD20," (2009) Molecular Immunology 46:2419-2423.†
GenBank Accession No. KX000911, Nucleotide—NCBI, https://www.ncbi.nlm.nih.gov/nuccore/KX000911, retrieved on Sep. 4, 2023, 2 pages, Pub. Date: Apr. 24, 2016.†

* cited by examiner
† cited by third party

COMBINED CHIMERIC ANTIGEN RECEPTOR TARGETING CD19 AND CD20 AND APPLICATION THEREOF

INCORPORATION-BY-REFERENCE OF SEQUENCE LISTING

A sequence listing, filed as the XML file "CMP—Sequence Listing-11299_008882-US7.XML" which was created on Mar. 14, 2023 and is 82,722 bytes in size, is incorporated herein by reference in its entirety.

TECHNICAL FIELD

The present invention relates to the field of bio-medicine, and more particularly to a combined chimeric antigen receptor targeting CD19 and CD20 and application thereof.

BACKGROUND

Malignant tumors of the blood system account for about 10% of human malignant tumors, and 95% of malignant tumors of the blood system are derived from B lymphocytes. Traditional chemotherapy and radiotherapy play an important role in the treatment of malignant tumors of the blood system. Some patients have significant effects, but it is difficult for most of the patients to be cured. New and effective treatments have been a hot topic in this field.

Adoptive T cell therapy has shown its powerful efficacy and bright prospect in the clinical treatment of malignant tumors. At present, it is regarded as one of the most promising methods for treating hematological tumors. CD19 is highly expressed on the surface of most B-cell malignancies.

Multiple centers independently using Chimeric Antigen Receptor (CAR)-modified T cells to target recurrent, refractory malignant tumors of CD19-expressed B cell have achieved unprecedented success. At present, both of the two CAR-T products approved by FDA are targeting CD19 antigen and their indications are also expanding, such as chronic lymphocytic leukemia. Although the efficacy of anti-CD19 CAR-T is outstanding, many studies have shown that there are also many problems with CD19 chimeric antigen receptor (CAR) T cell therapy. There are still some patients with poor treatment results and easy to relapse. The reasons for this include the susceptibility of tumor cells to antigen escape. For example, a recent experiment of CD19 CAR-cell therapy showed that 90% of patients achieved complete remission, but 11% of these patients eventually relapsed, and the relapsing patients were mainly patients with CD19-negative tumor. In particular, in a clinical trial carried out at the University of Pennsylvania School of Medicine using CART19 in the treatment of recurrent, refractory acute B-cell lymphoma (R/R B-ALL), up to 94% of patients achieved complete remission. Although the initial response rate of this clinical trial was high, nearly 40% of patients relapsed after 1 month of treatment which achieved complete remission, and more than 60% of relapsing patients had CD19-negative tumor cells escape. Antigen escape has been found in adoptive transfer specific T cell receptors expressing NY-ESO1 and cancer vaccines treating melanoma. Spontaneous mutation and selective expansion are the main reasons for antigen escape.

Therefore, there is an urgent need in the art to develop methods for effectively treating tumors and preventing antigen escape.

SUMMARY OF THE INVENTION

An object of the present invention is to provide a method for effectively treating tumors and preventing antigen escape.

An object of the present invention is to provide a combined chimeric antigen receptor targeting CD19 and CD20 and preparation method thereof.

Specifically, it is an object of the present invention to provide a sequence of the combined chimeric antigen receptor targeting CD19 and CD20 as well as a preparation method and activity identification of the modified T cell (CART-19/20) thereof. The present invention provides a chimeric antigen receptor structure for use in the treatment of CD19 and CD20 positive B cell lymphoma.

In a first aspect of the invention, it provides a chimeric antigen receptor (CAR), wherein the structure of the chimeric antigen receptor is shown in formula I as below:

$$\text{L-scFv1-I-scFv2-H-TM-C-CD3}\xi \quad \text{(I)}$$

wherein, each "—" is independently a linker peptide or a peptide bond;

L is an optional signal peptide sequence;

I is a flexible linker;

H is an optional hinge region;

TM is a transmembrane domain;

C is a co-stimulatory signaling molecule;

CD3ξ is a cytoplasmic signaling sequence derived from CD3ξ;

one of scFv1 and scFv2 is an antigen binding domain targeting CD19, and the other is an antigen binding domain targeting CD20.

In another preferred embodiment, the scFv1 is an antigen binding domain targeting CD20, and the scFv2 is an antigen binding domain targeting CD19.

In another preferred embodiment, the structure of the antigen binding domain targeting CD20 is shown in formula A or B as below:

$$V_{H1}—V_{L1} \quad \text{(A);}$$

$$V_{L1}—V_{H1} \quad \text{(B)}$$

wherein $V_{H1}$ is an anti-CD20 antibody heavy chain variable region; $V_{L1}$ is an anti-CD20 antibody light chain variable region; and "—" is a linker peptide or a peptide bond.

In another preferred embodiment, the structure of the antigen binding domain targeting CD20 is shown in formula B.

In another preferred embodiment, the amino acid sequence of the $V_{H1}$ is shown in SEQ ID NO 1, and the amino acid sequence of the $V_{L1}$ is shown in SEQ ID NO 2; or the amino acid sequence of the $V_H1$ is shown in SEQ ID NO 3, and the amino acid sequence of the $V_{L1}$ is shown in SEQ ID NO 4.

In another preferred embodiment, the $V_H1$ and $V_{L1}$ are linked with a flexible linker (or a linker peptide), and the flexible linker (or the linker peptide) is 1-4, preferably 2-4, more preferably 3-4 consecutive sequences as shown in SEQ ID NO 7 (GGGGS).

In another preferred embodiment, the structure of the antigen binding domain targeting CD19 is shown in formula C or D as below:

$$V_{L2}—V_{H2} \quad \text{(C);}$$

$$V_{H2}—V_{L2} \quad \text{(D)}$$

wherein $V_{L2}$ is an anti-CD19 antibody light chain variable region; $V_{H2}$ is an anti-CD19 antibody heavy chain variable region; and "—" is a linker peptide or a peptide bond.

In another preferred embodiment, the structure of the antigen binding domain targeting CD19 is shown in formula D.

In another preferred embodiment, the amino acid sequence of the $V_{L2}$ is shown in SEQ ID NO 5, and the amino acid sequence of the $V_{H2}$ is shown in SEQ ID NO 6.

In another preferred embodiment, the $V_{H2}$ and $V_{L2}$ are linked with a flexible linker (or a linker peptide), and the flexible linker (or the linker peptide) is 1-4, preferably 2-4, more preferably 3-4 consecutive sequence as shown in SEQ ID NO 7 (GGGGS).

In another preferred embodiment, the scFv1 and/or scFv2 are mouse-derived, humanized, humanized and mouse-derived chimeric, or fully humanized single chain antibody variable region fragments.

In another preferred embodiment, the structure of the chimeric antigen receptor is shown in formula II as below:

$$L\text{-}V_{L1}\text{-}V_{H1}\text{-}I\text{-}V_{H2}\text{-}V_{L2}\text{-}H\text{-}TM\text{-}C\text{-}CD3\xi \qquad (II)$$

wherein each element is as described above.

In another preferred embodiment, the sequence of the flexible linker I comprises 2-6, preferably 3-4 consecutive sequences as shown in SEQ ID NO 7 (GGGGS).

In another preferred embodiment, the L is a signal peptide of a protein selected from the group consisting of CD8, CD28, GM-CSF, CD4, CD137, and a combination thereof.

In another preferred embodiment, the L is a signal peptide derived from CD8.

In another preferred embodiment, the amino acid sequence of the L is shown in SEQ ID NO 8.

In another preferred embodiment, the H is a hinge region of a protein selected from the group consisting of CD8, CD28, CD137, Ig4, and a combination thereof.

In another preferred embodiment, the H is a hinge region derived from Ig4.

In another preferred embodiment, the amino acid sequence of the H is shown in SEQ ID NO 9.

In another preferred embodiment, the TM is a transmembrane region of a protein selected from the group consisting of CD28, CD3ε, CD45, CD4, CD5, CD8, CD9, CD16, CD22, CD33, CD37, CD64, CD80, CD86, CD134, CD137, CD154, and a combination thereof.

In another preferred embodiment, the TM is a transmembrane region derived from CD8 or CD28.

In another preferred embodiment, the sequence of the TM is shown in SEQ ID NO 10 or 11.

In another preferred embodiment, the C is a co-stimulatory signaling molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, and a combination thereof.

In another preferred embodiment, the C is a co-stimulatory signaling molecule derived from 4-1BB or CD28.

In another preferred embodiment, the amino acid sequence of the C is shown in SEQ ID NO 12 or 13.

In another preferred embodiment, the amino acid sequence of the CD3ξ is shown in SEQ ID NO 14.

In another preferred embodiment, the amino acid sequence of the CAR is shown in SEQ ID NO 15 or 16.

In a second aspect of the invention, it provides a nucleic acid molecule, encoding the chimeric antigen receptor of the first aspect of the invention.

In another preferred embodiment, the nucleic acid molecule is isolated.

In another preferred embodiment, the nucleotide sequence of the nucleic acid molecule is shown in SEQ ID NO 17 or 18.

In a third aspect of the invention, it provides a vector, comprising the nucleic acid molecule of the second aspect of the invention.

In another preferred embodiment, the vector comprises DNA and RNA.

In another preferred embodiment, the vector is selected from the group consisting of plasmid, virus vector, transposon, and a combination thereof.

In another preferred embodiment, the vector comprises a DNA virus and a retrovirus vector.

In another preferred embodiment, the vector is selected from the group consisting of a lentiviral vector, an adenovirus vector, an adeno-associated virus vector, and a combination thereof.

In another preferred embodiment, the vector is a lentiviral vector.

In a fourth aspect of the invention, it provides a host cell, comprising the vector of the third aspect of the invention or having the exogenous nucleic acid molecule of the second aspect of the invention integrated into its genome or expressing the chimeric antigen receptor of the first aspect of the invention.

In another preferred embodiment, the cell is an isolated cell.

In another preferred embodiment, the cell is a genetically engineered cell.

In another preferred embodiment, the cell is a mammalian cell.

In another preferred embodiment, the cell is a CAR-T cell and/or a CAR-NK cell.

In another preferred embodiment, the cell targets both CD19 and CD20.

In a fifth aspect of the invention, it provides a method for preparing a CAR-T cell expressing the chimeric antigen receptor of the first aspect of the invention, wherein the method comprises the steps of: transducing the nucleic acid molecule of the second aspect of the invention or the vector of the third aspect of the invention into a T cell, thereby obtaining the CAR-T cell.

In another preferred embodiment, the method further comprises the step of detecting the function and effectiveness of the obtained CAR-T cell.

In a sixth aspect of the invention, it provides a preparation, comprising the chimeric antigen receptor of the first aspect of the invention, the nucleic acid molecule of the second aspect of the invention, the vector of the third aspect of the invention, or the host cell of the fourth aspect of the invention, and a pharmaceutically acceptable carrier, diluent or excipient.

In another preferred embodiment, the preparation is a liquid preparation.

In another preferred embodiment, the formulation of the preparation is an injection.

In another preferred embodiment, the preparation comprises the host cell of the fourth aspect of the invention, and the concentration of the host cell is $1\times10^3$-$1\times10^8$ cells/ml, preferably $1\times10^4$-$1\times10^7$ cells/ml.

In a seventh aspect of the invention, it provides the use of the chimeric antigen receptor of the first aspect of the invention, the nucleic acid molecule of the second aspect of the invention, the vector of the third aspect of the invention, or the host cell of the fourth aspect of the invention, for the preparation of a medicine or a formulation for preventing and/or treating tumor or cancer.

In another preferred embodiment, the tumor is selected from the group consisting of a hematological tumor, a solid tumor, and a combination thereof, preferably, the tumor is a hematological tumor.

In another preferred embodiment, the blood tumor is selected from the group consisting of acute myeloid leukemia (AML), multiple myeloma (MM), chronic lymphocytic leukemia (CLL), acute lymphoblastic leukemia (ALL), diffuse large B cell lymphoma (DLBCL), and a combination thereof.

In another preferred embodiment, the solid tumor is selected from the group consisting of gastric cancer, peritoneal metastasis of gastric cancer, liver cancer, leukemia, renal cancer, lung cancer, small intestine cancer, bone cancer, prostate cancer, colorectal cancer, breast cancer, large intestine cancer, cervical cancer, ovarian cancer, lymphoma, nasopharyngeal carcinoma, adrenal tumor, bladder tumor, non-small cell lung cancer (NSCLC), glioma, endometrial cancer, and a combination thereof.

In an eighth aspect of the invention, it provides a kit for the preparation of the cell of the fourth aspect of the invention, wherein the kit comprises a container, and the nucleic acid molecule of the second aspect of the invention or the vector of the third aspect of the invention located in the container.

In a ninth aspect of the invention, it provides a use of the cell of the fourth aspect of the invention, or the formulation of the sixth aspect of the invention for the prevention and/or treatment of cancer or tumor.

In a tenth aspect of the invention, it provides a method of treating a disease comprising administering an appropriate amount of the cell of the forth aspect of the invention, or the formulation of the sixth aspect of the invention, to a subject in need of treatment.

In another preferred embodiment, the disease is cancer or tumor.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DESCRIPTION OF DRAWINGS

FIG. 6A shows the detection of the transfection efficiency of CAR-T19/20s cells. Protein L method was used to identify the expression level of CAR gene-encoded protein on the surface of T cell membrane in CAR-T19/20s cells cultured 9 days. $1\times10^5$ CAR-T19/20s cells cultured 10 days (FIG. 6B) and 18 days (FIG. 6C) were taken and cultured respectively with CD19-positive K562-CD19+ tumor cell line, CD20-positive K562-CD20+ tumor cell line, CD19 and CD20 double positive K562-CD19+CD20+ tumor cell line, RAJI or RAMOS tumor cell line that naturally expresses CD19 and CD20, and CD19 and CD20 double negative K562 or MOLT4 tumor cell line, or without tumor cells, in 200 μl of GT-551 medium for 18 h with a ratio of 1:1. Then the expression level of CD137 on the surface of T cell membrane was detected respectively. FIG. 6D shows the secretion level of IFNγ in the culture supernatant.

FIG. 6E shows the average body weight changes and average fluorescence intensity changes of mice injected with CAR-T19/20s cells within 21 days, which are recorded every 7 days. FIG. 6F shows in vivo imaging of mice injected with CAR-T19/20s cells on day 0 (DO), 7 (D7), 14 (D14), and 21 (D21) after injection.

FIG. 7A shows the testing results of the transfection efficiency of T cells. The expression level of CAR gene-encoded protein on the surface of T cell membrane in CAR-T20s cells cultured 7 days was identified by the DNA copy number detection method. FIG. 7B shows the secretion level of IFNγ in the supernatant of CAR-T20s cells co-cultured with target cells. FIG. 7C shows the expression level of CD137 on the surface of T cell membranes after co-culture.

FIG. 8A shows the testing results of the transfection efficiency of T cells. The expression level of the CAR gene-encoded protein on the surface of the T cell membrane in CAR-T20s cells cultured 7 days was identified by the Protein L method. FIG. 8B shows the secretion level of IFNγ in the supernatant of CAR-T20s cells co-cultured with target cells. FIG. 8C shows the expression level of CD137 on the surface of T cell membranes after co-culture.

FIG. 9A shows the testing results of the transfection efficiency of T cells. The expression level of the CAR gene-encoded protein on the surface of the T cell membrane in CAR-T20s cells cultured 7 days was identified by the Protein L method. FIG. 9B shows the secretion level of IFNγ in the supernatant of CAR-T20s cells co-cultured with target cells. FIG. 9C shows the expression level of CD137 on the surface of T cell membranes after co-culture.

FIG. 10A shows the detection results of T cell transfection efficiency. FIG. 10B shows the IFNγ secretion level in the supernatant after co-culture. FIG. 10C shows the detection of tumor cell killing ability of CAR-T20s cells, mainly by detecting the secretion level of LDH in the supernatant after co-culture. FIG. 10D shows the expression level of CD137 on the surface of T cell membranes.

Figure 1:
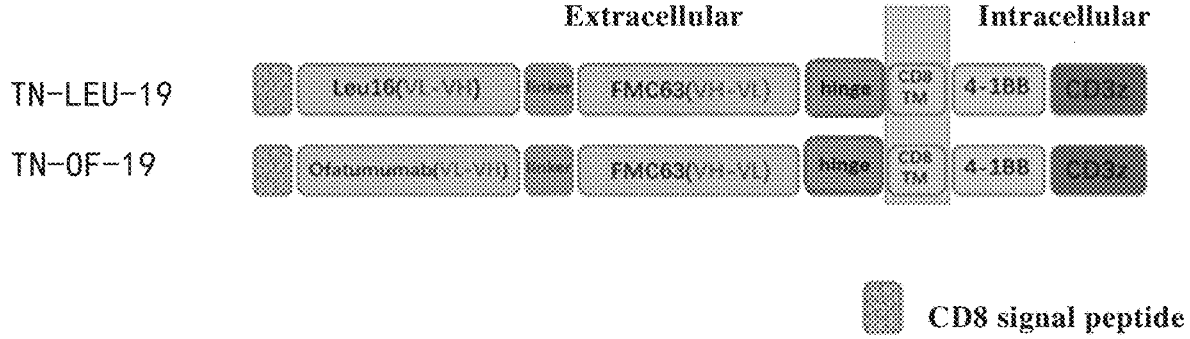
FIG. 1 shows structure of the combined chimeric antigen receptor targeting CD19 and CD20. The structure of the CAR comprises a leader sequence, an antigen recognition sequence, a hinge region, a transmembrane region, a co-stimulatory factor signal region, and a CD3ξ signaling region.

In the figures, TN-OF-19 and TN-200F-19 have the same meaning, and TN-LEU-19 and TN-20 LEU-19 have the same meaning, both indicating CART cells having the corresponding CAR structure.

MODES FOR CARRYING OUT THE PRESENT INVENTION

After extensive and intensive studies, the inventors unexpectedly obtained a CAR-T cell that simultaneously targets CD19 and CD20. Specifically, the present invention provides a chimeric antigen receptor that simultaneously targets CD19 and CD20, which comprises a signal peptide, an anti-CD20 scFv, an anti-CD19 scFv, a hinge region, a transmembrane region, and an intracellular T cell signaling region. Moreover, the anti-CD20 scFv and anti-CD19 scFv were obtained through a large number of screenings, which were linked with peptide fragment with multiple repeat structure (G4S). The CAR-T cells of the present invention can recognize both CD19 and CD20 antigens at the same time, reducing the risk of immune escape caused by down-regulation or deletion of antigen expression during the treatment of single-target CAR-T cells. Compared to CAR-T cells targeting single antigens and other double target CAR-T cells (targeting CD19 and CD20), the CAR-T cells of the present invention that simultaneously recognize two targets have stronger killing ability against tumor cells, less cytotoxicity, lower side effects, wider treatment range, lower recurrence rate and better efficacy. The present invention has been completed on the basis of this.

Terms

To make the disclosure easier to understand, some terms are firstly defined. As used in this application, unless expressly stated otherwise herein, each of the following terms shall have the meanings given below. Other definitions are set forth throughout the application.

The term "about" may refer to a value or composition within an acceptable error range for a particular value or composition as determined by those skilled in the art, which will depend in part on how the value or composition is measured or determined.

The term "administering" refers to the physical introduction of a product of the invention into a subject using any one of various methods and delivery systems known to those skilled in the art, including intravenous, intramuscular, subcutaneous, intraperitoneal, spinal or other parenteral administration, such as by injection or infusion.

The term "antibody" (Ab) may comprise, but is not limited to, an immunoglobulin that specifically binds an antigen and contains at least two heavy (H) chains and two light (L) chains linked by disulfide bonds, or an antigen binding parts thereof. Each H chain contains a heavy chain variable region (abbreviated herein as VH) and a heavy chain constant region. The heavy chain constant region contains three constant domains, CH1, CH2, and CH3. Each light chain contains a light chain variable region (abbreviated herein as VL) and a light chain constant region. The light chain constant region contains a constant domain CL. The VH and VL regions can be further subdivided into hypervariable regions called complementarity determining regions (CDR), which are interspersed within more conservative regions called framework regions (FR). Each VH and VL contains three CDRs and four FRs, which are arranged from amino terminal to carboxy terminal in the following order: FR1, CDR1, FR2, CDR2, FR3, CDR3, and FR4. The variable regions of the heavy and light chains contain a binding domain that interacts with an antigen.

CD20

Although the efficacy of anti-CD19 CAR-T is outstanding, many studies have shown that there are still many problems with CD19 chimeric antigen receptor (CAR) T cell therapy. There are still some patients with poor treatment results and easy to relapse. This includes the susceptibility of tumor cells to antigen escape.

In order to prevent the escape of CD19 CAR-T antigen, the inventors designs a combined bispecific CAR (ie, BICAR) that targets both CD19 and CD20, so that when CD19 antigen escapes and is not expressed in tumor cells, CD20 can be recognized to clear tumor cells in vivo.

CD20 is expressed in most patients with B-cell acute lymphoblastic leukemia, including some CD19 negative patients after anti-CD19 CAR-T treatment. CD20 is a glycosylated protein, and is the first identified B cell membrane marker. CD20 is also known as B1, and encoded by the MS4A gene. CD20 molecule has four transmembrane hydrophobic regions, and its N-terminal and C-terminal are located on the cytoplasmic side, forming two closed loops outside the cell, and respectively called big loop and small loop. CD20 is specifically expressed in more than 95% of normal and cancerous B cells. These cells are in the pre-B cell stage and subsequent developmental stages, and CD20 stops expression until the cells differentiated into plasma cells. The present invention uses CD20 as another target for immunotherapy of B cell malignancies.

Bispecific Chimeric Antigen Receptor Targeting CD19 and CD20

Cellular immunotherapy is an emerging and highly effective tumor treatment model, and is a new type of autoimmunolgy treatment for cancer. It is a method for in vitro culture and amplification of immune cells collected from a patient using biotechnology and biological agents, and then the cells are transfused back to the patient to stimulate and enhance the body's autoimmune function, thereby achieving the purpose of treating tumors. The skilled in the art have been working to develop new cellular immunotherapy to increase the efficiency and reduce the side effect.

The present invention proposes a rational and optimized single-chain design and system, that is, combined bispecific CAR, which can be effectively integrated into primary human T cells, and can simultaneously target CD19 and CD20 when the T cells are activated. The CAR-T cells of the invention are capable of recognizing two antigens (CD19 and CD20). The invention provides a very effective potential method for preventing antigen escape.

The present invention uses CAR that simultaneously targets CD19 and CD20. Compared with CARs that target a single antigen, the affinity is enhanced, the activity of T cells is increased, and the targets have an additive or synergistic effect. In addition, due to uneven expression levels of CD19 and CD20 in tumor cells, double target CAR-T therapy has a wider scope. The CAR-T that simultaneously targets CD19 and CD20 on the surface of tumor cells can reduce the possibility of antigen escape caused by down-regulation or deletion of single surface antigen.

Bispecificity means that the same CAR can specifically bind and immunorecognize two different antigens, and the CAR can generate an immune response by binding to any one of the antigens.

The CD19 and CD20 bispecific CAR of the present invention has a single structure and comprises anti-CD19 and anti-CD20 scFvs. Wherein, the CAR comprises a CD19 scFv and a CD20 scFv, and the amino acid sequences, sequencing and hinge of CD19 scFv and CD20 scFv are the main factors affecting its function.

Specifically, the chimeric antigen receptor (CAR) of the invention comprises an extracellular domain, a transmembrane domain, and an intracellular domain. The extracellular domain comprises a target-specific binding element (also known as an antigen binding domain). The intracellular domain comprises a co-stimulatory signaling region and a (chain. The co-stimulatory signaling region refers to a part of the intracellular domain that comprises a co-stimulatory molecule. The co-stimulatory molecule is a cell surface molecule required for efficient response of lymphocytes to antigens, rather than an antigen receptor or ligand thereof.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that plays a role of linking the transmembrane domain to the extracellular domain or the cytoplasmic domain in a polypeptide chain. The linker may comprise 0-300 amino acids, preferably 2-100 amino acids and most preferably 3-50 amino acids.

In a preferred embodiment of the invention, the extracellular domain of the CAR provided in the present invention comprises an antigen binding domain targeting CD19 and CD20. When the CAR of the present invention is expressed in T cell, antigen recognition can be performed based on antigen binding specificity. When the CAR binds to its associated antigen, it affects tumor cell, causing tumor cell to fail to grow, to death or to be affected otherwise, causing the patient's tumor burden to shrink or eliminate. The antigen binding domain is preferably fused to the intracellular domain from one or more of the co-stimulatory molecule and the (chain. Preferably, the antigen binding domain is fused with an intracellular domain of a combination of a 4-1BB signaling domain and a CD3ξ signaling domain.

As used herein, the "antigen binding domain" and "single-chain antibody fragment" refer to an Fab fragment, an Fab' fragment, an F $(ab')_2$ fragment, or a single Fv fragment that has antigen-binding activity. The Fv antibody contains the heavy chain variable region and the light chain variable region of the antibody, but has no constant region. The Fv antibody has the smallest antibody fragment with all antigen-binding sites. Generally, Fv antibodies also comprise a polypeptide linker between the VH and VL domains, and can form the structure required for antigen binding. The antigen binding domain is usually a scFv (single-chain variable fragment). The size of scFv is typically ⅙ of a complete antibody. The single-chain antibody is preferably an amino acid chain sequence encoded by a nucleotide chain. As a preferred embodiment of the present invention, the scFv comprises antibodies that specifically recognize CD19 and CD20.

As for the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some embodiments, transmembrane domains may be selected or modified by amino acid substitutions to avoid binding such domains to the transmembrane domain of the same or different surface membrane proteins, thereby minimizing the interaction with other members of the receptor complexes.

The intracellular domain in the CAR of the invention comprises the signaling domain of 4-1BB and the signaling domain of CD3ξ.

Preferably, the CAR structure of the present invention, in turn, comprises a signal peptide sequence (also known as leader sequence), an antigen recognition sequence (antigen-binding domain), a hinge region, a transmembrane region, a co-stimulatory factor signal region, and a CD3zeta signaling region (ξ chain portion). The order of connection is shown in FIG. 1.

In another preferred embodiment, the present CAR is TN-LEU-19. The antigen binding domain targeting CD20 comprises a heavy chain sequence (SEQ ID NO 1) and a light chain (VL) sequence (SEQ ID NO 2) of the single-chain variable region derived from Leu16 antibody.

Heavy chain sequence of single-chain variable region (VH) derived from Leu16 antibody:

(SEQ ID NO 1)

EVQLQQSGAELVKPGASVKMSCKASGYTFTSYNMHWVKQTPGQGLEWIGAI

YPGNGDTSYNQKFKGKATLTADKSSSTAYMQLSSLTSEDSADYYCARSNYY

GSSYWFFDVWGAGTTVTVSS

Light chain sequence of single-chain variable region (VL) derived from Leu16 antibody:

(SEQ ID NO 2)
DIVLTQSPAILSASPGEKVTMTCRASSSVNYMDWYQKKPGSSPKPWIYATS

NLASGVPARFSGSGSGTSYSLTISRVEAEDAATYYCQQWSFNPPTFGGGTK

LEIK

In another preferred embodiment, the present CAR is TN-OF-19. The antigen binding domain targeting CD20 comprises a heavy chain sequence (SEQ ID NO 3) and a light chain sequence (SEQ ID NO 4) of the single-chain variable region derived from Ofatumumab antibody.

Heavy chain sequence of single-chain variable region (VH) derived from Ofatumumab antibody:

(SEQ ID NO 3)
EVQLVESGGGLVQPGRSLRLSCAASGFTFNDYAMHWVRQAPGKGLEWVSTI

SWNSGSIGYADSVKGRFTISRDNAKKSLYLQMNSLRAEDTALYYCAKDIQY

GNYYYGMDVWGQGTTVTVSS

Light chain sequence of single-chain variable region (VL) derived from Ofatumumab antibody:

(SEQ ID NO 4)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPITFGQ

GTRLEIK

In another preferred embodiment, the antigen-binding domain targeting CD19 in the CAR of the present invention comprises a light chain (VL) sequence (SEQ ID NO 5) and a heavy chain sequence (SEQ ID NO 6) of the single-chain variable region derived from FMC63 antibody.

Amino acid sequence of the light chain of single-chain variable region (VL) derived from FMC63 antibody:

(SEQ ID NO 5)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT

Nucleotide sequence of the light chain of single-chain variable region (VL) derived from FMC63 antibody:

```
                                                          (SEQ ID NO 21)
gacatccaga tgacacagac tacatcctcc ctgtctgcct ctctgggaga cagagtcacc  60

atcagttgca gggcaagtca ggacattagt aaatatttaa attggtatca gcagaaacca 120

gatggaactg ttaaactcct gatctaccat acatcaagat tacactcagg agtcccatca 180

aggttcagtg gcagtgggtc tggaacagat tattctctca ccattagcaa cctggagcaa 240

gaagatattg ccacttactt ttgccaacag ggtaatacgc ttccgtacac gttcggaggg 300

gggaccaagc tggagatcac a                                           321
```

Amino acid sequence of the heavy chain of single-chain variable region (VH) derived from FMC63 antibody:

(SEQ ID NO 6)
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS

Nucleotide sequence of the heavy chain of single-chain variable region (VH) derived from FMC63 antibody:

```
                                                          (SEQ ID NO 22)
gaggtgaaac tgcaggagtc aggacctggc ctggtggcgc cctcacagag cctgtccgtc  60

acatgcactg tctcaggggt ctcattaccc gactatggtg taagctggat tcgccagcct 120

ccacgaaagg gtctggagtg gctgggagta atatggggta gtgaaaccac atactataat 180

tcagctctca aatccagact gaccatcatc aaggacaact ccaagagcca agttttctta 240

aaaatgaaca gtctgcaaac tgatgacaca gccatttact actgtgccaa acattattac 300

tacggtggta gctatgctat ggactactgg ggccaaggaa cctcagtcac cgtctcctca 360
```

Specifically, the sequences of other elements in the CAR of the present invention are as follows:

The leader sequence is the leader sequence of CD8 antigen:

```
                                        (SEQ ID NO 8)
MALPVTALLLPLALLLHAARP
```

The linker sequences (i.e., flexible linker I) between the heavy chain and light chain of the single-chain variable region are:

```
Amino acid sequence:
                                        (SEQ ID NO 19)
GGGGSGGGGSGGGGS

Nucleic acid sequence:
                                        (SEQ ID NO 20)
ggtggcggtg gctcgggcgg tggtgggtcg

ggtggcggcg gatct
```

The hinge region is selected from the sequence of IgG4 Hinge-CH2-CH3:

```
                                        (SEQ ID NO 9)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK
```

The transmembrane region is the transmembrane region sequence of CD8 (CD8TM) or CD28 (CD28TM) antigen:

```
                                        (SEQ ID NO 10)
CD8TM: IYIWAPLAGTCGVLLLSLVITLYC

                                        (SEQ ID NO 11)
CD28TM: FWVLVVVGGVLACYSLLVTVAFIIFWV
```

The co-stimulatory factor signal region is derived from the sequence of 4-1BB or CD28 cytoplasmic signaling motif:

```
4-1BB:
                                        (SEQ ID NO 12)
KRGRKKLLYIFKQPFMRPVQTTQEEDGCSCRFPEEEEGGCEL

CD28:
                                        (SEQ ID NO 13)
RSKRSRLLHSDYMNMTPRRPGPTRKHYQPYAPPRDFAAYRS
```

The signaling region of CD3ξ is derived from the sequence of immunorecceptor tyrosine-based activation motif (ITAM) of CD3ξ in the TCR complex:

```
                                        (SEQ ID NO 14)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR
```

In a preferred embodiment, the complete nucleic acid sequences and amino acid sequences of the two CARs constructed in the present invention are as follows:

The complete nucleic acid sequence of TN-OF-19 is as follows:

```
                                        (SEQ ID NO: 18)
ATGGCCTTACCAGTGACCGCCTTGCTCCTGCCGCTGGCCTTGCTGCTCCACGCC

GCCAGGCCGGAAATTGTGTTGACACAGTCTCCAGCCACCCTGTCTTTGTCTCCAGGG

GAAAGAGCCACCCTCTCCTGCAGGGCCAGTCAGAGTGTTAGCAGCTACTTAGCCTG

GTACCAACAGAAACCTGGCCAGGCTCCCAGGCTCCTCATCTATGATGCATCCAACAG

GGCCACTGGCATCCCAGCCAGGTTCAGTGGCAGTGGGTCTGGGACAGACTTCACTCT

CACCATCAGCAGCCTAGAGCCTGAAGATTTTGCAGTTTATTACTGTCAGCAGCGTAG

CAACTGGCCGATCACCTTCGGCCAAGGGACACGACTGGAGATTAAAGGCAGTACTA

GCGGTGGTGGCTCCGGGGGCGGTTCCGGTGGGGGCGGCAGCAGCGAAGTGCAGCTG

GTGGAGTCTGGGGGAGGCTTGGTACAGCCTGGCAGGTCCCTGAGACTCTCCTGTGCA

GCCTCTGGATTCACCTTTAATGATTATGCCATGCACTGGGTCCGGCAAGCTCCAGGG

AAGGGCCTGGAGTGGGTCTCAACTATTAGTTGGAATAGTGGTTCCATAGGCTATGCG

GACTCTGTGAAGGGCCGATTCACCATCTCCAGAGACAACGCCAAGAAGTCCCTGTA

TCTGCAAATGAACAGTCTGAGAGCTGAGGACACGGCCTTGTATTACTGTGCAAAAG

ATATACAGTACGGCAACTACTACTACGGTATGGACGTCTGGGGCCAAGGGACCACG

GTCACCGTCTCCTCAGGAGGTGGTGGATCCGAGGTGAAGCTGCAGGAAAGCGGCCC

TGGCCTGGTGGCCCCCAGCCAGAGCCTGAGCGTGACCTGCACCGTGAGCGGCGTGA

GCCTGCCCGACTACGGCGTGAGCTGGATCCGGCAGCCCCCCAGGAAGGGCCTGGAA

TGGCTGGGCGTGATCTGGGGCAGCGAGACCACCTACTACAACAGCGCCCTGAAGAG
```

-continued

CCGGCTGACCATCATCAAGGACAACAGCAAGAGCCAGGTGTTCCTGAAGATGAACA

GCCTGCAGACCGACGACACCGCCATCTACTACTGCGCCAAGCACTACTACTACGGC

GGCAGCTACGCCATGGACTACTGGGGCCAGGGCACCAGCGTGACCGTGAGCAGCGG

CAGCACCTCCGGCAGCGGCAAGCCTGGCAGCGGCGAGGGCAGCACCAAGGGCGAC

ATCCAGATGACCCAGACCACCTCCAGCCTGAGCGCCAGCCTGGGCGACCGGGTGAC

CATCAGCTGCCGGGCCAGCCAGGACATCAGCAAGTACCTGAACTGGTATCAGCAGA

AGCCCGACGGCACCGTCAAGCTGCTGATCTACCACACCAGCCGGCTGCACAGCGGC

GTGCCCAGCCGGTTTAGCGGCAGCGGCTCCGGCACCGACTACAGCCTGACCATCTCC

AACCTGGAACAGGAAGATATCGCCACCTACTTTTGCCAGCAGGGCAACACACTGCC

CTACACCTTTGGCGGCGGAACAAAGCTGGAAATCACCGAGAGCAAGTACGGACCGC

CCTGCCCCCCTTGCCCTATGTTCTGGGTGCTGGTGGTGGTCGGAGGCGTGCTGGCCT

GCTACAGCCTGCTGGTCACCGTGGCCTTCATCATCTTTTGGGTGAAACGGGGCAGAA

AGAAACTCCTGTATATATTCAAACAACCATTTATGAGACCAGTACAAACTACTCAAG

AGGAAGATGGCTGTAGCTGCCGATTTCCAGAAGAAGAAGAAGGAGGATGTGAACTG

CGGGTGAAGTTCAGCAGAAGCGCCGACGCCCCTGCCTACCAGCAGGGCCAGAATCA

GCTGTACAACGAGCTGAACCTGGGCAGAAGGGAAGAGTACGACGTCCTGGATAAGC

GGAGAGGCCGGGACCCTGAGATGGGCGGCAAGCCTCGGCGGAAGAACCCCCAGGA

AGGCCTGTATAACGAACTGCAGAAAGACAAGATGGCCGAGGCCTACAGCGAGATCG

GCATGAAGGGCGAGCGGAGGCGGGGCAAGGGCCACGACGGCCTGTATCAGGGCCT

GTCCACCGCCACCAAGGATACCTACGACGCCCTGCACATGCAGGCCCTGCCCCCAA

GG

The complete amino acid sequence of TN-OF-19 is as follows:

(SEQ ID NO: 16)

MALPVTALLLPLALLLHAARPEIVLTQSPATLSLSPGERATLSCRASQSV

SSYLAWYQQKPGQAPRLLIYDASNRATGIPARFSGSGSGTDFTLTISSLE

PEDFAVYYCQQRSNWPITFGQGTRLEIKGSTSGGGSGGGSGGGGSSEVQL

VESGGGLVQPGRSLRLSCAASGFTFNDYAMHWVRQAPGKGLEWVSTISWN

SGSIGYADSVKGRFTISRDNAKKSLYLQMNSLRAEDTALYYCAKDIQYGN

YYYGMDVWGQGTTVTVSSGGGGSEVKLQESGPGLVAPSQSLSVTCTVSGV

SLPDYGVSWIRQPPRKGLEWLGVIWGSETTYYNSALKSRLTIIKDNSKSQ

-continued

VFLKMNSLQTDDTAIYYCAKHYYYGGSYAMDYWGQGTSVTVSSGSTSGSG

KPGSGEGSTKGDIQMTQTTSSLSASLGDRVTISCRASQDISKYLNWYQQK

PDGTVKLLIYHTSRLHSGVPSRFSGSGSGTDYSLTISNLEQEDIATYFCQ

QGNTLPYTFGGGTKLEITESKYGPPCPPCPMFWVLVVVGGVLACYSLLVT

VAFIIFWVKRGRKKLLYIFKQPFMRPVQTTQEEDGCSCRFPEEEEGGCEL

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

The complete nucleic acid sequence of TN-LEU-19 is as follows:

(SEQ ID NO: 17)

ATGGAGACAGACACACTCCTGCTATGGGTGCTGCTGCTCTGGGTTCCAGGTTCC

ACAGGTGACATTGTGCTGACCCAATCTCCAGCTATCCTGTCTGCATCTCCAGGGGAG

AAGGTCACAATGACTTGCAGGGCCAGCTCAAGTGTAAATTACATGGACTGGTACCA

GAAGAAGCCAGGATCCTCCCCCAAACCCTGGATTTATGCCACATCCAACCTGGCTTC

TGGAGTCCCTGCTCGCTTCAGTGGCAGTGGGTCTGGGACCTCTTACTCTCTCACAATC

AGCAGAGTGGAGGCTGAAGATGCTGCCACTTATTACTGCCAGCAGTGGAGTTTTAAT

CCACCCACGTTCGGAGGGGGGACCAAGCTGGAAATAAAAGGCAGTACTAGCGGTGG

-continued

TGGCTCCGGGGGCGGTTCCGGTGGGGGCGGCAGCAGCGAGGTGCAGCTGCAGCAGT

CTGGGGCTGAGCTGGTGAAGCCTGGGGCCTCAGTGAAGATGTCCTGCAAGGCTTCTG

GCTACACATTTACCAGTTACAATATGCACTGGGTAAAGCAGACACCTGGACAGGGC

CTGGAATGGATTGGAGCTATTTATCCAGGAAATGGTGATACTTCCTACAATCAGAAG

TTCAAAGGCAAGGCCACATTGACTGCAGACAAATCCTCCAGCACAGCCTACATGCA

GCTCAGCAGCCTGACATCTGAGGACTCTGCGGACTATTACTGTGCAAGATCTAATTA

TTACGGTAGTAGCTACTGGTTCTTCGATGTCTGGGGCGCAGGGACCACGGTCACCGT

CTCCTCAGGAGGTGGTGGATCCGAGGTGAAGCTGCAGGAAAGCGGCCCTGGCCTGG

TGGCCCCCAGCCAGAGCCTGAGCGTGACCTGCACCGTGAGCGGCGTGAGCCTGCCC

GACTACGGCGTGAGCTGGATCCGGCAGCCCCCCAGGAAGGGCCTGGAATGGCTGGG

CGTGATCTGGGGCAGCGAGACCACCTACTACAACAGCGCCCTGAAGAGCCGGCTGA

CCATCATCAAGGACAACAGCAAGAGCCAGGTGTTCCTGAAGATGAACAGCCTGCAG

ACCGACGACACCGCCATCTACTACTGCGCCAAGCACTACTACTACGGCGGCAGCTA

CGCCATGGACTACTGGGGCCAGGGCACCAGCGTGACCGTGAGCAGCGGCAGCACCT

CCGGCAGCGGCAAGCCTGGCAGCGGCGAGGGCAGCACCAAGGGCGACATCCAGAT

GACCCAGACCACCTCCAGCCTGAGCGCCAGCCTGGGCGACCGGGTGACCATCAGCT

GCCGGGCCAGCCAGGACATCAGCAAGTACCTGAACTGGTATCAGCAGAAGCCCGAC

GGCACCGTCAAGCTGCTGATCTACCACACCAGCCGGCTGCACAGCGGCGTGCCCAG

CCGGTTTAGCGGCAGCGGCTCCGGCACCGACTACAGCCTGACCATCTCCAACCTGGA

ACAGGAAGATATCGCCACCTACTTTTGCCAGCAGGGCAACACACTGCCCTACACCTT

TGGCGGCGGAACAAAGCTGGAAATCACCGAGAGCAAGTACGGACCGCCCTGCCCCC

CTTGCCCTATGTTCTGGGTGCTGGTGGTGGTCGGAGGCGTGCTGGCCTGCTACAGCC

TGCTGGTCACCGTGGCCTTCATCATCTTTTGGGTGAAACGGGGCAGAAAGAAACTCC

TGTATATATTCAAACAACCATTTATGAGACCAGTACAAACTACTCAAGAGGAAGAT

GGCTGTAGCTGCCGATTTCCAGAAGAAGAAGAAGGAGGATGTGAACTGCGGGTGAA

GTTCAGCAGAAGCGCCGACGCCCCTGCCTACCAGCAGGGCCAGAATCAGCTGTACA

ACGAGCTGAACCTGGGCAGAAGGGAAGAGTACGACGTCCTGGATAAGCGGAGAGG

CCGGGACCCTGAGATGGGCGGCAAGCCTCGGCGGAAGAACCCCCAGGAAGGCCTGT

ATAACGAACTGCAGAAAGACAAGATGGCCGAGGCCTACAGCGAGATCGGCATGAA

GGGCGAGCGGAGGCGGGGCAAGGGCCACGACGGCCTGTATCAGGGCCTGTCCACCG

CCACCAAGGATACCTACGACGCCCTGCACATGCAGGCCCTGCCCCCAAGG

The complete amino acid sequence of TN-LEU-19 is as follows:

(SEQ ID NO: 15)

METDTLLLWVLLLWVPGSTG*DIVLTQSPAILSASPGEKVTMTCRASSSVN*

*YMDWYQKKPGSSPKPWIYATSNLASGVPARFSGSGSGTSYSLTISRVEAE*

*DAATYYCQQWSFNPPTFGGGTKLEIK*GSTSGGGSGGGSGGGGSSEVQLQQ

SGAELVKPGASVKMSCKASGYTFTSYNMHWVKQTPGQGLEWIGAIYPGNG

DTSYNQKFKGKATLTADKSSSTAYMQLSSLTSEDSADYYCARSNYYGSSY

WFFDVWGAGTTVTVSSGGGGSEVKLQESGPGLVAPSQSLSVTCTVSGVSL

-continued

PDYGVSWIRQPPRKGLEWLGVIWGSETTYYNSALKSRLTIIKDNSKSQVF

LKMNSLQTDDTAIYYCAKHYYYGGSYAMDYWGQGTSVTVSSGSTSGSGKP

GSGEGSTKG*DIQMTQTTSSLSASLGDRVTISCRASQDISKYLNWYQQKPD*

*GTVKLLIYHTSRLHSGVPSRFSGSGSGTDYSLTISNLEQEDIATYFCQQG*

*NTLPYTFGGGTKLEIT*ESKYGPPCPPCPMFWVLVVVGGVLACYSLLVTVA

FIIFWVKRGRKKLLYIFKQPFMRPVQTTQEEDGCSCRFPEEEEGGCELRV

KFSRSADAPAYQQGQNQLYNELNLGRREEYDVLDKRRGRDPEMGGKPRRK

-continued

```
NPQEGLYNELQKDKMAEAYSEIGMKGERRRGKGHDGLYQGLSTATKDTYD

ALHMQALPPR
```

The design of the BICAR of the present invention has the following advantages:

First, CD19 and CD20 are expressed in most malignant B-cell tumors. Secondly, in general, when expanding CAR structure to increase T cell recognition ability, problems such as increased adverse targeting, increased cytotoxicity, and increased side effects are often encountered. However, this is not the case for CD19 and CD20 because both of them are only expressed in B cells with the same tumor toxicity curve. Finally, the expression of CD19 and CD20 in B cells can promote the survival of B cells. And the loss of both antigens during treatment is a very low probability event. Therefore, targeting CD19 and CD20 is expected to provide effective prevention of antigen escape of malignant B cells.

Compared with the single CAR of CD19 or CD20, BICAR has the following advantages:

First, compared with expressing two independent CARs, when expressing BICAR in a single T cell, the DNA footprint is significantly reduced (the DNA length is reduced by 40%). The size and the length of structure can significantly affect the packaging and transduction efficiency of the viral vector, thus directly affecting the clinical efficacy. Secondly, compared to the mixture of two different single CARs, BICAR can significantly reduce the cost of treatment (BICAR is completely compatible with the current T cell production process without adding additional burden) and increase the clinical cure rate. Finally, CD19 and CD20 have been verified in a large number of clinical studies and are relatively safe.

In the present invention, we constructed two types of chimeric antigen receptor structures (TN-LEU-19, TH-OF-19) targeting CD19 and CD20 based on the sequence of CD19 mouse-derived monoclonal antibody FMC63 and the sequences of CD20 mouse-derived monoclonal antibody leu-16 and Ofatumumab. We completed the analysis and identification of the expression levels, in vitro activation capacity, and tumor cell killing efficacy of these two chimeric antigen receptors in primary T cells. Finally, it was found that the T-cells modified with TN-LEU-19 or TH-OF-19 chimeric antigen receptors have a strong ability to kill in vitro and to clear malignant tumors carrying CD19 and CD20 positive antigens in vivo, and Ofatumumab is better than leu16. This provides a new effective method and preparation for the clinical application of CAR-T in the treatment of CD19 and CD20-positive leukemias and lymphomas.

The present invention designed and optimized single-specific and double-specific CARs. These CARs have a powerful killing ability against B-cell malignancies expressing CD19 or CD20. BICAR allows a single T-cell product to target two clinically validated antigens associated with B-cell leukemia and lymphoma, ultimately reducing the risk of tumor recurrence due to the loss or escape of a single antigen. The invention can be further used in the design of new BICAR, thus increasing the antigen's applicability and increasing the efficacy of T cell therapy for cancer.

Chimeric Antigen Receptor T Cell (CAR-T Cell)

As used herein, the terms "CAR-T cell", "CAR-T", "CART", "CAR-T cell of the present invention" all refer to the CAR-T cell that targets both CD19 and CD20 of the forth aspect of the invention. Specifically, the CAR structure of the CAR-T cells comprises an anti-CD19 scFv, an anti-CD20 scFv, a hinge region, a transmembrane region, and an intracellular T cell signaling region in turn, wherein the anti-CD20 scFv and anti-CD19 scFv are linked with a peptide having multiple repeating structures (G4S). Compared with CAR-T targeting a single antigen, the CAR-T cell that simultaneously recognizes two targets are more lethal and have a wider range of treatment.

Vector

The nucleic acid sequences coding for the desired molecules can be obtained using recombinant methods known in the art, such as, for example by screening libraries from cells expressing the gene, by deriving the gene from a vector known to comprise the same, or by isolating directly from cells and tissues containing the same, using standard techniques. Alternatively, the gene of interest can be produced synthetically.

The present invention also provides vectors in which the expression cassette of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression cassette or nucleic acid sequence of the invention is typically and operably linked to a promoter, and incorporated into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest comprise expression vectors, replication vectors, probe generation vectors, and sequencing vectors.

Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors comprise, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-1 10 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters comprise, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers comprise, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may comprise genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell comprise calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell comprise the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell comprise colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids comprise the fatty droplets that naturally occur in the cytoplasm as well as the class of compounds which contain long-chain aliphatic hydrocarbons and their derivatives, such as fatty acids, alcohols, amines, amino alcohols, and aldehydes.

In a preferred embodiment of the invention, the vector is a lentiviral vector.

Preparation

The invention provides a preparation comprising the CAR-T cell of the forth aspect of the invention, and a pharmaceutically acceptable carrier, diluent or excipient. In one embodiment, the preparation is a liquid preparation. Preferably, the preparation is an injection. Preferably, the concentration of the CAR-T cells in the preparation is $1\times10^3$-$1\times10^8$ cells/ml, more preferably $1\times10^4$-$1\times10^7$ cells/ml.

In one embodiment, the preparation may comprises buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The preparation of the invention is preferably formulated for intravenous administration.

Therapeutic Application

The invention comprises therapeutic applications using cells (e.g., T cells) transduced with a lentiviral vector (LV) encoding the expression cassette of the invention. The transduced T cells can target the tumor cell markers CD19 and CD20, synergistically activate T cells, and cause T cell immune responses, thereby significantly increasing the killing efficiency against tumor cells.

Thus, the present invention also provides a method for stimulating a T cell-mediated immune response to a target cell population or tissue in a mammal comprising the step of administering to the mammal a CAR-T cell of the invention.

In one embodiment, the present invention comprises a class of cell therapies, wherein T cells from autologous patient (or heterologous donor) are isolated, activated and genetically modified to generate CAR-T cells, and then injected into the same patient. The probability of graft versus host disease in this way is extremely low, and antigens are recognized by T cells in a non-MHC-restricted manner. In addition, one CAR-T can treat all cancers that express the antigen. Unlike antibody therapies, CAR-T cells are able to replicate in vivo resulting in long-term persistence that can lead to sustained tumor control.

In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-CD19CD20 CAR-T cell elicits an immune response specifically against cells expressing CD19 and CD20.

Although the data disclosed herein specifically discloses lentiviral vector comprising CD19CD20 scFv, hinge and transmembrane domain, and 4-1BB and CD3ξ signaling domains, the invention should be construed to comprise any number of variations for each of the components of the construct as described elsewhere herein.

Cancers that may be treated comprise tumors that are unvascularized or largely unvascularized, and tumors that are vascularized. Cancers may comprise non-solid tumors (such as hematological tumors, for example, leukemias and lymphomas) or solid tumors. Types of cancers to be treated with the CARs of the invention comprise, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also comprised.

Hematologic cancers are cancers of the blood or bone marrow. Examples of hematological (or hematogenous) cancers comprise leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, comprise fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expanding the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

The present invention provides methods for treating tumors comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide);

and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for patient administration can be performed according to art-accepted practices. In general, $1\times10^6$ to $1\times10^{10}$ of the modified T cells of the invention (e.g., CAR-T-19/20 cells) can be applied to patients by means of, for example, intravenous infusion each treatment or each course of treatment.

The advantages of the present invention are:

(1) As for the chimeric antigen receptor of the present invention, the extracellular antigen binding domain is specific anti-CD20 scFv and anti-CD19 scFv; the CAR formed by combining the specific anti-CD20 scFv and anti-CD19 scFv to a specific hinge region and an intracellular domain shows a great ability of killing tumor cells with low cytotoxicity and low side effects.

(2) The chimeric antigen receptor provided by the invention can achieve stable expression and membrane localization of CAR protein after T cells are infected by lentivirus carrying CAR gene.

(3) The CAR-modified T cell of the present invention has a longer survival time in vivo and strong anti-tumor efficacy; the optimized CAR with the IgG4 Hinge-CH2-CH3 linker region can avoid the binding of the Fc receptor and the subsequent ADCC effect (antibody-dependent cytotoxicity).

(4) Compared with two independent CARs, the bispecific chimeric antigen receptor of the present invention comprises both anti-CD20 scFv and anti-CD19 scFv, and the DNA footprint is significantly reduced (the DNA length is reduced by 40%), and the size of structure is small, which is beneficial for the packaging and transduction efficiency of viral vectors, thus directly improving clinical efficacy. In addition, the bispecific CAR of the invention has lower cost, higher cure rate, and more safety.

(5) The T-cells modified with TN-LEU-19 or TH-OF-19 chimeric antigen receptors of the present invention have very strong ability to kill in vitro and to clear malignant tumors carrying CD19 and CD20 positive antigens in vivo, and Ofatumumab is stronger. This provides a new effective method and preparation for the clinical application of CAR-T in the treatment of CD19 and CD20-positive leukemias and lymphomas.

(6) The CAR-T cells of the present invention have a killing effect on most malignant B-cell tumors, have a wider treatment range and a larger coverage rate, and can more effectively prevent tumor cells from escaping.

The present invention will be further illustrated below with reference to the specific examples. It is to be understood that these examples are for illustrative purposes only and are not intended to limit the scope of the invention. The experimental methods with no specific conditions described in the following examples are generally performed under the conventional conditions, or according to the manufacturer's instructions. Percentages and parts are by weight unless otherwise stated.

Example 1 Construction of Lentiviral Expression Vector

The full-length DNA was synthesized and cloned to achieve the construction of encoding plasmids. The pWPT lentiviral vector was selected as a cloning vector, and the cloning sites were BamH I and Sal I sites. Wherein, the structures of the two CARs designed in the present invention are shown in FIG. 1. The nucleic acid sequence of TN-LEU-19 is shown in SEQ ID NO 17, and the nucleic acid sequence of TN-OF-19 is shown in SEQ ID NO 18.

Example 2 Preparation of CAR-T Cells (1) Mononuclear cells (PBMCs) were isolated from venous blood of healthy people by density gradient centrifugation.

(2) On day 0, PBMCs were seeded in a cell culture flask previously coated with CD3 monoclonal antibody (OKT3) at a final concentration of 5 μg/mL and Retronectin (purchased from TAKARA) at a final concentration of 10 μg/mL. The medium was GT-551 cell culture medium containing 1% human albumin. Recombinant human interleukin 2 (IL-2) was added to the medium at a final concentration of 1000 U/mL. The cells were cultured in an incubator with a saturated humidity and 5% $CO_2$ at 37° C.

(3) On day 1, the supernatant of the PBMCs culture was slowly aspirated and discarded. New GT-551 cell culture medium containing 1% human albumin was added, and recombinant human interleukin 2 (IL-2) was added to the medium at a final concentration of 1000 U/mL. The cells were continuously cultured in an incubator with a saturated humidity and 5% $CO_2$ at 37° C.

(4) On day 3, fresh medium, concentrated and purified TN-LEU-19 or TN-OF-19 lentivirus solution, protamine sulfate (12 ug/ml), and IL-2 (at a final concentration of 1000 U/mL) were added. After 12 hours of infection in a 5% $CO_2$ incubator at 37° C., the culture medium was discarded, and fresh medium was added, and cultivation was continued in a 5% $CO_2$ incubator at 37° C.

(5) Starting from day 6, CAR-T19/20s (CART-TN-OF-19 and CART-TN-LEU-19) cells can be taken for corresponding activity assay.

Example 3 Detection of the Integration Rate of the CAR Gene in the T Cell Genome and the Expression Level of the Encoded Protein Thereof on the Membrane Surface $0.5\times10^6$ CAR-T19/20s cell sample cultured 7 days in Example 2 were taken respectively to test the transfection efficiency of the combined chimeric antigen receptor engineered T cells targeting CD19 and CD20. Protein L method was used to identify the expression level of CAR gene-encoded protein on the surface of T cell membrane in CAR-T19/20s cells cultured 7 days.

Figure 2:
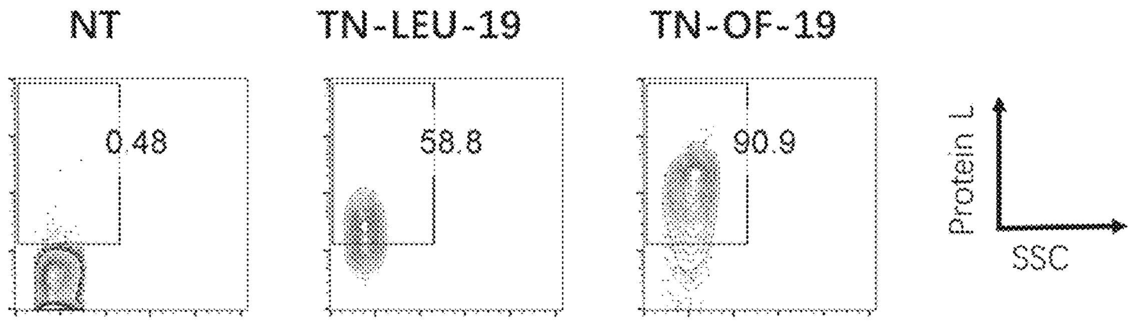
FIG. 2 shows the detection of transfection efficiency of engineered T cell with combined chimeric antigen receptors targeting CD19 and CD20. Protein L method was used to identify the expression level of CAR gene-encoded protein on the surface of T cell membrane in CAR-T19/20s cells cultured 7 days.

The result is shown in FIG. 2, and two CAR structures (FIG. 1) designed in the present invention can be expressed in their corresponding modified T cells and complete the cell membrane surface localization.

Example 4 Detection of the In Vitro Activation Ability of CAR-T19/20s

Cell activation level indicator proteins CD137 and IFNγ was detected using CAR-T19/20s cells cultured 7 days in Example 2. $1\times10^5$ of CART-T19/20 cells cultured 7 days were taken and cultured respectively with CD19, CD20-positive K562-CD19+, K562-CD20+, K562-CD19+CD20+ and Raji (naturally expressing CD19 and CD20) tumor cell line, as well as CD19CD20-negative K562 tumor cell line, or without tumor cells, in 200 μl of GT-551 medium for 18 h with a ratio of 1:1. Then the expression level of CD137 on the surface of T cell membrane and the secretion level of IFNγ in the culture supernatant were detected respectively.

Figure 3A:
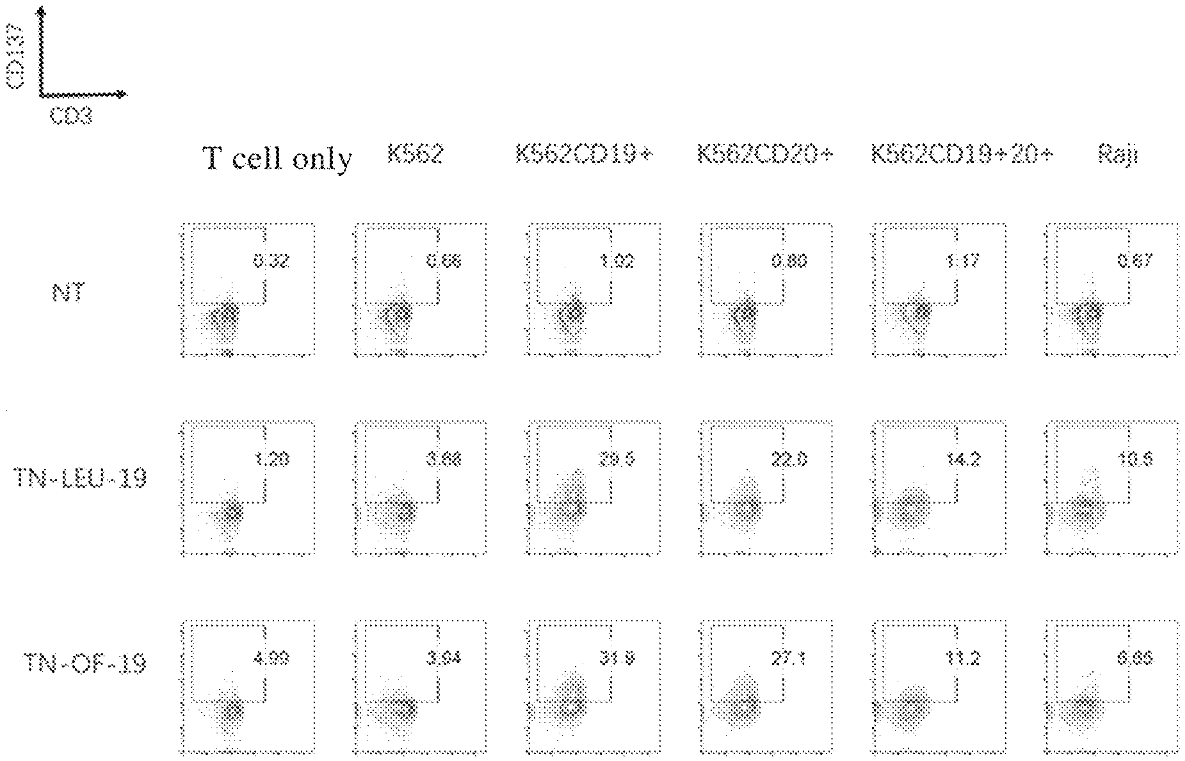
FIGS. 3A and 3B show the expression level of CD137 on the surface of T cell membrane (FIG. 3A) and the secretion level of IFNγ in the culture supernatant (FIG. 3B). Specifically, $1\times10^5$ of CAR-T19/20s cells cultured 7 days were taken and cultured respectively with CD19-positive K562-CD19+ tumor cell line, CD20-positive K562-CD20+ tumor cell line, CD19 and CD20 double positive K562-CD19+CD20+ tumor cell line, RAJI tumor cell line that naturally expresses CD19 and CD20, and CD19 and CD20 double negative K562 tumor cell line, or without tumor cells, in 200 μl of GT-551 medium for 18 h with a ratio of 1:1. Then the expression level of CD137 on the surface of T cell membrane and the secretion level of IFNγ in the culture supernatant were detected respectively.
Figure 3B:
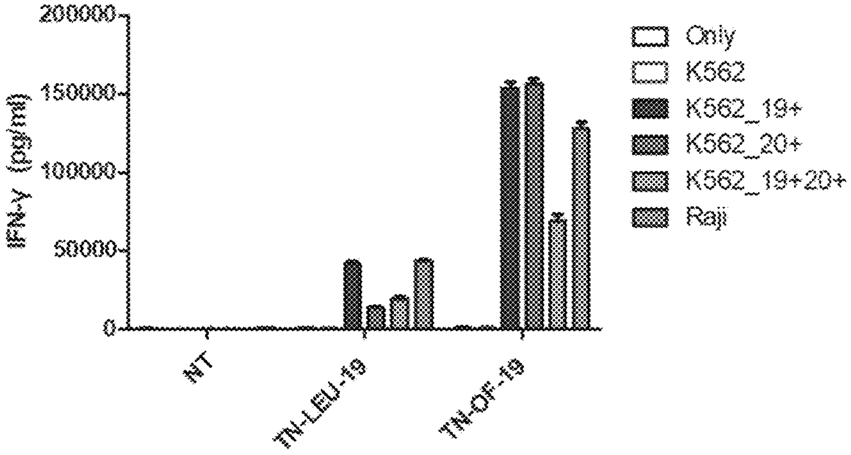

The results are shown in FIGS. 3A and 3B, the expressions of CD137 on the surface of two CART cells were detected, and the expressions of IFNγ in the culture supernatants were detected. Wherein, TN-OF-19 has higher CD137 activation level and IFNγ release level than TN-LEU-19.

Example 5 Detection of LDH Levels Released by CAR-T19/20s Cells for Killing Targeted Tumors In Vitro The CAR-T19/20s cells prepared in Example 2 were tested as follows:

Experimental wells, effector cell control wells, target cell control wells, target cell maximum release wells, medium control wells, and volume control wells (target cells comprise CD19, CD20 positive K562-CD19, K562-CD20, K562-CD19-CD20, and Raji cells; and effector cells comprise NT, CART-TN-LEU-19, and CART-TN-OF-19) were set.

The effect-target ratio was set, wherein number of effector cells:number of target cells=5:1, 10:1, 20:1, and 40:1. Number of cells: $1\times10^4$ of target cells, 50 ul/well; and effective cells are $5\times10^4$ cells/well, $1\times10^5$ cells/well, $2\times10^5$ cells/well, and $5\times10^5$ cells/well. Different dilution ratios of effector cells and target cells were added to the experimental wells with an effect-target ratio of 5:1, 10:1, 20:1, and 40:1. A total of 100 ul of the two cells (50 ul of effector cells+50 ul of target cells) were added to the cell culture plate, wherein 3 repeats were set. As for effector cell control wells, i.e. effector cells:target cells=5:0, 10:0, 20:0, and 40:0, $5\times10^4$/well, $10^5$/well, $2\times10^5$/well, $5\times10^5$/well of effector cells and 50 ul medium were added, wherein 2 repeats were set. As for target cell control wells, $1\times10^4$/well, 50 ul of target cell and 50 ul medium were added. As for target cells maximum release wells, $1\times10^4$, 50 ul of target cells and 50 ul medium were added. 10 ul lysate was added after incubating for 3 h and 15 min. As for the medium control wells, 100 ul medium was added. As for the volume control well, 100 ul medium was added.

After incubating for 3 h and 15 min, while adding 10 ul of lysate to the target cell maximum release wells, 10 ul of lysate was added and incubated at 37° C. The mixture was centrifuged at 250 g for 4 min and 50 ul/well of cell supernatant was transferred to a new enzyme plate. 50 ul/well of substrate mixture was added (kept in dark, with 12 ml of detection buffer added to a bottle of substrate mixture). The mixture was incubated at room temperature in dark for 30 min. Finally, 50 ul/well stop solution was added. The plate was read at 490 nm in 1 h, and the data was analyzed.

Figure 4:
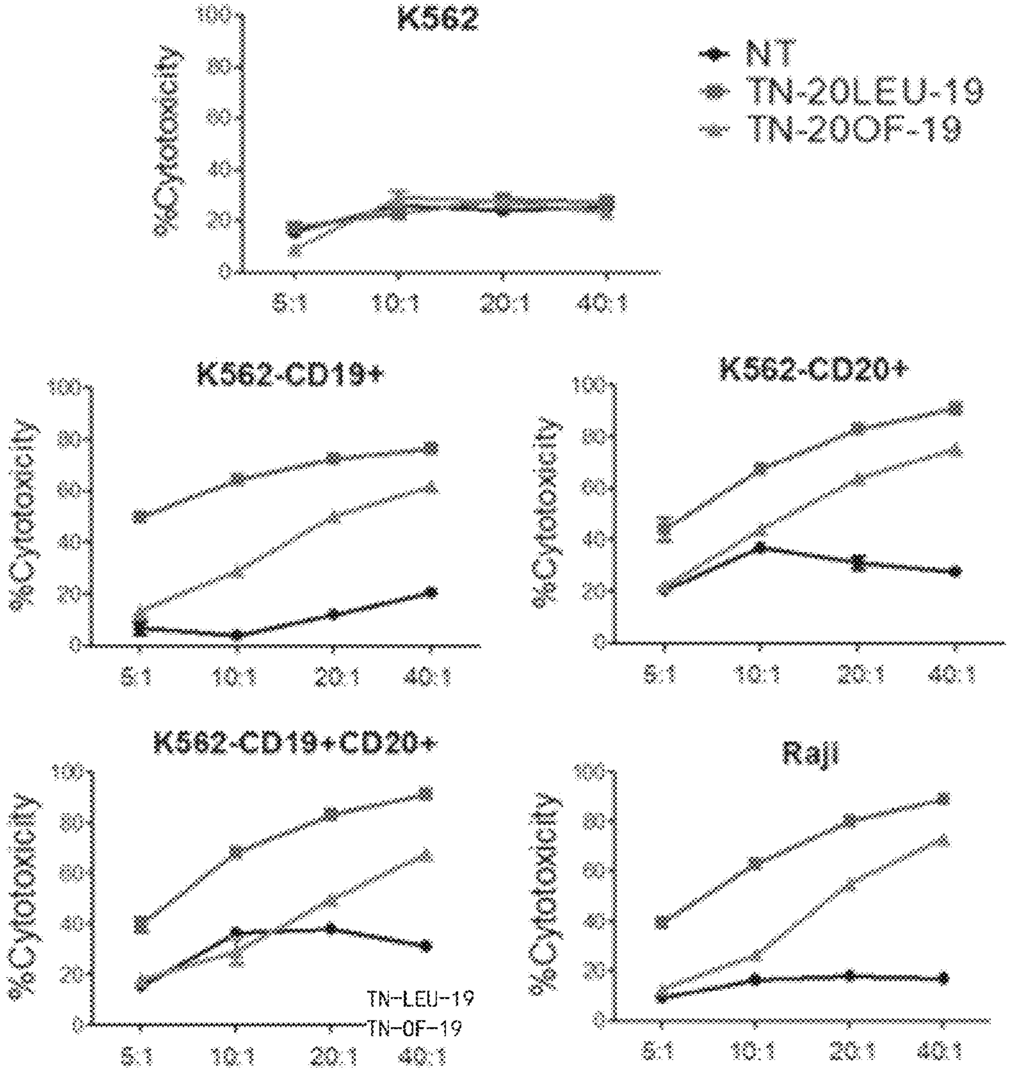
FIG. 4 shows the detection of tumor-killing activity of CAR-T19/20s cells, mainly by detecting the secretion level of LDH in the supernatant after co-culture. Specifically, $1\times10^4$ cells of CD19-positive K562-CD19+ tumor cell line, CD20-positive K562-CD20+ tumor cell line, CD19 and CD20 double positive K562-CD19+CD20+ tumor cell line, RAJI or RAMOS tumor cell line that naturally expresses CD19 and CD20, or CD19 and CD20 double negative K562 tumor cell line were co-cultured with the corresponding T cells, respectively, in 100 μl of GT-551 medium for 8 h with a ratio as shown in the figure. Then the secretion level of LDH was detected, and this figure shows the statistical analysis results of the percentages of LDH release in corresponding co-culture samples.

The results are shown in FIG. 4. Both CART cells can well induce apoptosis and release LDH in BCMA-positive tumor cells. Wherein, CART-TN-LEU-19 can better kill CD19CD20 positive tumor cells, and release higher LDH and the like than CART-TN-OF-19.

Example 6 Detection of CD107a Release Level During Tumor Cell Killing Induced by CAR-T19/20s Cells $1\times10^5$ cells of effective cell CAR-T19/20s (CART-TN-OF-19 and CART-TN-LEU-19) were co-cultured respectively with $2\times10^5$ of target tumor cells. The target cells are K562-CD19+, K562-CD20+, K562-CD19+CD20+, and K562 cells, Raji cells, Romas cells, respectively. At the same time, 3 μl of Anti-Human CD107Ape was added to each well for staining and placed at 37° C., 5% CO 2 for 1 hour, and then 3 μl of 1% Golgistop was added and placed at 37° C., 5% $CO_2$ for 3.5 hours. Next, 2 μl of CD8 FITC and 1.5 μl of CD3APC were added to each well and incubated at 37° C., 5% $CO_2$ for 30 min. 200 uL of FACS Buffer was added to each well and centrifuged at 300 g for 5 min. The liquid in the microplate was quickly discarded, and the remaining liquid was removed with absorbent paper. The plate was washed with FACS Buffer again. The plate was stained with 7-AAD and diluted with FACS Buffer (1:300). 200 uL of resuspended cells were added to each well. The plate was detected by flow cytometry after 10 min, light avoided. The results were statistically analyzed.

Figure 5:
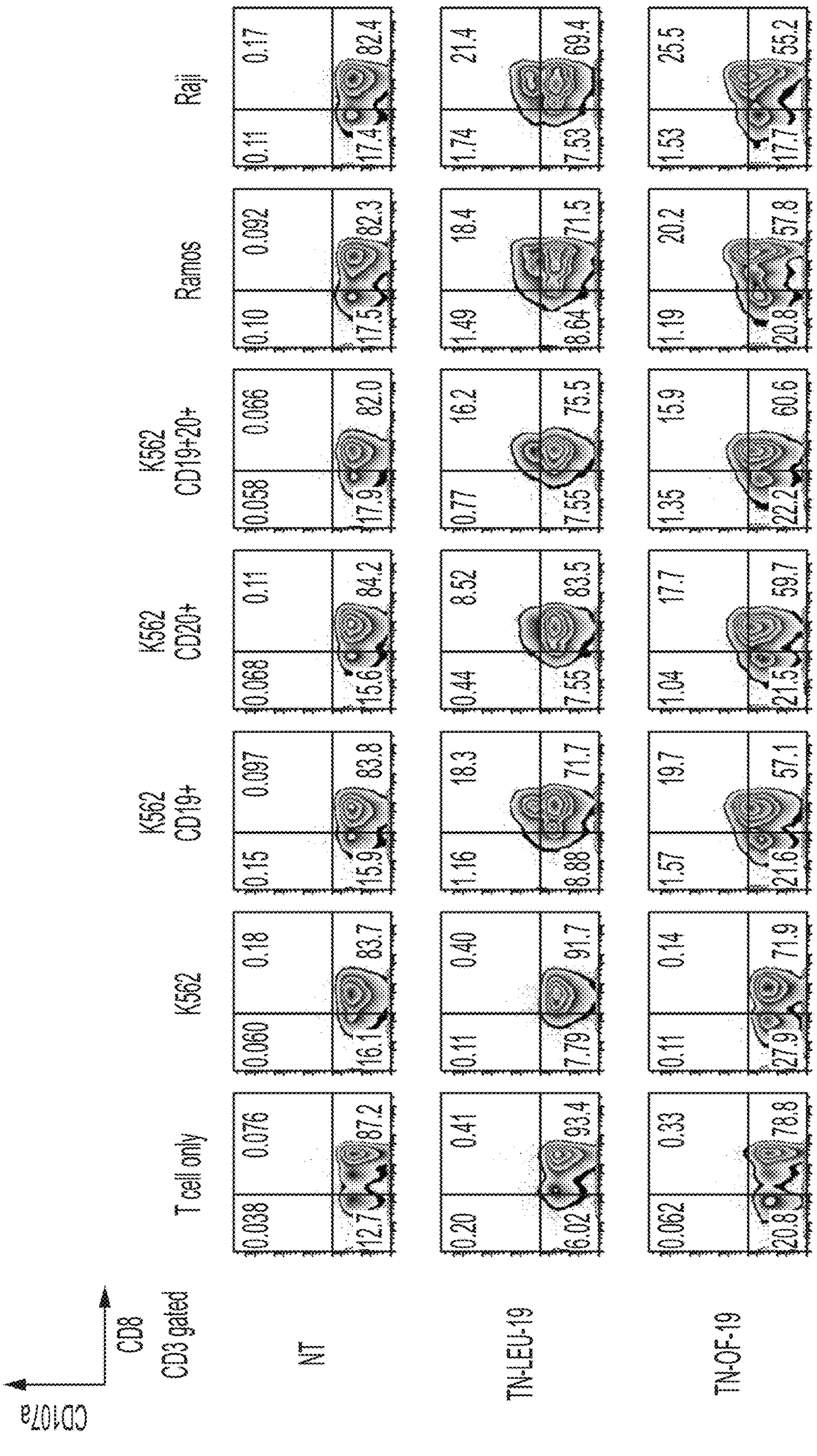
FIG. 5 shows the detection of tumor-killing activity of CAR-T19/20s cells, mainly by detecting the expression level of CD107a on the surface of T cell membrane. Specifically, $1\times10^5$ CAR-T19/20s cells were taken and cultured respectively with CD19-positive K562-CD19+ tumor cell line, CD20-positive K562-CD20+ tumor cell line, CD19 and CD20 double positive K562-CD19+CD20+ tumor cell line, RAJI or RAMOS tumor cell line that naturally expresses CD19 and CD20, and CD19 and CD20 double negative K562 tumor cell line, or without tumor cells, in 200 μl of GT-551 medium for 4 h with a ratio of 1:2. Then the expression level of CD137 on the surface of T cell membrane was detected respectively.

The results are shown in FIG. 5. Both CART cells can well induce the release of CD107a during tumor cell killing. Wherein, CART-TN-OF-19 have a slightly higher release of CD107a in the killing process and a stronger killing effect than CART-TN-LEU-19.

Example 7 Inhibitory Effect of CAR-T19/20s on Transplanted Tumor Cells in Mice

The tumor cells injected in animals are Raji. The tumor cells Raji carry a luciferase reporter gene (Raji expressing luciferase). In this experiment, tumor cells Raji were injected and grown in mice for one week, and then effector T cells were injected. The effector T cells were divided into three groups: NT, CART-TN-LEU-19, and CART-TN-OF-19.

Figure 6A:
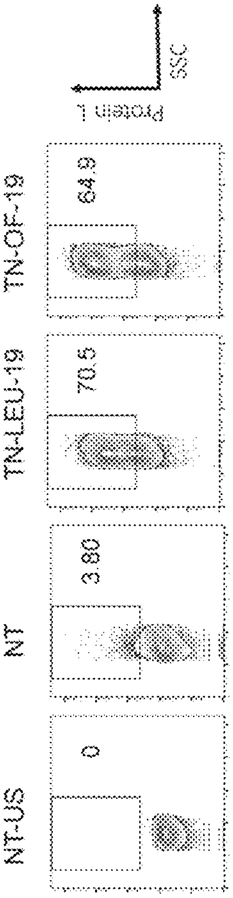
FIGS. 6A-6F shows the results of CAR-T19/20s cells killing tumor cells in RAJI-Luc/NSG leukemia model mice.
Figure 6B:
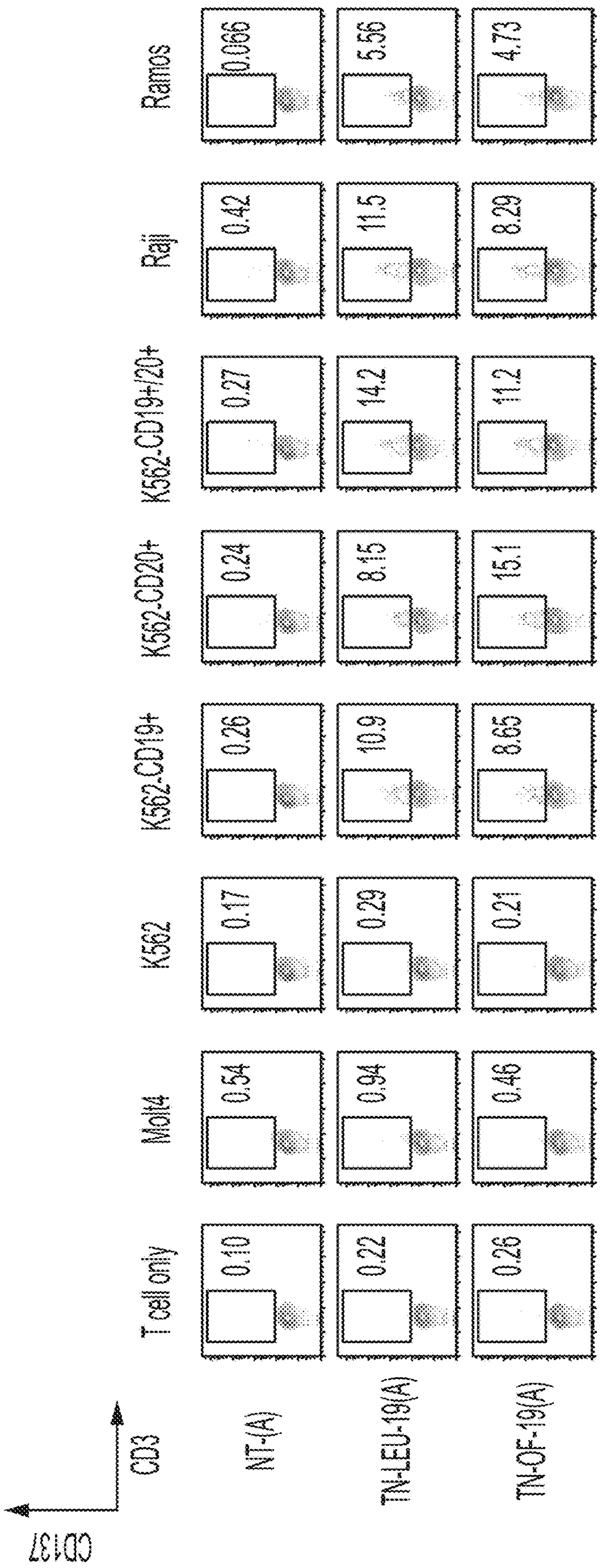
Figure 6C:
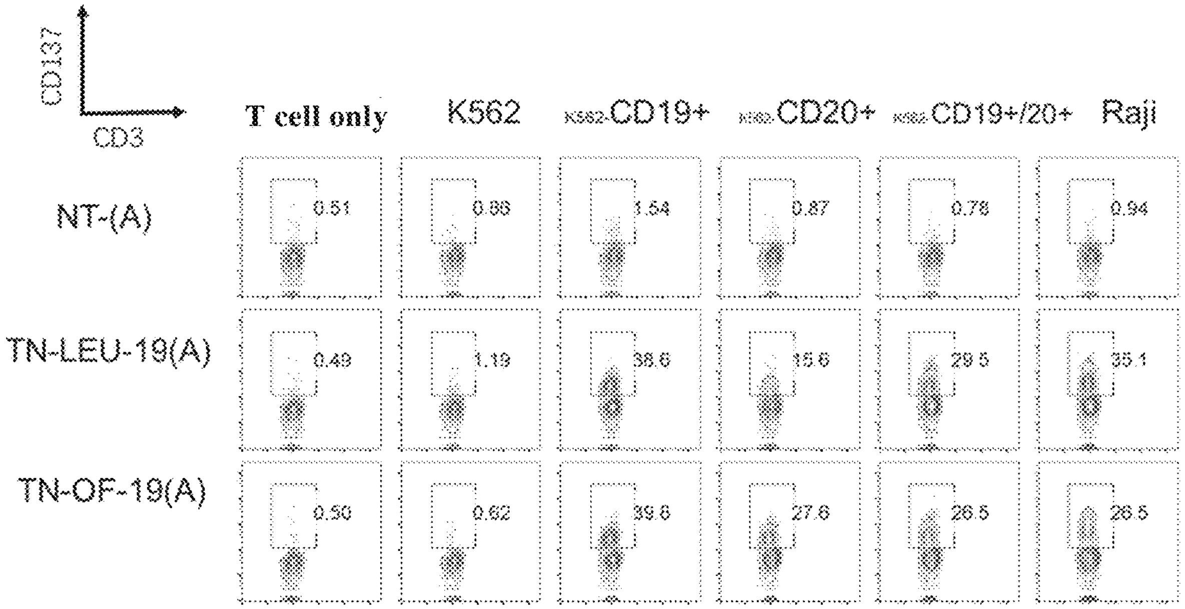
Figure 6D:
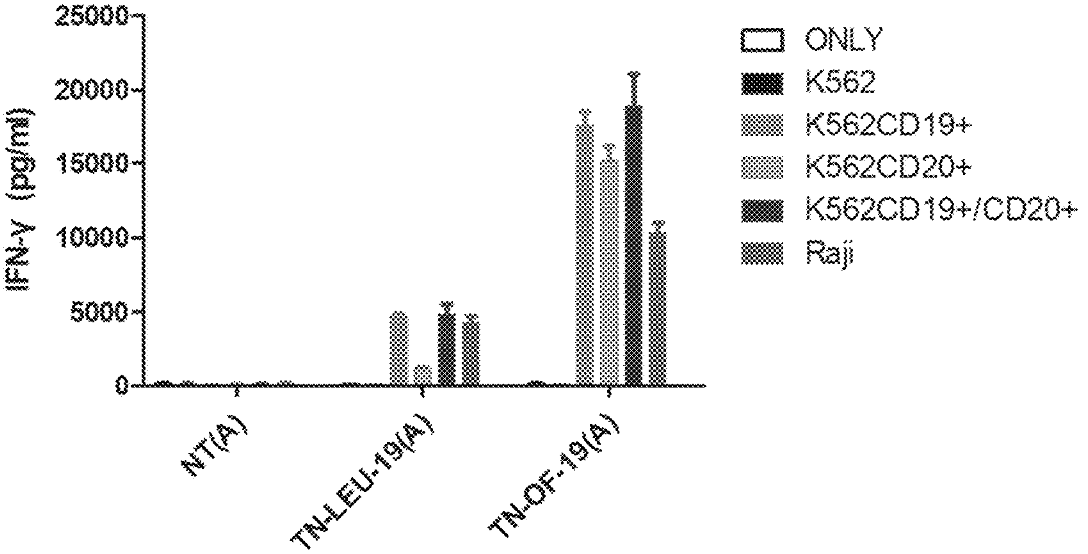

FIG. 6A shows the Protein L method for the detection of the transfection efficiency of combined chimeric antigen receptor engineered T cells targeting CD19CD20. The expression level of CD137 and the secretion level of IFNγ in the culture supernatant were the same as before. FIG. 6A shows the TN-LEU-19, TN-OF-19 both have high transfection efficiency. FIGS. 6B and 6C show the expression levels of CD137 on the surface of T cell membranes on the 10th day and the 18th day. Both TN-LEU-19 and TN-OF-19 can be expressed at high levels. FIG. 6D shows the secretion level of IFNγ in the culture supernatant on the 10th day. The results show that the level in TN-OF-19 is significantly higher than that in TN-LEU-19.

On the 21st day, the expanded effector T cells (sent to the Animal Experimental Center of Nanjing Medical University) were injected into the mice through the tail vein, and then the fluorescence intensity of the mice (via IVIS fluorescence imaging) and the weight of the mice were recorded every 7 days. The experiment was stopped on the 21st day, and the statistical results were analyzed.

Figure 6E:
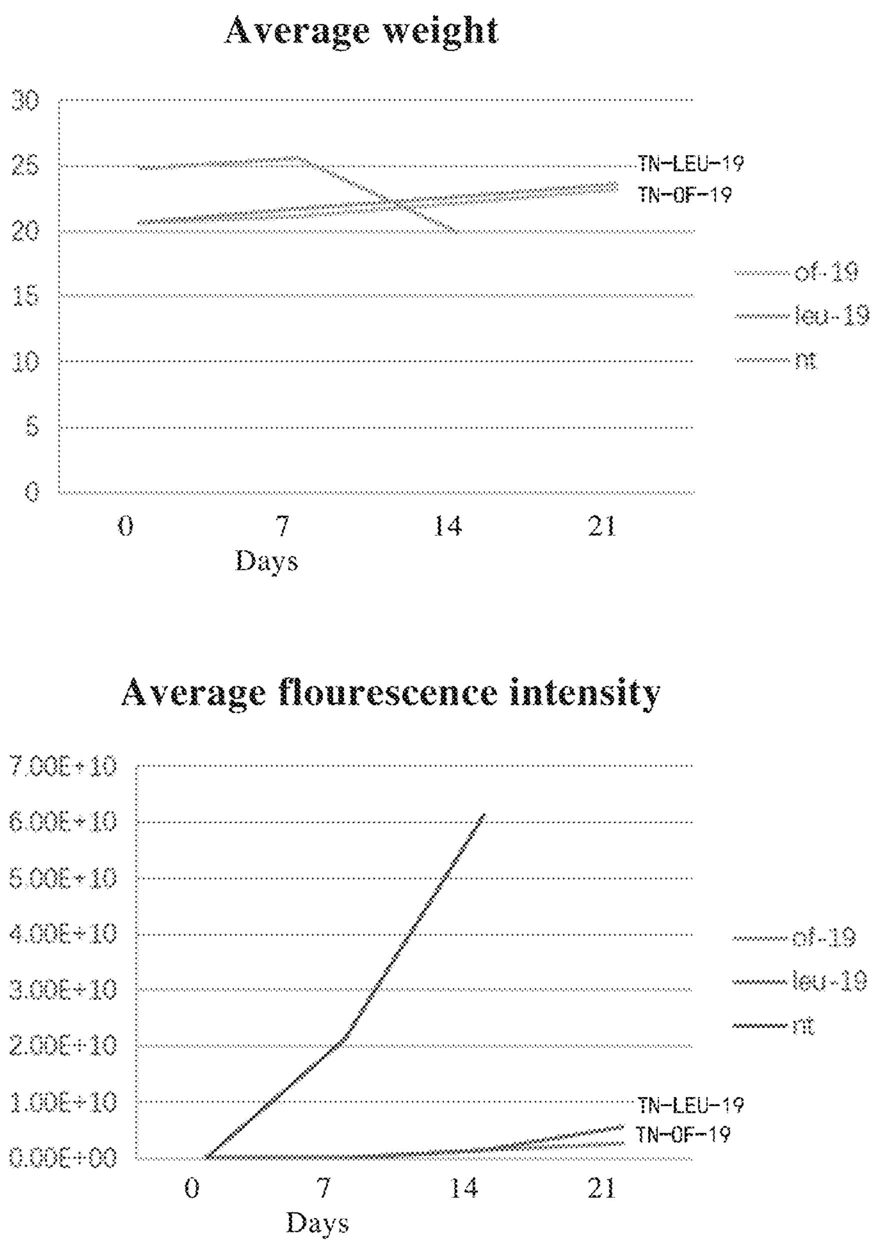

The results are shown in FIG. 6E. Both CART-TN-OF-19 and CART-TN-LEU-19 CART cells can well inhibit the growth of mouse tumor cells compared with NT. FIG. 6E (left) shows the weight change of mice after the injection of effector T cells into the three groups of mice. Compared with two types of CART cells CART-TN-OF-19 and CART-TN-LEU-19, the mice of NT showed a significant decrease in body weight and the mice in both CART cell groups gained slightly more weight. FIG. 6E (right) shows the average fluorescence intensity of the three groups of mice. The results show that the average fluorescence intensity of the mice in the NT group increased significantly, while the average of the fluorescence intensities of the mice in the two CART cell groups decreased significantly, and even difficult to detect.

Figure 6F:
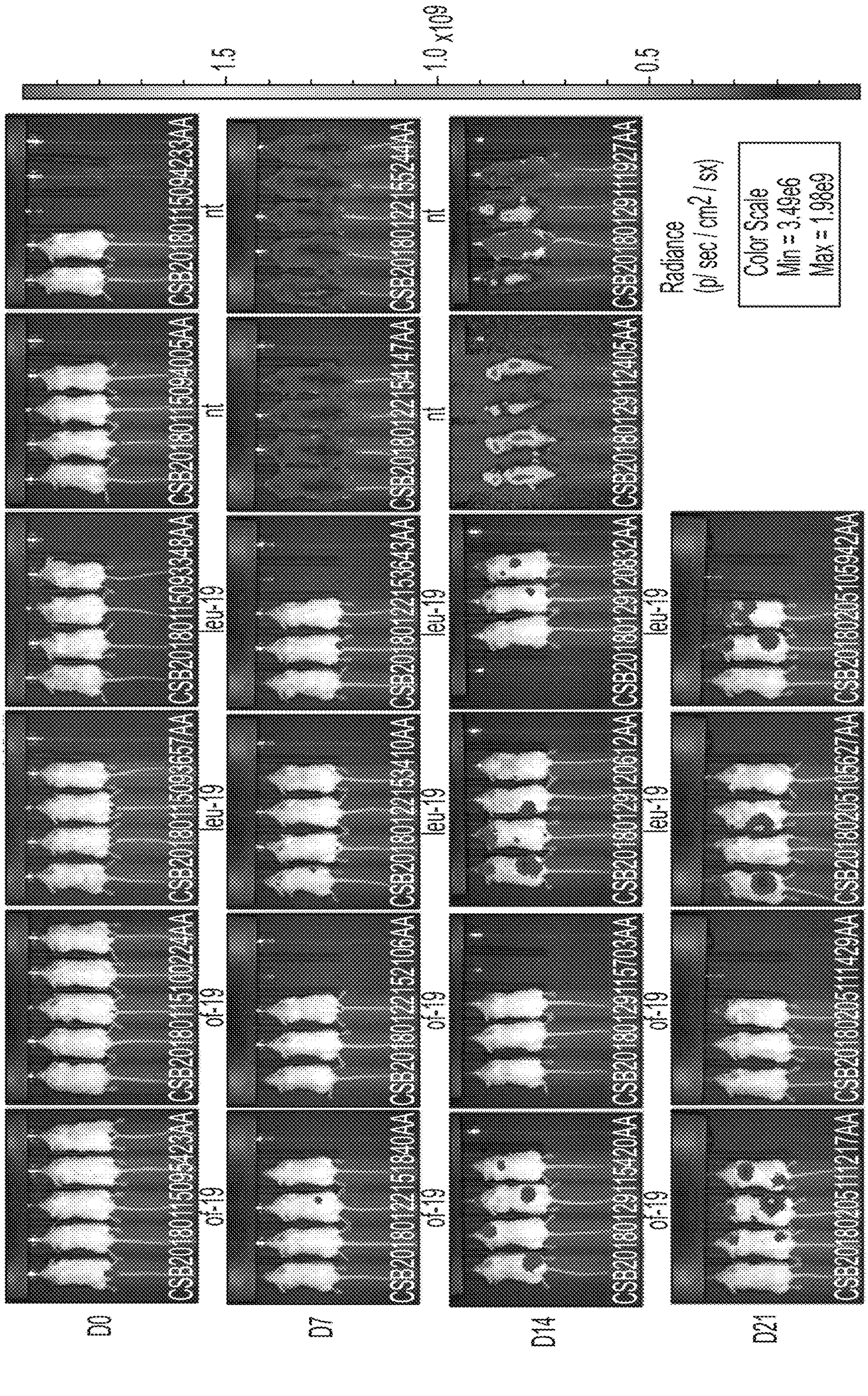

FIG. 6F shows the IVIS imaging of fluorescence intensity in mice. The results showed that after the injection of effector T cells in the tail vein, the fluorescence intensities of the mice in the two CART cell groups were very weak after the 7th day, while that of NT group was very strong. The situation on 14th day was the same. The mice in NT group had all died on the 21st day, while the mice in the two CART cell groups were still growing normally.

Example 8 Screening and Functional Verification of CAR-T20.1, CAR-T20.2 and CAR-T20.4

The construction and detection of CART cells were performed with reference to Examples 2, 3, 4, and 5.

First, full-length DNA was synthesized and cloned to achieve the construction of encoding plasmids. CAR-T 20.1, 20.2 and 20.4 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5\times10^6$ cells of CAR-T20s cell sample cultured 7 days were taken and detected for the cell transfection efficiency by DNA copy number.

Figure 7A:
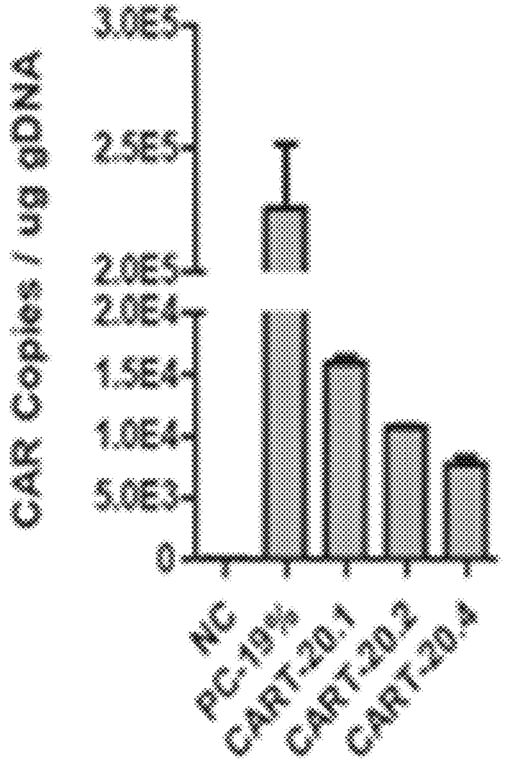
FIGS. 7A-7C show the preliminary functional verification results of CAR-T20.1, CAR-T20.2, and CAR-T20.4.

The results are shown in FIG. 7A. Compared to the positive control, the DNA copy number was not very high. Next, co-culture was performed, and CAR-T20s cells cultured for 7 days were used to detect the indicator proteins CD137 and IFNγ of the cell activation level.

$1\times10^5$ of CAR-T20 cells cultured for 7 days were taken and cultured respectively with CD20-positive cells Raji, Ramos and negative cells K562, Karpas tumor cell line for 18 h with a ratio of 1:1. Then the expression levels of CD137 on the surface of T cell membrane and the secretion levels of IFNγ in the culture supernatant were detected respectively.

Figure 7B:
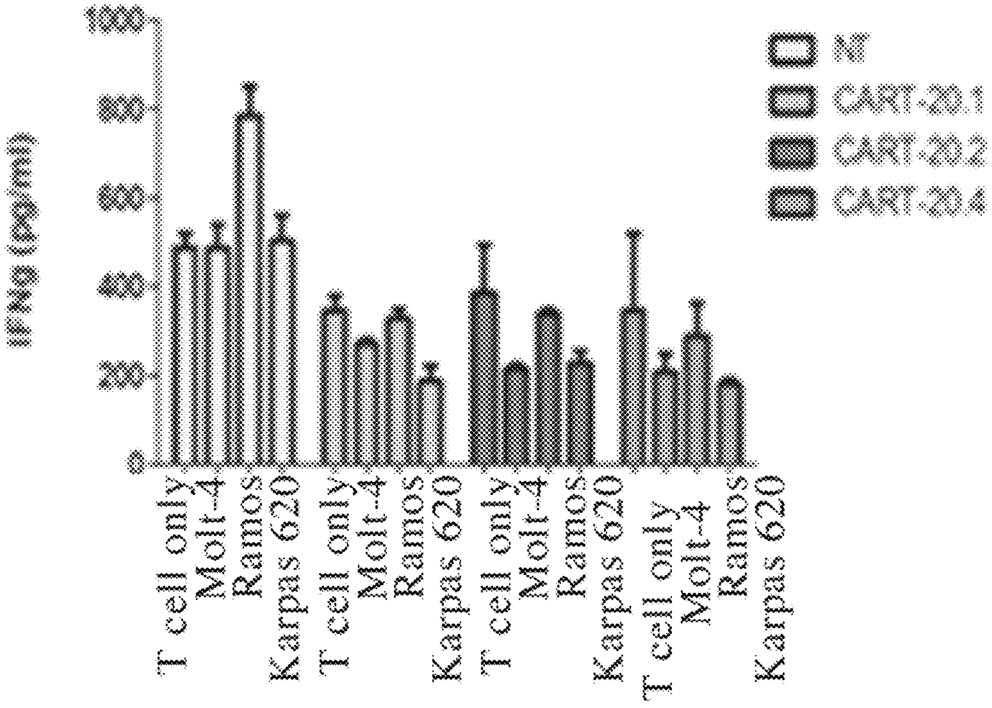
Figure 7C:
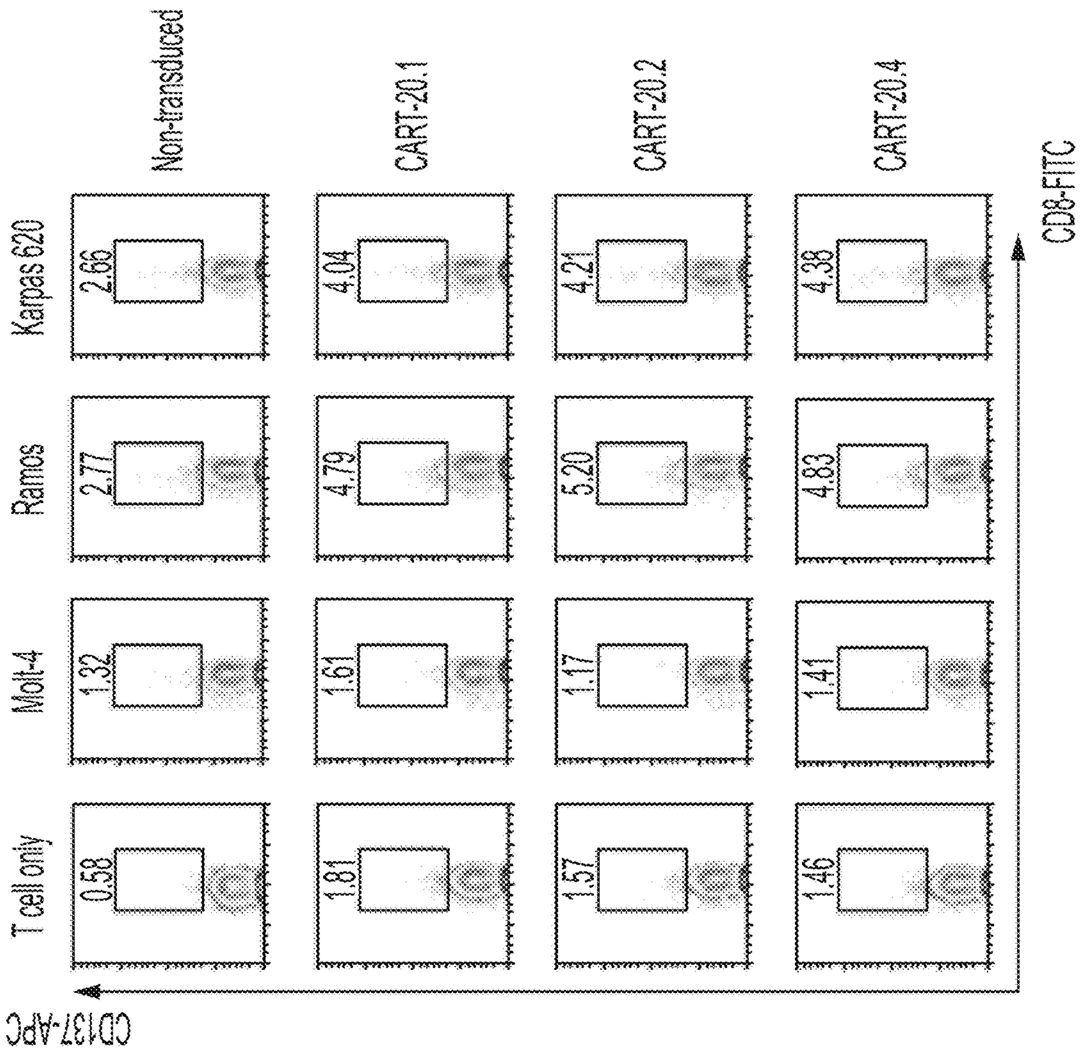

The results are shown in FIGS. 7B and 7C. CAR-T20.1, CAR-T20.2 and CAR-T20.4 constructed in this example are invalid.

Example 9 Screening and Functional Verification of CAR-T20.5, CAR-T20.6, CAR-T20.7, CAR-T20.8, CAR-T20.9 and CAR-T20.10

The construction and detection of CART cells were performed with reference to Examples 2, 3, 4, and 5.

First, full-length DNA was synthesized and cloned to achieve the construction of encoding plasmids. CAR-T20.5, CAR-T20.6, CAR-T20.7, CAR-T20.8, CAR-T20.9 and CAR-T20.10 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5\times10^6$ cells of CAR-T20s cell sample cultured 7 days were taken and detected for the T cell transfection efficiency. Protein L method was used to identify the expression level of CAR gene-encoded protein on the surface of T cell membrane in CAR-T20s cells cultured for 7 days.

Figure 8A:
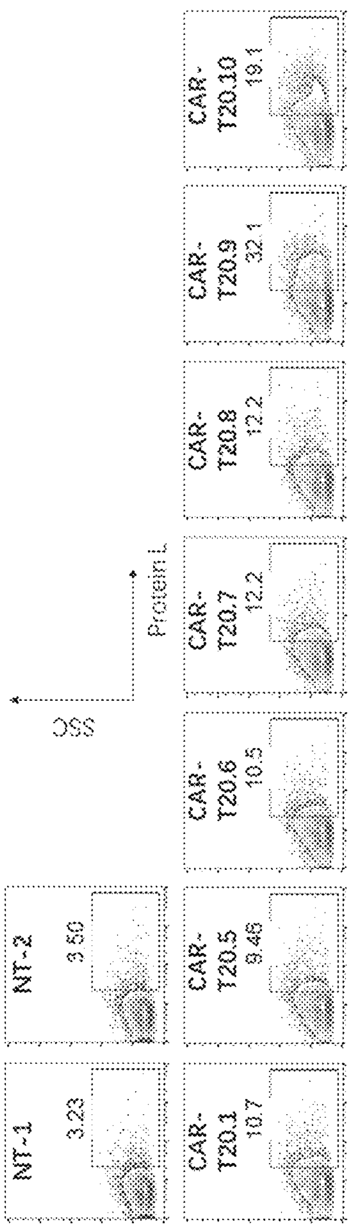
FIGS. 8A-8C show the functional verification results of CAR-T20.5, CAR-T20.6, CAR-T20.7, CAR-T20.8, CAR-T20.9 and CAR-T20.10.

The results are shown in FIG. 8A. Compared with CAR-T20.1, among CAR-T20.5, CAR-T20.6, CAR-T20.7, CAR-T20.8, CAR-T20.9 and CAR-T20.10, only CAR-T20.9 and CAR-T20.10 had a higher positive rate.

Next, co-culture was performed, and CAR-T20s cells cultured for 7 days were used to detect the indicator proteins CD137 and IFNγ of the cell activation level. $1\times10^6$ of CAR-T20s cells cultured for 7 days were cultured respectively with CD20-positive cells Raji, Ramos and negative cells K562, Karpas tumor cell line for 18 h with a ratio of 1:1. Then the expression levels of CD137 on the surface of T cell membrane and the secretion levels of IFNγ in the culture supernatant were detected respectively.

Figure 8B:
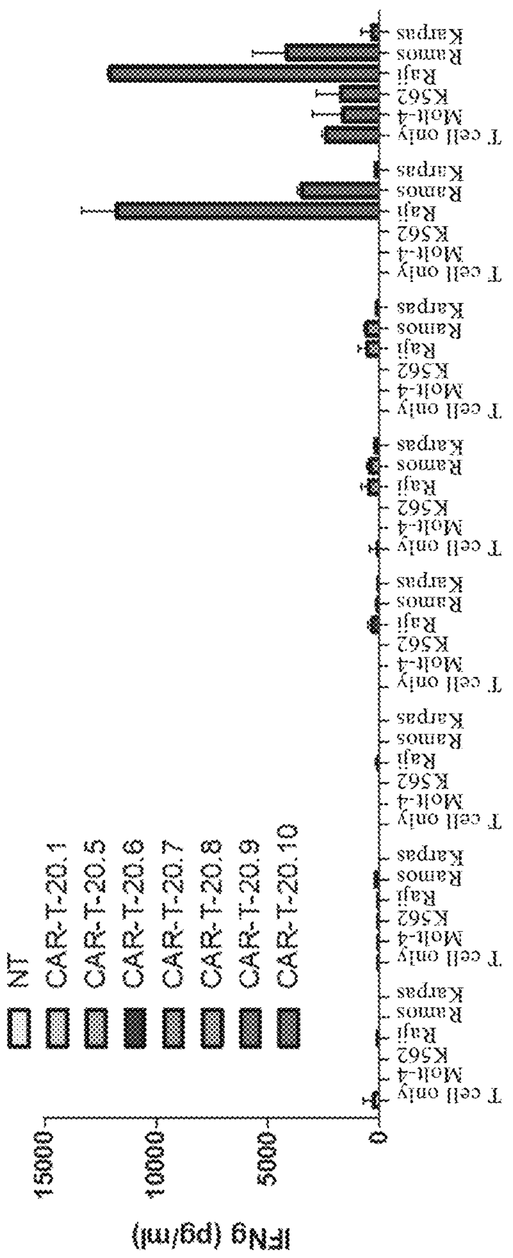
Figure 8C:
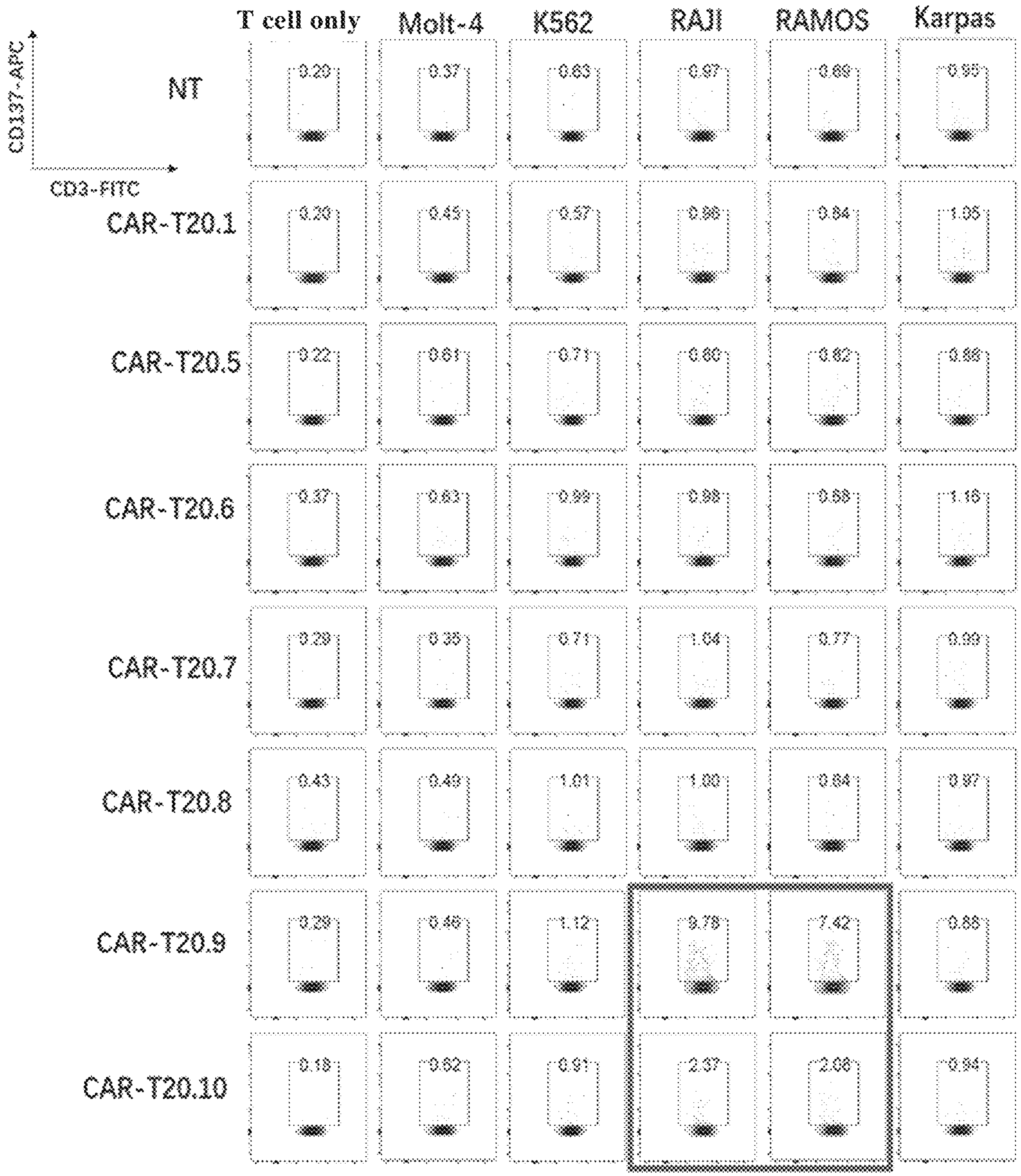

The results are shown in FIGS. 8B and 8C. The results show that among CAR-T20.5, CAR-T20.6, CAR-T20.7, CAR-T20.8, CAR-T20.9 and CAR-T20.10, only in CAR-T20.9 and CAR-T20.10, the expression levels of CD137 on the surface of T cell membrane were activated and IFNγ was released in the culture supernatant. That is, CAR-T20.9 and CAR-T20.10 are effective.

Example 10 Screening and Functional Verification of CAR-T20.11, CAR-T20.12, CAR-T20.13, CAR-T20.14, CAR-T20.15 and CAR-T20.16

The construction and detection of CART cells were performed with reference to Examples 2, 3, 4, and 5.

First, full-length DNA was synthesized and cloned to achieve the construction of encoding plasmids. CAR-T20.11, CAR-T20.12, CAR-T20.13, CAR-T20.14, CAR-T20.15 and CAR-T20.16 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5\times10^6$ of CAR-T20s cells sample cultured for 7 days were taken and detected for the T cell transfection efficiency. Protein L method was used to identify the expression level of CAR gene-encoded protein on the surface of T cell membrane in CAR-T20s cells cultured for 7 days.

Figure 9A:
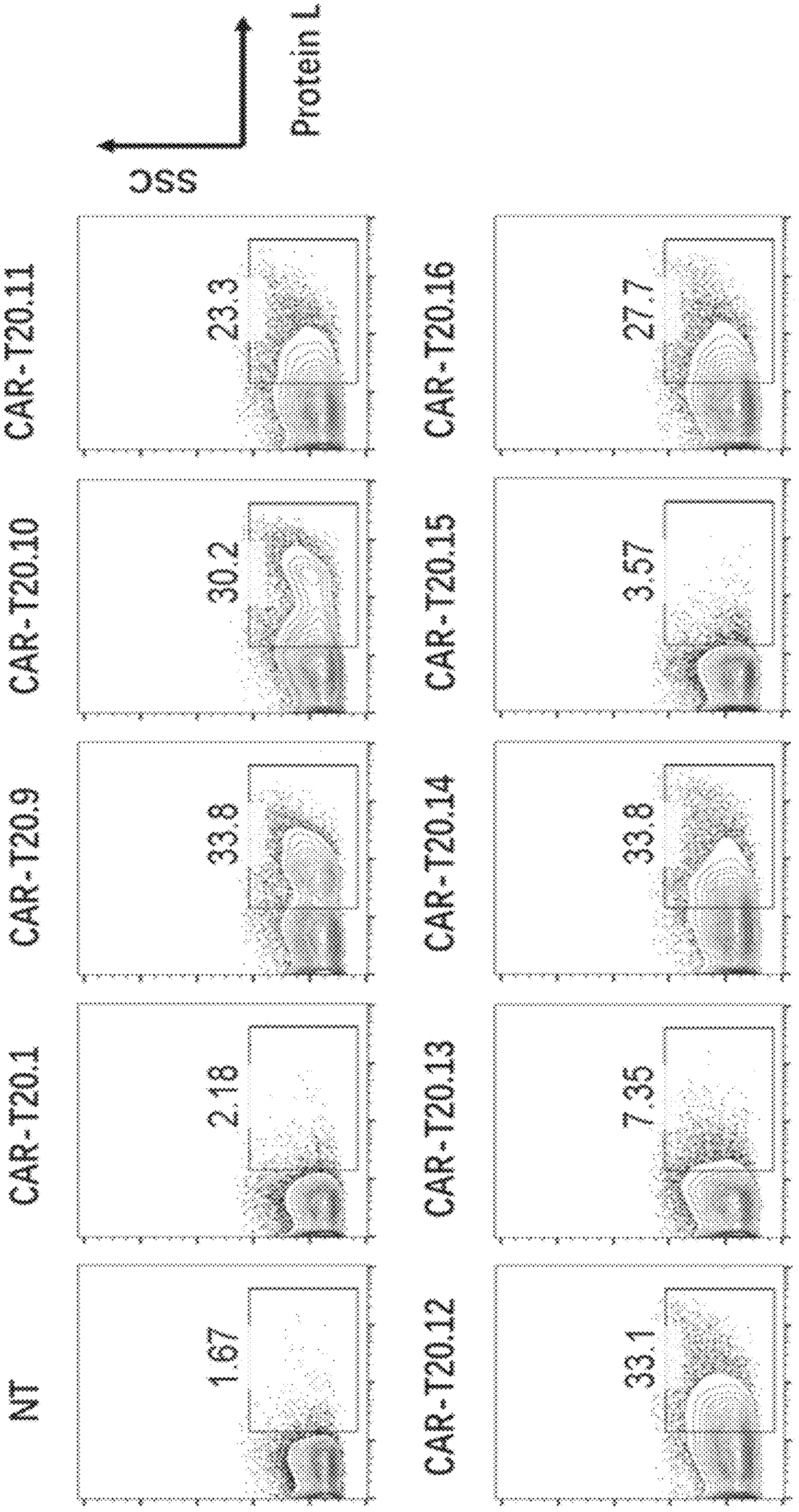
FIGS. 9A-9C show the functional verification results of CAR-T20.11, CAR-T20.12, CAR-T20.13, CAR-T20.14, CAR-T20.15 and CAR-T20.16.

The results are shown in FIG. 9A. Compared with CAR-T20.1, CAR-T20.9 and CAR-T20.10, the positive rates of CAR-T20.11, CAR-T20.12, CAR-T20.14 and CAR-T20.16 were high, while the positive rates of CAR-T20.13 and CAR-T20.15 were very low.

Next, co-culture was performed, and CAR-T20s cells cultured for 7 days were used to detect the indicator proteins CD137 and IFNγ of the cell activation level. $1\times10^6$ of CAR-T20s cells cultured for 7 days were cultured respectively with CD20-positive cells Raji, Ramos and negative cells K562, Molt-4 tumor cell line for 18 h with a ratio of 1:1. Then the expression level of CD137 on the surface of T cell membrane and the secretion level of IFNγ in the culture supernatant were detected respectively.

Figure 9B:
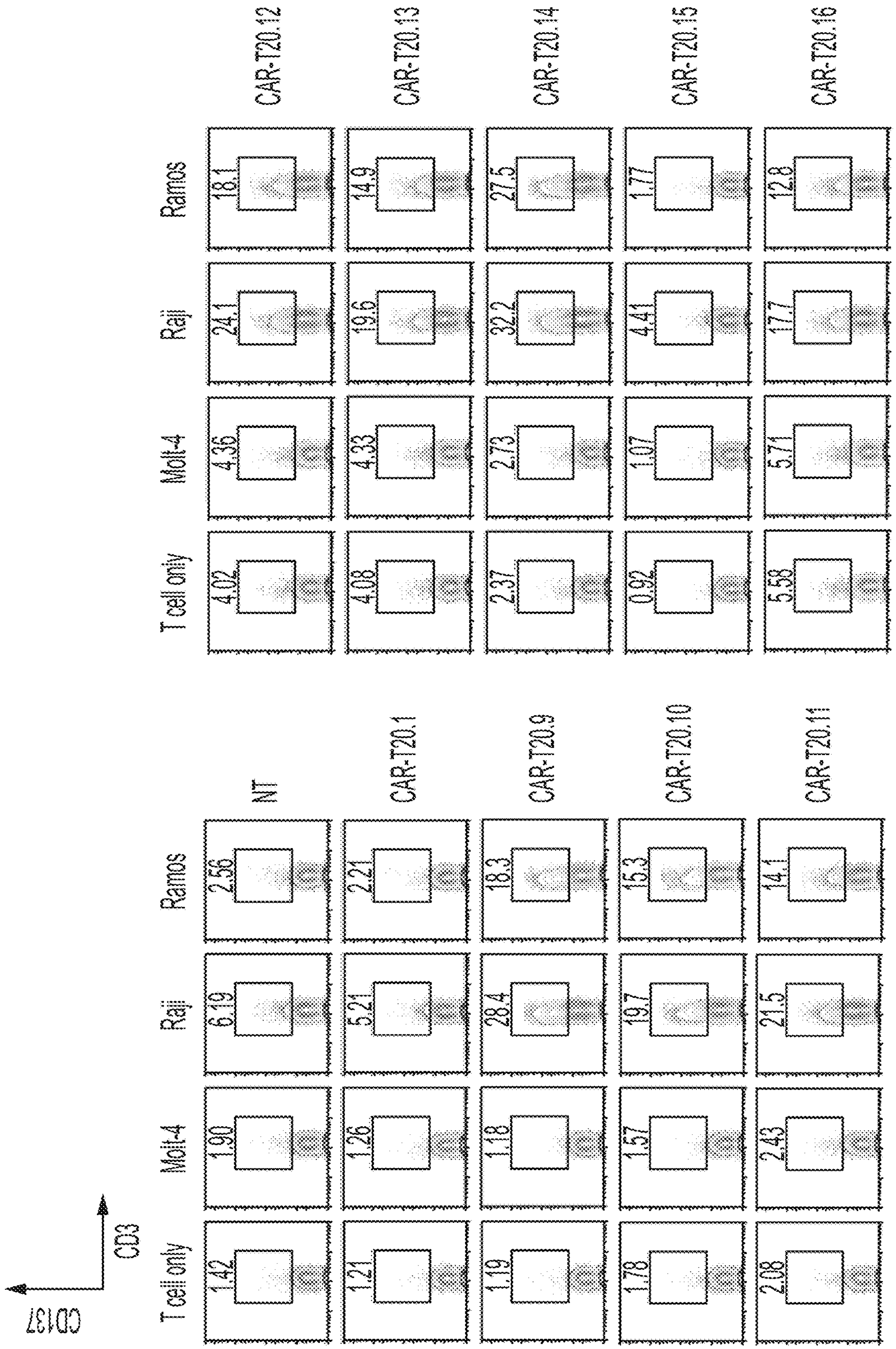
Figure 9C:
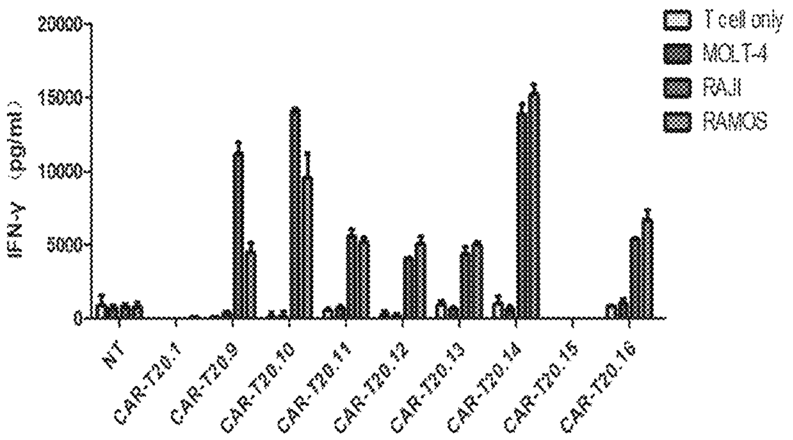

The results are shown in FIGS. 9B and 9C. The results show that after co-culture with CD20-positive Raji and Ramos, the expression levels of CD137 on the surface of T cell membranes in CAR-T20.9, CAR-T20.10, CAR-T20.11, CAR-T20.12, CAR-T20. 13, CAR-T20.14 and CAR-T20.16 were activated, and the releases were high, wherein CAR-T20.10 and CAR-T20.14 were the highest, followed by the rest, only CAR-T20.15 showed no response. Correspondingly, the releases of IFNγ in the culture supernatant were the same. The results showed that CAR-T20.10 and CAR-T20.14 had the best activity in this screening.

Example 11 Screening and Functional Verification of CAR-T20.17, CAR-T20.18 and CAR-T20.19

The construction and detection of CART cells were performed with reference to Examples 2, 3, 4, and 5.

First, full-length DNA was synthesized and cloned to achieve the construction of encoding plasmids. CAR-T20.17, CAR-T20.18 and CAR-T20.19 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5\times10^6$ cells of CAR-T20s cell sample cultured for 7 days were taken and detected for the T cell transfection efficiency. Protein L method was used to identify the expression level of CAR gene-encoded protein on the surface of T cell membrane in CAR-T20s cells cultured for 7 days.

Figure 10A:
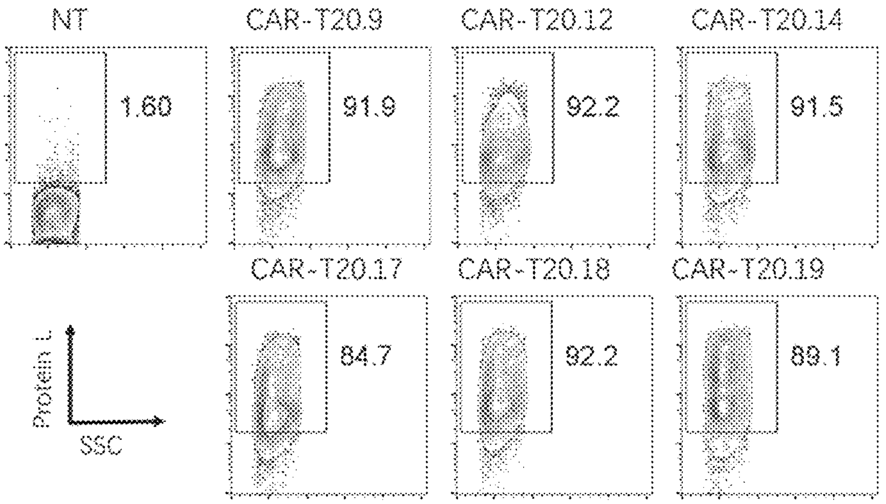
FIGS. 10A-10D show the functional verification results of CAR-T20.17, CAR-T20.18 and CAR-T20.19.

The results are shown in FIG. 10A. Compared with CAR-T20.9, CAR-T20.12 and CAR-T20.14, the positive rates of CAR-T20.17, CAR-T20.18 and CAR-T20.19 were higher, and the expressions thereof were well.

Next, co-culture was performed, and CAR-T20s cells cultured for 7 days were used to detect the indicator proteins CD137 and IFNγ of the cell activation level. $1\times10^6$ of CAR-T20s cells cultured for 7 days were cultured respectively with CD20-positive cells Raji, Ramos and negative cells Karpas-620, Molt-4 tumor cell line for 18 h with a ratio of 1:1. Then the expression levels of CD137 on the surface of T cell membrane and the secretion levels of IFNγ in the culture supernatant were detected respectively.

Figure 10B:
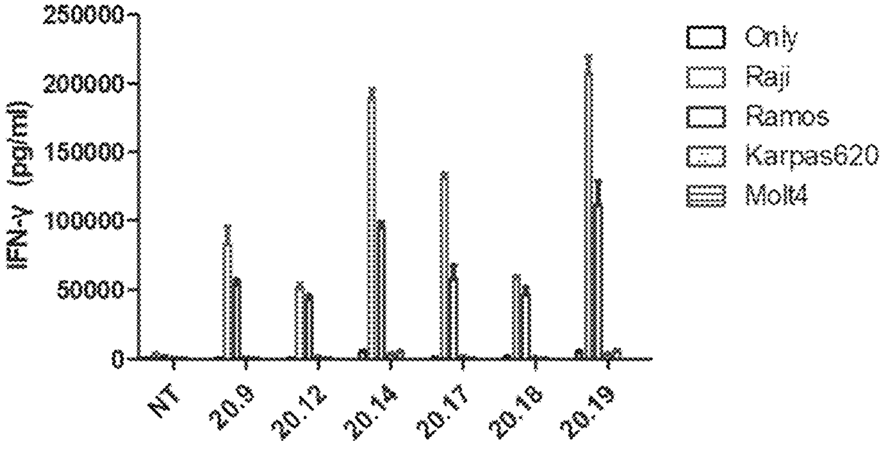
Figure 10C:
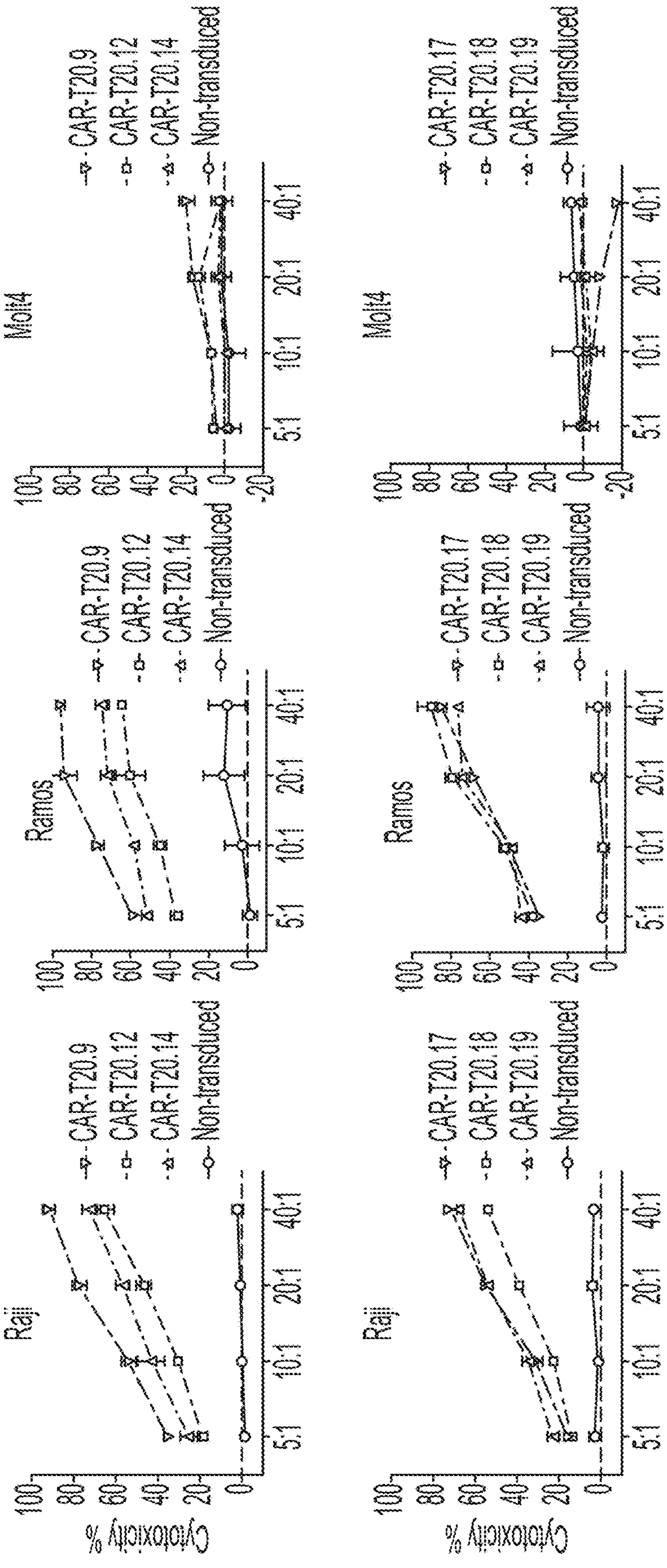
Figure 10D:
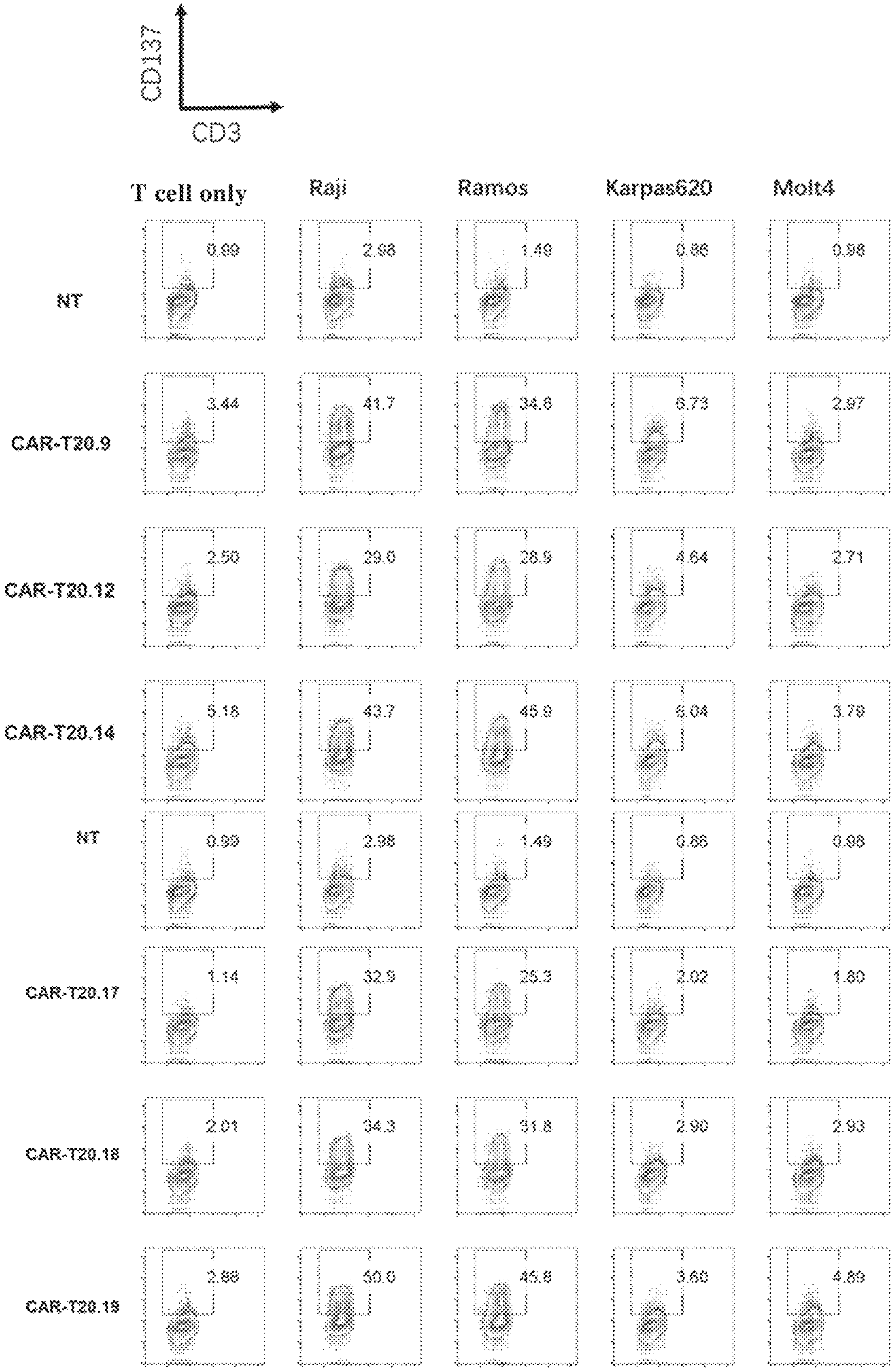

The results are shown in FIGS. 10B and 10D. After co-culture with CD20-positive Raji, Ramos, the expression levels of CD137 on the surface of T cell membrane in CAR-T20.17, CAR-T20.18 and CAR-T20.19 were activated and released very high. Correspondingly, the releases of IFNγ in the culture supernatant were the same, wherein the releases of CAR-T20.17, CAR-T20.18 and CAR-T20.19 were very high. Subsequently, the detection of LDH levels released by CAR-T20s cells for killing targeted tumors in vitro was performed. Specific experimental methods can be referred to Example 5.

Target cells comprise CD20-positive Raji, Romas, and CD20-negative Molt4. The final killing results showed that CAR-T20.17, CAR-T20.18, and CAR-T20.19 had strong killing effects on target cells CD20-positive Raji and Romas.

The results of Examples 8-11 are summarized as follows:

The applicant of the present invention conducted a large number of experiments and screened out multiple CARs with good effects. Through comparison, it was found that 20.1, 20.2, 20.4, 20.5, 20.6, 20.7, 20.8 and 20.15 were basically invalid, and 20.11, 20.12 and 20.13 had certain effects, but the effects of them were less than that of 20.9, 20.10, 20.14, 20.16, 20.17, 20.18 and 20.19, wherein the effects of 20.18 and 20.19 were the best. Based on the above structures, CD20 Scfv and CD19 scFv (FMC63) were tandemly used in a new bispecific chimeric antigen receptor.

The structures of the chimeric antigen receptor in the CART cells involved in Examples 8-11 are shown in Table 1 below, and the sequences are shown in Table 2 below.

TABLE 1

| Chimeric antigen receptors and structures thereof | |
|---|---|
| Change of CAR-T | Structure |
| CAR-T20.1 | [CD8LS]-CD20 (AY16076.1) [VL-Linker-VH]-[hinge-CD8DE]-[4-1BB]-[CD3zeta] |
| CAR-T20.5 | [CD8LS]-CD20 (AY16076.1) [VL-Linker-VH]-[hinge-CD8TM]-[4-1BB]-[CD3zeta] |
| CAR-T20.6 | [CD8LS]-CD20 (AY16076.1) [VH-Linker-VL]-[hinge-CD8TM]-[4-1BB]-[CD3zeta] |
| CAR-T20.7 | [CD8LS]-CD20 (IDEC-C2B8) [VL-Linker-VH]-[hinge-CD8TM]-[4-1BB]-[CD3zeta] |
| CAR-T20.8 | [CD8LS]-CD20 (IDEC-C2B8) [VL-Linker-VH]-[hinge-CD8TM]-[4-1BB]-[CD3zeta] |
| CAR-T20.9 | [CD8LS]-LEU16 [VH-Linker-VL]-[hinge-CH2-CH3-CD28TM]-[CD28]-[4-1BB]-[CD3zeta] |
| CAR-720.10 | [CD8LS]-LEU16 [VL-Linker-VH]-[hinge-CH2-CH3-CD28TM]-[CD28]-[4-1BB]-[CD3zeta] |
| CAR-720.11 | [CD8LS]-LEU16 [VL-Linker-VH]-[hinge-CH2-CH3-CD8TM]-[4-1BB]-[CD3zeta] |
| CAR-720.12 | [CD8LS]-LEU16 [VH-Linker-VL]-[hinge-CH2-CH3-CD8TM]-[4-1BB]-[CD3zeta] |
| CAR-720.13 | [CD8LS]-Obinutuzumab [VH-Linker-VL]-[hinge-CH2-CH3-CD8TM]-[4-1BB]-[CD3zeta] |
| CAR-720.14 | [CD8LS]-Ofatuzumab [VH-Linker-VL]-[hinge-CH2-CH3-CD8TM]-[4-1BB]-[CD3zeta] |
| CAR-720.15 | [CD8LS]-CD20 (AY16076.1) [VH-Linker-VL]-[hinge-CH2-CH3-CD8TM]-[4-1BB]-[CD3zeta] |
| CAR-720.16 | [CD8LS]-Rituximab [VH-Linker-VL]-[hinge-CH2-CH3-CD8TM]-[4-1BB]-[CD3zeta] |
| CAR-720.17 | [CD8LS]-LEU16 [VH-Linker-VL]-[hinge-CH2-CH3-CD28TM]-[CD28]-[4-1BB]-[CD3zeta] (L235E N297Q) |
| CAR-720.18 | [CD8LS]-LEU16 [VH-Linker-VL]-[hinge-CH2-CH3-CD8TM]-[4-1BB]-[CD3zeta] (L235E N297Q) |
| CAR-T20.19 | [CD8LS]-Ofatuzumab [VH-Linker-VL]-[hinge-CH2-CH3-CD8TM]-[4-1BB]-[CD3zeta] (L235E N297Q) |

TABLE 2

| Chimeric antigen receptors and sequences thereof | | |
|---|---|---|
| CAR-T | Sequence | SEQ ID NO. |
| CAR-T20.1 | MDIQLTQSPAILSASPGEKVTMTCRASSSLSFMHWYQQKPGS<br>SPKPWIYATSNLASGVPARFSGSGSGTSYSLTISTVEAEDAAS<br>YFCHQWSSNPLTFGAGTKLEISSGGGGSGGGGSGDVMGVDS<br>GGGLVQPGGSRKLSCAAPGFTFSSFGMHWVRQAPEKGLEW<br>VAYISSPSSTLHYADRVKGRFTISRDNPKNTLFLQMKLPSLCY<br>GLLGPRDHVHRLLKTRLSNSIMYFSHFVPVFLPAKPTTTPAPR<br>PPTPAPTIASQPLSLRPEACRPAAGGAVHTRGLDFACDIYIWA<br>PLAGTCGVLLLSLVITLYCRSKRGRKKLLYIFKQPFMRPVQTT<br>QEEDGCSCRFPEEEEGGCELEFRVKFSRSADAPAYQQGQNQL<br>YNELNLGRREEYDVLDKRRGRDPEMGGKPRRKNPQEGLYN<br>ELQKDKMAEAYSEIGMKGERRRGKGHDGLYQGLSTATKDT<br>YDALHMQALPPR | 23 |
| CAR-T20.4 | MALPVTALLLPLALLLHAARPDIQLTQSPAILSASPGEKVTMT<br>CRASSSLSFMHWYQQKPGSSPKPWIYATSNLASGVPARFSGS<br>GSGTSYSLTISTVEAEDAASYFCHQWSSNPLTFGAGTKLEISS<br>GGGGSGGGGSGDVMGVDSGGGLVQPGGSRKLSCAAPGFTF<br>SSFGMHWVRQAPEKGLEWVAYISSPSSTLHYADRVKGRFTIS<br>RDNPKNTLFLQMKLPSLCYGLLGPRDHVHRLLKTRLSNSIMY<br>FSHFVPVFLPAKPTTTPAPRPPTPAPTIASQPLSLRPEACRPAA<br>GGAVHTRGLDFACDIYIWAPLAGTCGVLLLSLVITLYCRSKR<br>GRKKLLYIFKQPFMRPVQTTQEEDGCSCRFPEEEEGGCELEF<br>RVKFSRSADAPAYQQGQNQLYNELNLGRREEYDVLDKRRG<br>RDPEMGGKPRRKNPQEGLYNELQKDKMAEAYSEIGMKGER<br>RRGKGHDGLYQGLSTATKDTYDALHMQALPPR | 24 |
| CAR-T20.5 | MALPVTALLLPLALLLHAARPDIQLTQSPAILSASPGEKVTMT<br>CRASSSLSFMHWYQQKPGSSPKPWIYATSNLASGVPARFSGS<br>GSGTSYSLTISTVEAEDAASYFCHQWSSNPLTFGAGTKLEIGG<br>GGSGGGGSGGGGSDVMGVDSGGGLVQPGGSRKLSCAAPGF<br>TFSSFGMHWVRQAPEKGLEWVAYISSPSSTLHYADRVKGRF<br>TISRDNPKNTLFLQMKLPSLCYGLLGPRDHVHRLLTRTTTPA<br>PRPPTPAPTIASQPLSLRPEACRPAAGGAVHTRGLDFACDIYI<br>WAPLAGTCGVLLLSLVITLYCRSKRGRKKLLYIFKQPFMRPV<br>QTTQEEDGCSCRFPEEEEGGCELEFELGTFKTNDLQGSCRS | 25 |
| CAR-T20.6 | MALPVTALLLPLALLLHAARPDVMGVDSGGGLVQPGGSRKL<br>SCAAPGFTFSSFGMHWVRQAPEKGLEWVAYISSPSSTLHYAD<br>RVKGRFTISRDNPKNTLFLQMKLPSLCYGLLGPRDHVHRLLG<br>GGGSGGGGSGGGGSDIQLTQSPAILSASPGEKVTMTCRASSS<br>LSFMHWYQQKPGSSPKPWIYATSNLASGVPARFSGSGSGTSY<br>SLTISTVEAEDAASYFCHQWSSNPLTFGAGTKLEITRTTTPAP<br>RPPTPAPTIASQPLSLRPEACRPAAGGAVHTRGLDFACDIYIW<br>APLAGTCGVLLLSLVITLYCRSKRGRKKLLYIFKQPFMRPVQ<br>TTQEEDGCSCRFPEEEEGGCELEFELGTFKTNDLQGSCRS | 26 |

TABLE 2 -continued

Chimeric antigen receptors and sequences thereof

| CAR-T | Sequence | SEQ ID NO. |
|---|---|---|
| CAR-T20.7 | MALPVTALLLPLALLLHAARPQIVLSQSPAILSASPGEKVTMT CRASSSVSYIHWFQQKPGSSPKPWIYATSNLASGVPVRFSGS GSGTSYSLTISRVEAEDAATYYCQQWTSNPPTFGGGTKLEIK GGGGSGGGGSGGGGSQVQLQQPGAELVKPGASVKMSCKAS GYTFTSYNMHWVKQTPGRGLEWIGAIYPGNGDTSYNQKFK GKATLTADKSSSTAYMQLSSLTSEDSAVYYCARSTYYGGDW YFNVWGAGTTVTVSATRTTTPAPRPPTPAPTIASQPLSLRPEA CRPAAGGAVHTRGLDFACDIYIWAPLAGTCGVLLLSLVITLY CRSKRGRKKLLYIFKQPFMRPVQTTQEEDGCSCRFPEEEEGG CELEFELGTFKTNDLQGSCRS | 27 |
| CAR-T20.8 | MALPVTALLLPLALLLHAARPQVQLQQPGAELVKPGASVKM SCKASGYTFTSYNMHWVKQTPGRGLEWIGAIYPGNGDTSYN QKFKGKATLTADKSSSTAYMQLSSLTSEDSAVYYCARSTYY GGDWYFNVWGAGTTVTVSAGGGGSGGGGSGGGGSQIVLSQ SPAILSASPGEKVTMTCRASSSVSYIHWFQQKPGSSPKPWIYA TSNLASGVPVRFSGSGSGTSYSLTISRVEAEDAATYYCQQWT SNPPTFGGGTKLEIKTRTTTPAPRPPTPAPTIASQPLSLRPEAC RPAAGGAVHTRGLDFACDIYIWAPLAGTCGVLLLSLVITLYC RSKRGRKKLLYIFKQPFMRPVQTTQEEDGCSCRFPEEEEGGC ELEFELGTFKTNDLQGSCRS | 28 |
| CAR-T20.9 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFLGGPSVFLFPPK PKDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKFWVLV VVGGVLACYSLLVTVAFIIFWVRSKRSRLLHSDYMNMTPRR PGPTRKHYQPYAPPRDFAAYRSKRGRKKLLYIFKQPFMRPVQ TTQEEDGCSCRFPEEEEGGCELRVKFSRSADAPAYKQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 29 |
| CAR-T20.10 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFLGGPSVFLFPPK PKDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKFWVLV VVGGVLACYSLLVTVAFIIFWVRSKRSRLLHSDYMNMTPRR PGPTRKHYQPYAPPRDFAAYRSKRGRKKLLYIFKQPFMRPVQ TTQEEDGCSCRFPEEEEGGCELRVKFSRSADAPAYKQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 30 |
| CAR-T20.11 | MALPVTALLLPLALLLHAARPDIVLTQSPAILSASPGEKVTMT CRASSSVNYMDWYQKKPGSSPKPWIYATSNLASGVPARFSG SGSGTSYSLTISRVEAEDAATYYCQQWSFNPPTFGGGTKLEIK GGGGSGGGGSGGGGSEVQLQQSGAELVKPGASVKMSCKAS GYTFTSYNMHWVKQTPGQGLEWIGAIYPGNGDTSYNQKFK GKATLTADKSSSTAYMQLSSLTSEDSADYYCARSNYYGSSY WFFDVWGAGTTVTVSSESKYGPPCPPCPAPEFLGGPSVFLFPP KPKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLGKIYIWA PLAGTCGVLLLSLVITLYCKRGRKKLLYIFKQPFMRPVQTTQ | 31 |

TABLE 2 -continued

Chimeric antigen receptors and sequences thereof

| CAR-T | Sequence | SEQ ID NO. |
|---|---|---|
| | EEDGCSCRFPEEEEGGCELRVKFSRSADAPAYKQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR | |
| CAR-T20.12 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFLGGPSVFLFPPK PKDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKIYIWAP LAGTCGVLLLSLVITLYCKRGRKKLLYIFKQPFMRPVQTTQE EDGCSCRFPEEEEGGCELRVKFSRSADAPAYKQGQNQLYNE LNLGRREEYDVLDKRRGRDPEMGGKPRRKNPQEGLYNELQ KDKMAEAYSEIGMKGERRRGKGHDGLYQGLSTATKDTYDA LHMQALPPR | 32 |
| CAR-T20.13 | MALPVTALLLPLALLLHAARPQVQLVQSGAEVKKPGSSVKV SCKASGYAFSYSWINWVRQAPGQGLEWMGRIFPGDGDTDY NGKFKGRVTITADKSTSTAYMELSSLRSEDTAVYYCARNVF DGYWLVYWGQGTLVTVSSGGGGSGGGGSGGGGSDIVMTQT PLSLPVTPGEPASISCRSSKSLLHSNGITYLYWYLQKPGQSPQ LLIYQMSNLVSGVPDRFSGSGSGTDFTLKISRVEAEDVGVYY CAQNLELPYTFGGGTKVEIKRTVESKYGPPCPPCPAPEFLGGP SVFLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTKNQ VSLTCLVKGFYPSDIAVEWESNGQPENNYKTTPPVLDSDGSF FLYSRLTVDKSRWQEGNVFSCSVMHEALHNHYTQKSLSLSL GKIYIWAPLAGTCGVLLLSLVITLYCKRGRKKLLYIFKQPFM RPVQTTQEEDGCSCRFPEEEEGGCELRVKFSRSADAPAYKQG QNQLYNELNLGRREEYDVLDKRRGRDPEMGGKPRRKNPQE GLYNELQKDKMAEAYSEIGMKGERRRGKGHDGLYQGLSTA TKDTYDALHMQALPPR | 33 |
| CAR-T20.14 | MALPVTALLLPLALLLHAARPEVQLVESGGGLVQPGRSLRLS CAASGFTFNDYAMHWVRQAPGKGLEWVSTISWNSGSIGYA DSVKGRFTISRDNAKKSLYLQMNSLRAEDTALYYCAKDIQY GNYYYGMDVWGQGTTVTVSSGGGGSGGGGSGGGGSEIVLT QSPATLSLSPGERATLSCRASQSVSSYLAWYQQKPGQAPRLL IYDASNRATGIPARFSGSGSGTDFTLTISSLEPEDFAVYYCQQ RSNWPITFGQGTRLEIKESKYGPPCPPCPAPEFLGGPSVFLFPP KPKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLGKIYIWA PLAGTCGVLLLSLVITLYCKRGRKKLLYIFKQPFMRPVQTTQ EEDGCSCRFPEEEEGGCELRVKFSRSADAPAYKQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR | 34 |
| CAR-T20.15 | MALPVTALLLPLALLLHAARPGDVMGVDSGGGLVQPGGSR KLSCAAPGFTFSSFGMHWVRQAPEKGLEWVAYISSPSSTLHY ADRVKGRFTISRDNPKNTLFLQMKLPSLCYGLLGPRDHVHRL LKGGGGSGGGGSGGGGSDIQLTQSPAILSASPGEKVTMTCRA SSSLSFMHWYQQKPGSSPKPWIYATSNLASGVPARFSGSGSG TSYSLTISTVEAEDAASYFCHQWSSNPLTFGAGTKLEIESKYG PPCPPCPAPEFLGGPSVFLFPPKPKDTLMISRTPEVTCVVVDVS QEDPEVQFNWYVDGVEVHNAKTKPREEQFNSTYRVVSVLT VLHQDWLNGKEYKCKVSNKGLPSSIEKTISKAKGQPREPQV YTLPPSQEEMTKNQVSLTCLVKGFYPSDIAVEWESNGQPENN YKTTPPVLDSDGSFFLYSRLTVDKSRWQEGNVFSCSVMHEA LHNHYTQKSLSLSLGKIYIWAPLAGTCGVLLLSLVITLYCKR | 35 |

TABLE 2 -continued

Chimeric antigen receptors and sequences thereof

| CAR-T | Sequence | SEQ ID NO. |
|---|---|---|
| | GRKKLLYIFKQPFMRPVQTTQEEDGCSCRFPEEEEGGCELRV KFSRSADAPAYKQGQNQLYNELNLGRREEYDVLDKRRGRD PEMGGKPRRKNPQEGLYNELQKDKMAEAYSEIGMKGERRR GKGHDGLYQGLSTATKDTYDALHMQALPPR | |
| CAR-T20.16 | MALPVTALLLPLALLLHAARPQVQLQQPGAELVKPGASVKM SCKASGYTFTSYNMHWVKQTPGRGLEWIGAIYPGNGDTSYN QKFKGKATLTADKSSSTAYMQLSSLTSEDSAVYYCARSTYY GGDWYFNVWGAGTTVTVSAGGGGSGGGGSGGGGSQIVLSQ SPAILSASPGEKVTMTCRASSSVSYIHWFQQKPGSSPKPWIYA TSNLASGVPVRFSGSGSGTSYSLTISRVEAEDAATYYCQQWT SNPPTFGGGTKLEIKESKYGPPCPPCPAPEFLGGPSVFLFPPKP KDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKIYIWAP LAGTCGVLLLSLVITLYCKRGRKKLLYIFKQPFMRPVQTTQE EDGCSCRFPEEEEGGCELRVKFSRSADAPAYKQGQNQLYNE LNLGRREEYDVLDKRRGRDPEMGGKPRRKNPQEGLYNELQ KDKMAEAYSEIGMKGERRRGKGHDGLYQGLSTATKDTYDA LHMQALPPR | 36 |
| CAR-T20.17 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFEGGPSVFLFPPK PKDTLMISRTPEVTCVVVDVSQEDPEVQFNWYVDGVEVHNA KTKPREEQFQSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKFWVLV VVGGVLACYSLLVTVAFIIFWVRSKRSRLLHSDYMNMTPRR PGPTRKHYQPYAPPRDFAAYRSKRGRKKLLYIFKQPFMRPVQ TTQEEDGCSCRFPEEEEGGCELRVKFSRSADAPAYKQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 37 |
| CAR-T20.18 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFEGGPSVFLFPPK PKDTLMISRTPEVTCVVVDVSQEDPEVQFNWYVDGVEVHNA KTKPREEQFQSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKIYIWAP LAGTCGVLLLSLVITLYCKRGRKKLLYIFKQPFMRPVQTTQE EDGCSCRFPEEEEGGCELRVKFSRSADAPAYKQGQNQLYNE LNLGRREEYDVLDKRRGRDPEMGGKPRRKNPQEGLYNELQ KDKMAEAYSEIGMKGERRRGKGHDGLYQGLSTATKDTY | 38 |
| CAR-T20.19 | MALPVTALLLPLALLLHAARPEVQLVESGGGLVQPGRSLRLS CAASGFTFNDYAMHWVRQAPGKGLEWVSTISWNSGSIGYA DSVKGRFTISRDNAKKSLYLQMNSLRAEDTALYYCAKDIQY GNYYYGMDVWGQGTTVTVSSGGGGSGGGGSGGGGSEIVLT QSPATLSLSPGERATLSCRASQSVSSYLAWYQQKPGQAPRLL IYDASNRATGIPARFSGSGSGTDFTLTISSLEPEDFAVYYCQQ RSNWPITFGQGTRLEIKESKYGPPCPPCPAPEFEGGPSVFLFPP KPKDTLMISRTPEVTCVVVDVSQEDPEVQFNWYVDGVEVHN AKTKPREEQFQSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLGKIYIWA | 39 |

TABLE 2 -continued

| Chimeric antigen receptors and sequences thereof | | |
|---|---|---|
| CAR-T | Sequence | SEQ ID NO. |
| | PLAGTCGVLLLSLVITLYCKRGRKKLLYIFKQPFMRPVQTTQ EEDGCSCRFPEEEEGGCELRVKFSRSADAPAYKQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR | |

Example 12 In Vivo Experiments in Mice of CART-TN-OF-19 and CART-TN-LEU-19

The inhibitory effects of CART-TN-OF-19 and CART-TN-LEU-19 cells on transplanted tumor cells in mice was tested. The detection method was performed with reference to Example 7, and the control group was NT.

Figure 11:
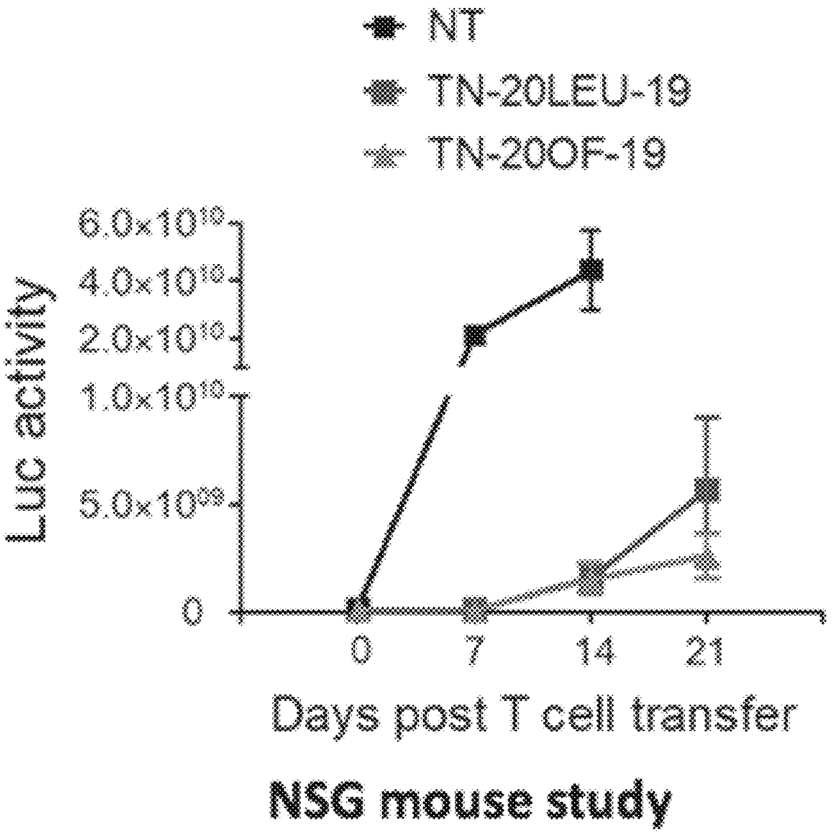
FIG. 11 shows the inhibitory effect of CAR-T19/20s cells on transplanted tumor cells in mice.

The results are shown in FIG. 11. Both CART cells can inhibit tumor cell expansion well. The fluorescence intensities of mice in the CART cell groups were very weak, while that of the NT group was very strong. Wherein, CART-TN-OF-19 can inhibit or kill tumor cells better than CART-TN-LEU-19 in vivo.

Example 13 Phase I Clinical Trial of CART-TN-OF-19

After approval by the ethics committee, a total of 3 volunteers (numbers C001, C002, and C003) were conducted in Phase I clinical trials. The key criteria for volunteer selection are as follows: the age should be 18-75 years, having received more than 2 DLBCL treatment, PD after or ineligible for auto-SCT, having not received anti-CD19 therapy, having no active CNS, and having sufficient liver, kidney, heart, and hematopoietic functions.

Figure 12:
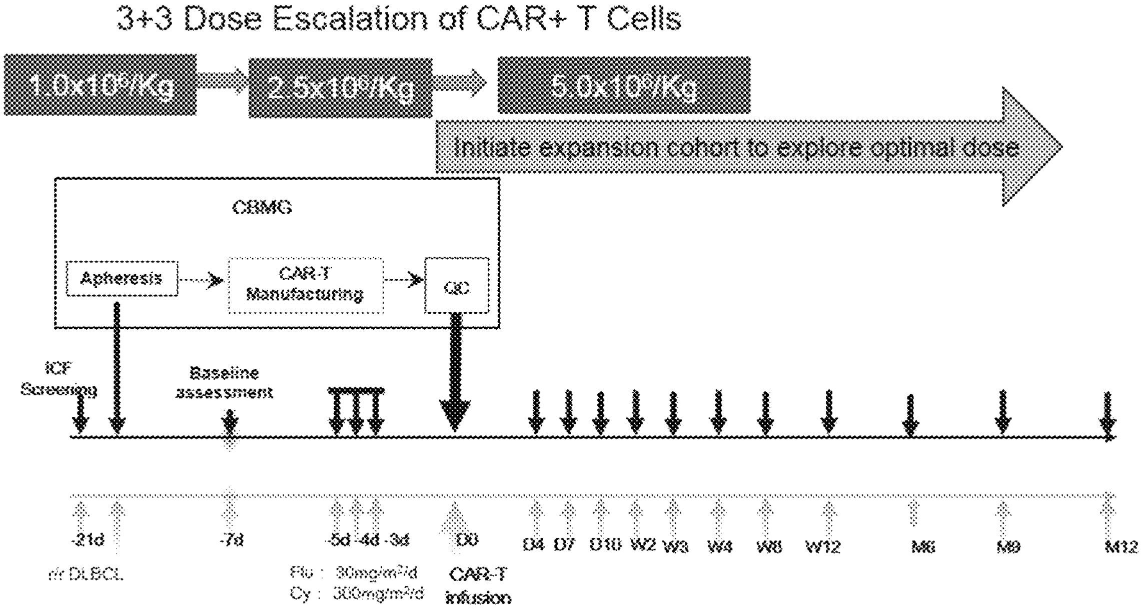
FIG. 12 shows the experimental process of the phase I clinical trial of CART-TN-200F-19.

The experimental process is shown in FIG. 12.

The clinical responses of each subject is shown in Table 3. The results showed that the objective response rate (ORR) was 100%. After 4 weeks of treatment, all three patients achieved partial remission (PR). 1 patient achieved complete remission (CR) at 8w, and 2 patients achieved CR at 3 m, and the clinical response is ongoing.

| Parameter Infusion time | Shanghai Tongji Hospital Patient C001 Nov. 20, 2019 Response | SPD | C003 Dec. 20, 2019 Response | SPD | C004 Dec. 30, 2019 Response | SPD |
|---|---|---|---|---|---|---|
| Baseline | | 2203.12 | | 1751.13 | | 4956.14 |
| 4 w | PR(CT) | 862.86 (60.8%) | PR(CT) | 796.77 (54.5%) | PR(CT) | 1645.45 (66.8%) |
| 8 w | CR(CT) | 211.32 (90.4%) All LDi ≤ 1.5 cm | NE* | | PR(CT) | 1501.39 (69.7%) |
| 12 w | NE* | | CR(PET/CT) | | CR(PET/CT) | |
| 15 w | CR(PET/CT) | | | | | |

*NE because of COVID-19

The adverse events that occurred after treatment are shown in Table 4. The patients generally well tolerated safety profile. One of the three patients had a grade 2 cytokine release syndrome, and two had a grade 1 cytokine release syndrome. There were no death reported, no CRES reported. Cytopenia mostly related to Cy/Flu lymphodepletion.

It needs to be explained that the occurrence of a certain degree of cytokine release syndrome after treatment also shows the effectiveness of CART treatment from the side, and no particularly serious cytokine release syndrome occurred in 3 patients. CART-TN-OF-19 has better security.

TABLE 4

| Adverse reactions of subjects after treatment | | | |
|---|---|---|---|
| Parameter | C001 | C003 | C004 |
| Cytokine release syndrome | Grade 2 | Grade 1 | Grade 1 |
| Neurotoxicity | No | No | No |
| Neutropenia | Grade 4 | Grade 3 | Grade 2 |
| Thrombocytopenia | No | No | No |
| Anemia | Grade 3 | No | No |

Figure 13:
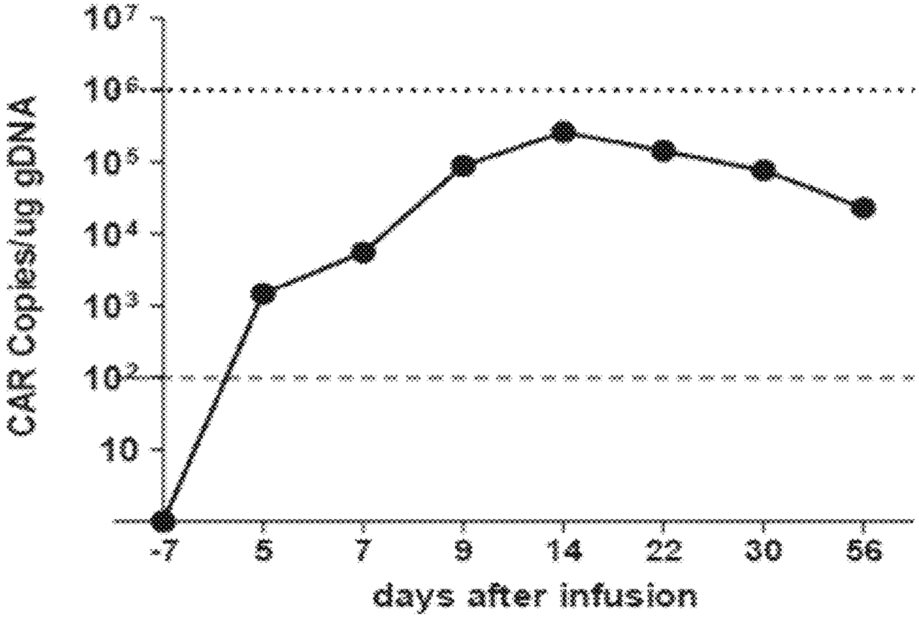
FIG. 13 shows the detection results of the CAR copy number.

The results of the CAR copy number test are shown in FIG. 13, which shows that the CAR copy number reached its peak (higher than $10^5$ copies/microgram gDNA) in 14 days, and there was still a very high copy number after 56 days.

Figure 14:
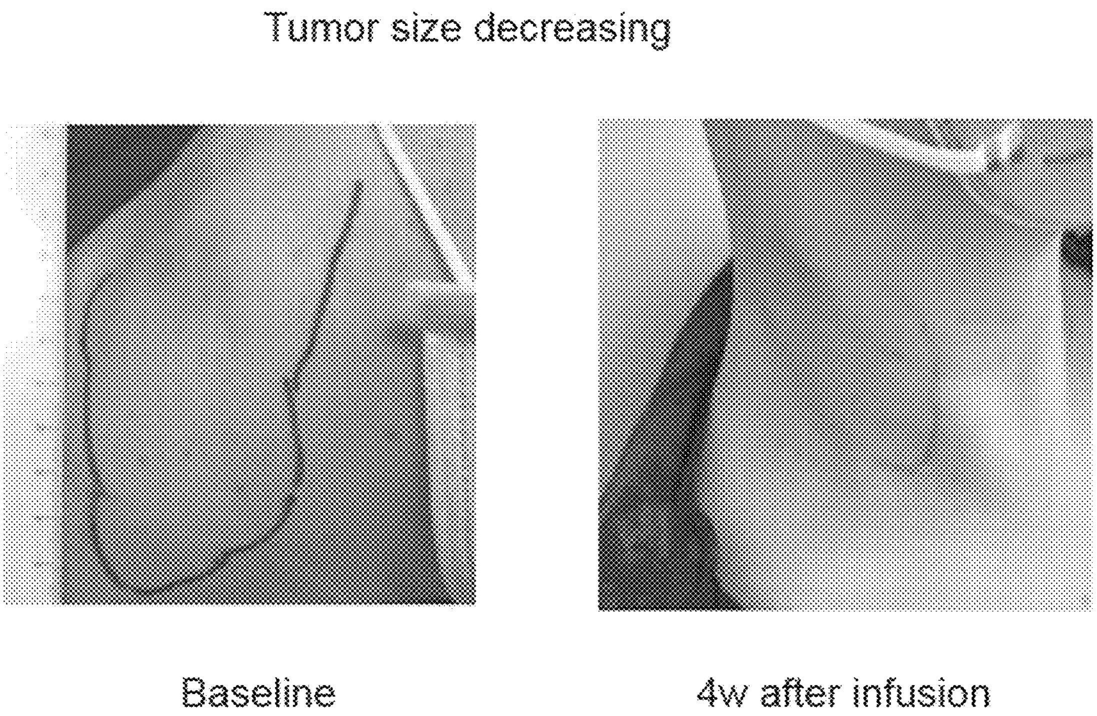
FIG. 14 shows the change in tumor size of a subject.

The change in tumor size of an experimental subject is shown in FIG. 14, which shows that the tumor volume decreased significantly and almost disappeared after 4 weeks of treatment.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A bispecific chimeric antigen receptor (CAR), comprising:

(i) an anti-CD20 antigen-binding region which comprises a light chain variable region ($V_L1$) and a heavy chain variable region ($V_H1$) having amino acid sequences set forth in SEQ ID NO: 4 and SEQ ID NO: 3, respectively; and (ii) an anti-CD19 antigen-binding region which comprises a light chain variable region ($V_L2$) and a heavy chain variable region ($V_H2$) having amino acid sequences set forth in SEQ ID NO: 5 and SEQ ID NO: 6, respectively;

wherein $V_L1$ is located at the N-terminus of $V_H1$, and wherein $V_H2$ is located at the N-terminus of $V_L2$.

2. The bispecific CAR of claim 1, wherein the anti-CD20 antigen-binding region is a single-chain variable fragment (scFv) that specifically binds CD20, and wherein the anti-CD19 antigen-binding region is a scFv that specifically binds CD19.

3. The bispecific CAR of claim 1, further comprising:

(a) a leader sequence, (b) a hinge region, (c) a transmembrane domain, (d) at least one co-stimulatory signaling region, (e) a cytoplasmic signaling domain, or (f) combinations thereof.

4. The bispecific CAR of claim 3, comprising a co-stimulatory signaling region derived from 4-1BB (CD137), CD28, OX40, CD2, CD7, CD27, CD30, CD40, CD70, CD134, PD1, Dap10, CDS, ICAM-1, LFA-1 (CD11a/CD18), ICOS (CD278), NKG2D, GITR, TLR2, or combinations thereof.

5. The bispecific CAR of claim 3, comprising a cytoplasmic signaling domain derived from CD3ζ.

6. The bispecific CAR of claim 3, comprising a hinge region derived from IgG4, CD8, CD28, CD137, or combinations thereof.

7. The bispecific CAR of claim 3, comprising a transmembrane domain derived from CD8, CD28, CD3ε, CD45, CD4, CD5, CD9, CD16, CD22, CD33, CD37, CD64, CD80, CD86, CD134, CD137, CD154, or combinations thereof.

8. The bispecific CAR of claim 1, comprising an amino acid sequence set forth in SEQ ID NO. 16.

9. An immune cell expressing the bispecific CAR of claim 1.

10. The immune cell of claim 9, wherein the immune cell is a T cell or a natural killer (NK) cell.

11. A nucleic acid encoding the bispecific CAR of claim 1.

12. A vector comprising the nucleic acid of claim 11.

13. A method of treating cancer, the method comprising administering the immune cell of claim 11 to a subject in need thereof.

14. The method of claim 13, wherein the cancer is a hematologic cancer.

15. The method of claim 13, wherein the cancer is a B-cell malignancy.

16. The method of claim 13, wherein the cancer is Hodgkin's lymphoma, non-Hodgkin's lymphoma, leukemia, and/or multiple myeloma.

17. The method of claim 13, wherein the cancer is acute myeloid leukemia (AML), multiple myeloma (MM), chronic lymphocytic leukemia (CLL), chronic myelogenous leukemia, acute lymphoblastic leukemia (ALL), diffuse large B cell lymphoma (DLBCL), or combinations thereof.

18. The method of claim 13, wherein the immune cell is allogeneic or autologous.

* * * * *

SEQUENCE LISTING

```
Sequence total quantity: 39
SEQ ID NO: 1            moltype = AA  length = 122
FEATURE                 Location/Qualifiers
REGION                  1..122
                        note = synthesized
REGION                  1..122
                        note = misc_feature - Heavy chain sequence of single-chain
                         variable region (VH) derived from Leu16 antibody
source                  1..122
                        mol_type = protein
                        organism = synthetic construct
SEQUENCE: 1
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARSN YYGSSYWFFD VWGAGTTVTV  120
SS                                                                 122

SEQ ID NO: 2            moltype = AA  length = 106
FEATURE                 Location/Qualifiers
REGION                  1..106
                        note = synthesized
REGION                  1..106
                        note = misc_feature - Light chain sequence of single-chain
                         variable region (VL) derived from Leu16 antibody
source                  1..106
                        mol_type = protein
                        organism = synthetic construct
SEQUENCE: 2
DIVLTQSPAI LSASPGEKVT MTCRASSSVN YMDWYQKKPG SSPKPWIYAT SNLASGVPAR  60
FSGSGSGTSY SLTISRVEAE DAATYYCQQW SFNPPTFGGG TKLEIK                 106

SEQ ID NO: 3            moltype = AA  length = 122
FEATURE                 Location/Qualifiers
REGION                  1..122
                        note = synthesized
REGION                  1..122
                        note = misc_feature - Heavy chain sequence of single-chain
                         variable region (VH) derived from Ofatumumab antibody
source                  1..122
                        mol_type = protein
                        organism = synthetic construct
SEQUENCE: 3
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                                 122

SEQ ID NO: 4            moltype = AA  length = 107
FEATURE                 Location/Qualifiers
REGION                  1..107
                        note = synthesized
REGION                  1..107
                        note = misc_feature - Light chain sequence of single-chain
                         variable region (VL) derived from Ofatumumab antibody
source                  1..107
                        mol_type = protein
                        organism = synthetic construct
SEQUENCE: 4
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK                107

SEQ ID NO: 5            moltype = AA  length = 107
FEATURE                 Location/Qualifiers
REGION                  1..107
                        note = synthesized
REGION                  1..107
                        note = misc_feature - Amino acid sequence of the light
                         chain of single-chain variable region (VL) derived from
                         FMC63 antibody
source                  1..107
                        mol_type = protein
                        organism = synthetic construct
SEQUENCE: 5
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT                107

SEQ ID NO: 6            moltype = AA  length = 120
FEATURE                 Location/Qualifiers
REGION                  1..120
                        note = synthesized
```

```
REGION                  1..120
                        note = misc_feature - Amino acid sequence of the heavy
                         chain of single-chain variable region (VH) derived from
                         FMC63 antibody
source                  1..120
                        mol_type = protein
                        organism = synthetic construct
SEQUENCE: 6
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 7            moltype = AA  length = 5
FEATURE                 Location/Qualifiers
REGION                  1..5
                        note = synthesized
REGION                  1..5
                        note = misc_feature - Linker sequences
source                  1..5
                        mol_type = protein
                        organism = synthetic construct
SEQUENCE: 7
GGGGS                                                              5

SEQ ID NO: 8            moltype = AA  length = 21
FEATURE                 Location/Qualifiers
REGION                  1..21
                        note = synthesized
REGION                  1..21
                        note = misc_feature - Leader sequence of CD8 antigen
source                  1..21
                        mol_type = protein
                        organism = synthetic construct
SEQUENCE: 8
MALPVTALLL PLALLLHAAR P                                            21

SEQ ID NO: 9            moltype = AA  length = 229
FEATURE                 Location/Qualifiers
REGION                  1..229
                        note = synthesized
REGION                  1..229
                        note = misc_feature - IgG4 Hinge-CH2-CH3
source                  1..229
                        mol_type = protein
                        organism = synthetic construct
SEQUENCE: 9
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 10           moltype = AA  length = 24
FEATURE                 Location/Qualifiers
REGION                  1..24
                        note = synthesized
REGION                  1..24
                        note = misc_feature - CD8 transmembrane region
source                  1..24
                        mol_type = protein
                        organism = synthetic construct
SEQUENCE: 10
IYIWAPLAGT CGVLLLSLVI TLYC                                         24

SEQ ID NO: 11           moltype = AA  length = 27
FEATURE                 Location/Qualifiers
REGION                  1..27
                        note = synthesized
REGION                  1..27
                        note = misc_feature - CD28 transmembrane region
source                  1..27
                        mol_type = protein
                        organism = synthetic construct
SEQUENCE: 11
FWVLVVVGGV LACYSLLVTV AFIIFWV                                      27

SEQ ID NO: 12           moltype = AA  length = 42
FEATURE                 Location/Qualifiers
REGION                  1..42
                        note = synthesized
REGION                  1..42
```

```
                      note = misc_feature - Co-stimulatory factor signal region
                       derived from 4-1BB
source                1..42
                      mol_type = protein
                      organism = synthetic construct
SEQUENCE: 12
KRGRKKLLYI FKQPFMRPVQ TTQEEDGCSC RFPEEEEGGC EL                    42

SEQ ID NO: 13         moltype = AA  length = 41
FEATURE               Location/Qualifiers
REGION                1..41
                      note = synthesized
REGION                1..41
                      note = misc_feature - Co-stimulatory factor signal region
                       derived from CD28
source                1..41
                      mol_type = protein
                      organism = synthetic construct
SEQUENCE: 13
RSKRSRLLHS DYMNMTPRRP GPTRKHYQPY APPRDFAAYR S                     41

SEQ ID NO: 14         moltype = AA  length = 113
FEATURE               Location/Qualifiers
REGION                1..113
                      note = synthesized
REGION                1..113
                      note = misc_feature - Signaling region of CD3
source                1..113
                      mol_type = protein
                      organism = synthetic construct
SEQUENCE: 14
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR         113

SEQ ID NO: 15         moltype = AA  length = 710
FEATURE               Location/Qualifiers
REGION                1..710
                      note = synthesized
REGION                1..710
                      note = misc_feature - Amino acid sequence of TN-LEU-19
source                1..710
                      mol_type = protein
                      organism = synthetic construct
SEQUENCE: 15
METDTLLLWV LLLWVPGSTG DIVLTQSPAI LSASPGEKVT MTCRASSSVN YMDWYQKKPG  60
SSPKPWIYAT SNLASGVPAR FSGSGSGTSY SLTISRVEAE DAATYYCQQW SFNPPTFGGG  120
TKLEIKGSTS GGGSGGGSGG GGSSEVQLQQ SGAELVKPGA SVKMSCKASG YTFTSYNMHW  180
VKQTPGQGLE WIGAIYPGNG DTSYNQKFKG KATLTADKSS STAYMQLSSL TSEDSADYYC  240
ARSNYYGSSY WFFDVWGAGT TVTVSSGGGG SEVKLQESGP GLVAPSQSLS VTCTVSGVSL  300
PDYGVSWIRQ PPRKGLEWLG VIWGSETTYY NSALKSRLTI IKDNSKSQVF LKMNSLQTDD  360
TAIYYCAKHY YYGGSYAMDY WGQGTSVTVS SGSTSGSGKP GSGEGSTKGD IQMTQTTSSL  420
SASLGDRVTI SCRASQDISK YLNWYQQKPD GTVKLLIYHT SRLHSGVPSR FSGSGSGTDY  480
SLTISNLEQE DIATYFCQQG NTLPYTFGGG TKLEITESKY GPPCPPCPMF WVLVVVGGVL  540
ACYSLLVTVA FIIFWVKRGR KKLLYIFKQP FMRPVQTTQE EDGCSCRFPE EEEGGCELRV  600
KFSRSADAPA YQQGQNQLYN ELNLGRREEY DVLDKRRGRD PEMGGKPRRK NPQEGLYNEL  660
QKDKMAEAYS EIGMKGERRR GKGHDGLYQG LSTATKDTYD ALHMQALPPR            710

SEQ ID NO: 16         moltype = AA  length = 712
FEATURE               Location/Qualifiers
REGION                1..712
                      note = synthesized
REGION                1..712
                      note = misc_feature - Amino acid sequence of TN-OF-19
source                1..712
                      mol_type = protein
                      organism = synthetic construct
SEQUENCE: 16
MALPVTALLL PLALLLHAAR PEIVLTQSPA TLSLSPGERA TLSCRASQSV SSYLAWYQQK  60
PGQAPRLLIY DASNRATGIP ARFSGSGSGT DFTLTISSLE PEDFAVYYCQ QRSNWPITFG  120
QGTRLEIKGS TSGGGSGGGS GGGGSSEVQL VESGGGLVQP GRSLRLSCAA SGFTFNDYAM  180
HWVRQAPGKG LEWVSTISWN SGSIGYADSV KGRFTISRDN AKKSLYLQMN SLRAEDTALY  240
YCAKDIQYGN YYYGMDVWGQ GTTVTVSSGG GGSEVKLQES GPGLVAPSQS LSVTCTVSGV  300
SLPDYGVSWI RQPPRKGLEW LGVIWGSETT YYNSALKSRL TIIKDNSKSQ VFLKMNSLQT  360
DDTAIYYCAK HYYYGGSYAM DYWGQGTSVT VSSGSTSGSG KPGSGEGSTK GDIQMTQTTS  420
SLSASLGDRV TISCRASQDI SKYLNWYQQK PDGTVKLLIY HTSRLHSGVP SRFSGSGSGT  480
DYSLTISNLE QEDIATYFCQ QGNTLPYTFG GGTKLEITES KYGPPCPPCP MFWVLVVVGG  540
VLACYSLLVT VAFIIFWVKR GRKKLLYIFK QPFMRPVQTT QEEDGCSCRF PEEEEGGCEL  600
RVKFSRSADA PAYQQGQNQL YNELNLGRRE EYDVLDKRRG RDPEMGGKPR RKNPQEGLYN  660
ELQKDKMAEA YSEIGMKGER RRGKGHDGLY QGLSTATKDT YDALHMQALP PR          712
```

```
SEQ ID NO: 17          moltype = DNA  length = 2130
FEATURE                Location/Qualifiers
misc_feature           1..2130
                       note = synthesized
misc_feature           1..2130
                       note = Nucleic acid sequence of TN-LEU-19
source                 1..2130
                       mol_type = other DNA
                       organism = synthetic construct
SEQUENCE: 17
atggagacag acacactcct gctatgggtg ctgctgctct gggttccagg ttccacaggt  60
gacattgtgc tgacccaatc tccagctatc ctgtctgcat ctccagggga gaaggtcaca  120
atgacttgca gggccagctc aagtgtaaat tacatggact ggtaccagaa gaagccagga  180
tcctccccca aaccctggat ttatgccaca tccaacctgg cttctggagt ccctgctcgc  240
ttcagtggca gtgggtctgg gacctcttac tctctcacaa tcagcagagt ggaggctgaa  300
gatgctgcca cttattactg ccagcagtgg agttttaatc cacccacgtt cggagggggg  360
accaagctgg aaataaaagg cagtactagc ggtggtggct ccgggggcgg ttccggtggg  420
ggcggcagca gcgaggtgca gctgcagcag tctggggctg agctggtgaa gcctggggcc  480
tcagtgaaga tgtcctgcaa ggcttctggc tacacattta ccagttacaa tatgcactgg  540
gtaaagcaga cacctggaca gggcctggaa tggattggag ctatttatcc aggaaatggt  600
gatacttcct acaatcagaa gttcaaaggc aaggccacat tgactgcaga caaatcctcc  660
agcacagcct acatgcagct cagcagcctg acatctgagg actctgcgga ctattactgt  720
gcaagatcta attattacgg tagtagctac tggttcttcg atgtctgggg cgcagggacc  780
acggtcaccg tctcctcagg aggtggtgga tccgaggtga agctgcagga aagcggccct  840
ggcctggtgg cccccagcca gagcctgagc gtgacctgca ccgtgagcgg cgtgagcctg  900
cccgactacg gcgtgagctg gatccggcag ccccccagga agggcctgga atggctgggc  960
gtgatctggg gcagcgagac cacctactac aacagcgccc tgaagagccg gctgaccatc  1020
atcaaggaca acagcaagag ccaggtgttc ctgaagatga acagcctgca gaccgacgac  1080
accgccatct actactgcgc caagcactac tactacggcg gcagctacgc catggactac  1140
tggggccagg gcaccagcgt gaccgtgagc agcggcagca cctccggcag cggcaagcct  1200
ggcagcggcg agggcagcac caagggcgac atccagatga cccagaccac ctccagcctg  1260
agcgccagcc tgggcgaccg ggtgaccatc agctgccggg ccagccagga catcagcaag  1320
tacctgaact ggtatcagca gaagcccgac ggcaccgtca agctgctgat ctaccacacc  1380
agccggctgc acagcggcgt gcccagccgg tttagcggca gcggctccgg caccgactac  1440
agcctgacca tctccaacct ggaacaggaa gatatcgcca cctacttttg ccagcagggc  1500
aacacactgc cctacacctt tggcggcgga acaaagctgg aaatcaccga gagcaagtac  1560
ggaccgccct gccccccttg ccctatgttc tgggtgctgg tggtggtcgg aggcgtgctg  1620
gcctgctaca gcctgctggt caccgtggcc ttcatcatct tttgggtgaa acggggcaga  1680
aagaaactcc tgtatatatt caaacaacca tttatgagac cagtacaaac tactcaagag  1740
gaagatggct gtagctgccg atttccagaa gaagaagaag gaggatgtga actgcgggtg  1800
aagttcagca gaagcgccga cgcccctgcc taccagcagg gccagaatca gctgtacaac  1860
gagctgaacc tgggcagaag ggaagagtac gacgtcctgg ataagcggag aggccgggac  1920
cctgagatgg gcggcaagcc tcggcggaag aacccccagg aaggcctgta taacgaactg  1980
cagaaagaca agatggccga ggcctacagc gagatcggca tgaagggcga gcggaggcgg  2040
ggcaagggcc acgacggcct gtatcagggc ctgtccaccg ccaccaagga tacctacgac  2100
gccctgcaca tgcaggccct gcccccaagg                                  2130

SEQ ID NO: 18          moltype = DNA  length = 2136
FEATURE                Location/Qualifiers
misc_feature           1..2136
                       note = synthesized
misc_feature           1..2136
                       note = Nucleic acid sequence of TN-OF-19
source                 1..2136
                       mol_type = other DNA
                       organism = synthetic construct
SEQUENCE: 18
atggccttac cagtgaccgc cttgctcctg ccgctggcct tgctgctcca cgccgccagg  60
ccggaaattg tgttgacaca gtctccagcc accctgtctt tgtctccagg ggaaagagcc  120
accctctcct gcagggccag tcagagtgtt agcagctact tagcctggta ccaacagaaa  180
cctggccagg ctcccaggct cctcatctat gatgcatcca acagggccac tggcatccca  240
gccaggttca gtggcagtgg gtctgggaca gacttcactc tcaccatcag cagcctagag  300
cctgaagatt ttgcagttta ttactgtcag cagcgtagca actggccgat caccttcggc  360
caagggacac gactggagat taaaggcagt actagcggtg gtggctccgg gggcggttcc  420
ggtgggggcg gcagcagcga agtgcagctg gtggagtctg ggggaggctt ggtacagcct  480
ggcaggtccc tgagactctc ctgtgcagcc tctggattca cctttaatga ttatgccatg  540
cactgggtcc ggcaagctcc agggaagggc ctggagtggg tctcaactat tagttggaat  600
agtggttcca taggctatgc ggactctgtg aagggccgat tcaccatctc cagagacaac  660
gccaagaagt ccctgtatct gcaaatgaac agtctgagag ctgaggacac ggccttgtat  720
tactgtgcaa aagatataca gtacggcaac tactactacg gtatggacgt ctggggccaa  780
gggaccacgg tcaccgtctc ctcaggaggt ggtggatccg aggtgaagct gcaggaaagc  840
ggccctggcc tggtggcccc cagccagagc ctgagcgtga cctgcaccgt gagcggcgtg  900
agcctgcccg actacggcgt gagctggatc cggcagcccc ccaggaaggg cctggaatgg  960
ctgggcgtga tctggggcag cgagaccacc tactacaaca gcgccctgaa gagccggctg  1020
accatcatca aggacaacag caagagccag gtgttcctga agatgaacag cctgcagacc  1080
gacgacaccg ccatctacta ctgcgccaag cactactact acggcggcag ctacgccatg  1140
gactactggg gccagggcac cagcgtgacc gtgagcagcg gcagcacctc cggcagcggc  1200
aagcctggca gcggcgaggg cagcaccaag ggcgacatcc agatgaccca gaccacctcc  1260
```

```
agcctgagcg ccagcctggg cgaccgggtg accatcagct gccgggccag ccaggacatc  1320
agcaagtacc tgaactggta tcagcagaag cccgacggca ccgtcaagct gctgatctac  1380
cacaccagcc ggctgcacag cggcgtgccc agccggttta gcggcagcgg ctccggcacc  1440
gactacagcc tgaccatctc caacctggaa caggaagata tcgccaccta cttttgccag  1500
cagggcaaca cactgcccta caccttttggc ggcggaacaa agctggaaat caccgagagc  1560
aagtacggac cgccctgccc cccttgccct atgttctggg tgctggtggt ggtcggaggc  1620
gtgctggcct gctacagcct gctggtcacc gtggccttca tcatcttttg ggtgaaacgg  1680
ggcagaaaga aactcctgta tatattcaaa caaccattta tgagaccagt acaaactact  1740
caagaggaag atggctgtag ctgccgattt ccagaagaag aagaaggagg atgtgaactg  1800
cgggtgaagt tcagcagaag cgccgacgcc cctgcctacc agcagggcca gaatcagctg  1860
tacaacgagc tgaacctggg cagaagggaa gagtacgacg tcctggataa gcggagaggc  1920
cgggaccctg agatgggcgg caagcctcgg cggaagaacc cccaggaagg cctgtataac  1980
gaactgcaga aagacaagat ggccgaggcc tacagcgaga tcggcatgaa gggcgagcgg  2040
aggcggggca agggccacga cggcctgtat cagggcctgt ccaccgccac caaggatacc  2100
tacgacgccc tgcacatgca ggccctgccc ccaagg                           2136

SEQ ID NO: 19          moltype = AA  length = 15
FEATURE                Location/Qualifiers
REGION                 1..15
                       note = synthesized
REGION                 1..15
                       note = misc_feature - Amino acid sequence of flexible
                        linker I
source                 1..15
                       mol_type = protein
                       organism = synthetic construct
SEQUENCE: 19
GGGGSGGGGS GGGGS                                                  15

SEQ ID NO: 20          moltype = DNA  length = 45
FEATURE                Location/Qualifiers
misc_feature           1..45
                       note = synthesized
misc_feature           1..45
                       note = Nucleic acid sequence of flexible linker I
source                 1..45
                       mol_type = other DNA
                       organism = synthetic construct
SEQUENCE: 20
ggtggcggtg gctcgggcgg tggtgggtcg ggtggcggcg gatct                 45

SEQ ID NO: 21          moltype = DNA  length = 321
FEATURE                Location/Qualifiers
misc_feature           1..321
                       note = synthesized
misc_feature           1..321
                       note = Nucleotide sequence of the light chain of
                        single-chain variable region (VL) derived from FMC63
                        antibody
source                 1..321
                       mol_type = other DNA
                       organism = synthetic construct
SEQUENCE: 21
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggaccaagc tggagatcac a                                           321

SEQ ID NO: 22          moltype = DNA  length = 360
FEATURE                Location/Qualifiers
misc_feature           1..360
                       note = synthesized
misc_feature           1..360
                       note = Nucleotide sequence of the heavy chain of
                        single-chain variable region (VH) derived from FMC63
                        antibody
source                 1..360
                       mol_type = other DNA
                       organism = synthetic construct
SEQUENCE: 22
gaggtgaaac tgcaggagtc aggacctggc ctggtggcgc cctcacagag cctgtccgtc  60
acatgcactg tctcaggggt ctcattaccc gactatggtg taagctggat tcgccagcct  120
ccacgaaagg gtctggagtg gctgggagta atatggggta gtgaaaccac atactataat  180
tcagctctca aatccagact gaccatcatc aaggacaact ccaagagcca agttttctta  240
aaaatgaaca gtctgcaaac tgatgacaca gccatttact actgtgccaa acattattac  300
tacggtggta gctatgctat ggactactgg ggccaaggaa cctcagtcac cgtctcctca  360
```

```
SEQ ID NO: 23          moltype = AA  length = 472
FEATURE                Location/Qualifiers
REGION                 1..472
                       note = synthesized
REGION                 1..472
                       note = misc_feature - Chimeric antigen receptor
source                 1..472
                       mol_type = protein
                       organism = synthetic construct
SEQUENCE: 23
MDIQLTQSPA ILSASPGEKV TMTCRASSSL SFMHWYQQKP GSSPKPWIYA TSNLASGVPA  60
RFSGSGSGTS YSLTISTVEA EDAASYFCHQ WSSNPLTFGA GTKLEISSGG GGSGGGGSGD  120
VMGVDSGGGL VQPGGSRKLS CAAPGFTFSS FGMHWVRQAP EKGLEWVAYI SSPSSTLHYA  180
DRVKGRFTIS RDNPKNTLFL QMKLPSLCYG LLGPRDHVHR LLKTRLSNSI MYFSHFVPVF  240
LPAKPTTTPA PRPPTPAPTI ASQPLSLRPE ACRPAAGGAV HTRGLDFACD IYIWAPLAGT  300
CGVLLLSLVI TLYCRSKRGR KKLLYIFKQP FMRPVQTTQE EDGCSCRFPE EEEGGCELEF  360
RVKFSRSADA PAYQQGQNQL YNELNLGRRE EYDVLDKRRG RDPEMGGKPR RKNPQEGLYN  420
ELQKDKMAEA YSEIGMKGER RRGKGHDGLY QGLSTATKDT YDALHMQALP PR          472

SEQ ID NO: 24          moltype = AA  length = 492
FEATURE                Location/Qualifiers
REGION                 1..492
                       note = synthesized
REGION                 1..492
                       note = misc_feature - Chimeric antigen receptor
source                 1..492
                       mol_type = protein
                       organism = synthetic construct
SEQUENCE: 24
MALPVTALLL PLALLLHAAR PDIQLTQSPA ILSASPGEKV TMTCRASSSL SFMHWYQQKP  60
GSSPKPWIYA TSNLASGVPA RFSGSGSGTS YSLTISTVEA EDAASYFCHQ WSSNPLTFGA  120
GTKLEISSGG GGSGGGGSGD VMGVDSGGGL VQPGGSRKLS CAAPGFTFSS FGMHWVRQAP  180
EKGLEWVAYI SSPSSTLHYA DRVKGRFTIS RDNPKNTLFL QMKLPSLCYG LLGPRDHVHR  240
LLKTRLSNSI MYFSHFVPVF LPAKPTTTPA PRPPTPAPTI ASQPLSLRPE ACRPAAGGAV  300
HTRGLDFACD IYIWAPLAGT CGVLLLSLVI TLYCRSKRGR KKLLYIFKQP FMRPVQTTQE  360
EDGCSCRFPE EEEGGCELEF RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                      492

SEQ ID NO: 25          moltype = AA  length = 377
FEATURE                Location/Qualifiers
REGION                 1..377
                       note = synthesized
REGION                 1..377
                       note = misc_feature - Chimeric antigen receptor
source                 1..377
                       mol_type = protein
                       organism = synthetic construct
SEQUENCE: 25
MALPVTALLL PLALLLHAAR PDIQLTQSPA ILSASPGEKV TMTCRASSSL SFMHWYQQKP  60
GSSPKPWIYA TSNLASGVPA RFSGSGSGTS YSLTISTVEA EDAASYFCHQ WSSNPLTFGA  120
GTKLEIGGGG SGGGGSGGGG SDVMGVDSGG GLVQPGGSRK LSCAAPGFTF SSFGMHWVRQ  180
APEKGLEWVA YISSPSSTLH YADRVKGRFT ISRDNPKNTL FLQMKLPSLC YGLLGPRDHV  240
HRLLTRTTTP APRPPTPAPT IASQPLSLRP EACRPAAGGA VHTRGLDFAC DIYIWAPLAG  300
TCGVLLLSLV ITLYCRSKRG RKKLLYIFKQ PFMRPVQTTQ EEDGCSCRFP EEEEGGCELE  360
FELGTFKTND LQGSCRS                                                 377

SEQ ID NO: 26          moltype = AA  length = 377
FEATURE                Location/Qualifiers
REGION                 1..377
                       note = synthesized
REGION                 1..377
                       note = misc_feature - Chimeric antigen receptor
source                 1..377
                       mol_type = protein
                       organism = synthetic construct
SEQUENCE: 26
MALPVTALLL PLALLLHAAR PDVMGVDSGG GLVQPGGSRK LSCAAPGFTF SSFGMHWVRQ  60
APEKGLEWVA YISSPSSTLH YADRVKGRFT ISRDNPKNTL FLQMKLPSLC YGLLGPRDHV  120
HRLLGGGGSG GGGSGGGGSD IQLTQSPAIL SASPGEKVTM TCRASSSLSF MHWYQQKPGS  180
SPKPWIYATS NLASGVPARF SGSGSGTSYS LTISTVEAED AASYFCHQWS SNPLTFGAGT  240
KLEITRTTTP APRPPTPAPT IASQPLSLRP EACRPAAGGA VHTRGLDFAC DIYIWAPLAG  300
TCGVLLLSLV ITLYCRSKRG RKKLLYIFKQ PFMRPVQTTQ EEDGCSCRFP EEEEGGCELE  360
FELGTFKTND LQGSCRS                                                 377

SEQ ID NO: 27          moltype = AA  length = 396
FEATURE                Location/Qualifiers
REGION                 1..396
                       note = synthesized
```

```
REGION                  1..396
                        note = misc_feature - Chimeric antigen receptor
source                  1..396
                        mol_type = protein
                        organism = synthetic construct
SEQUENCE: 27
MALPVTALLL PLALLLHAAR PQIVLSQSPA ILSASPGEKV TMTCRASSSV SYIHWFQQKP  60
GSSPKPWIYA TSNLASGVPV RFSGSGSGTS YSLTISRVEA EDAATYYCQQ WTSNPPTFGG  120
GTKLEIKGGG GSGGGGSGGG GSQVQLQQPG AELVKPGASV KMSCKASGYT FTSYNMHWVK  180
QTPGRGLEWI GAIYPGNGDT SYNQKFKGKA TLTADKSSST AYMQLSSLTS EDSAVYYCAR  240
STYYGGDWYF NVWGAGTTVT VSATRTTTPA PRPPTPAPTI ASQPLSLRPE ACRPAAGGAV  300
HTRGLDFACD IYIWAPLAGT CGVLLLSLVI TLYCRSKRGR KKLLYIFKQP FMRPVQTTQE  360
EDGCSCRFPE EEEGGCELEF ELGTFKTNDL QGSCRS                           396

SEQ ID NO: 28           moltype = AA  length = 396
FEATURE                 Location/Qualifiers
REGION                  1..396
                        note = synthesized
REGION                  1..396
                        note = misc_feature - Chimeric antigen receptor
source                  1..396
                        mol_type = protein
                        organism = synthetic construct
SEQUENCE: 28
MALPVTALLL PLALLLHAAR PQVQLQQPGA ELVKPGASVK MSCKASGYTF TSYNMHWVKQ  60
TPGRGLEWIG AIYPGNGDTS YNQKFKGKAT LTADKSSSTA YMQLSSLTSE DSAVYYCARS  120
TYYGGDWYFN VWGAGTTVTV SAGGGGSGGG GSGGGGSQIV LSQSPAILSA SPGEKVTMTC  180
RASSSVSYIH WFQQKPGSSP KPWIYATSNL ASGVPVRFSG SGSGTSYSLT ISRVEAEDAA  240
TYYCQQWTSN PPTFGGGTKL EIKTRTTTPA PRPPTPAPTI ASQPLSLRPE ACRPAAGGAV  300
HTRGLDFACD IYIWAPLAGT CGVLLLSLVI TLYCRSKRGR KKLLYIFKQP FMRPVQTTQE  360
EDGCSCRFPE EEEGGCELEF ELGTFKTNDL QGSCRS                           396

SEQ ID NO: 29           moltype = AA  length = 715
FEATURE                 Location/Qualifiers
REGION                  1..715
                        note = synthesized
REGION                  1..715
                        note = misc_feature - Chimeric antigen receptor
source                  1..715
                        mol_type = protein
                        organism = synthetic construct
SEQUENCE: 29
MALPVTALLL PLALLLHAAR PEVQLQQSGA ELVKPGASVK MSCKASGYTF TSYNMHWVKQ  60
TPGQGLEWIG AIYPGNGDTS YNQKFKGKAT LTADKSSSTA YMQLSSLTSE DSADYYCARS  120
NYYGSSYWFF DVWGAGTTVT VSSGGGGSGG GGSGGGGSDI VLTQSPAILS ASPGEKVTMT  180
CRASSSVNYM DWYQKKPGSS PKPWIYATSN LASGVPARFS GSGSGTSYSL TISRVEAEDA  240
ATYYCQQWSF NPPTFGGGTK LEIKESKYGP PCPPCPAPEF LGGPSVFLFP PKPKDTLMIS  300
RTPEVTCVVV DVSQEDPEVQ FNWYVDGVEV HNAKTKPREE QFNSTYRVVS VLTVLHQDWL  360
NGKEYKCKVS NKGLPSSIEK TISKAKGQPR EPQVYTLPPS QEEMTKNQVS LTCLVKGFYP  420
SDIAVEWESN GQPENNYKTT PPVLDSDGSF FLYSRLTVDK SRWQEGNVFS CSVMHEALHN  480
HYTQKSLSLS LGKFWVLVVV GGVLACYSLL VTVAFIIFWV RSKRSRLLHS DYMNMTPRRP  540
GPTRKHYQPY APPRDFAAYR SKRGRKKLLY IFKQPFMRPV QTTQEEDGCS CRFPEEEEGG  600
CELRVKFSRS ADAPAYKQGQ NQLYNELNLG RREEYDVLDK RRGRDPEMGG KPRRKNPQEG  660
LYNELQKDKM AEAYSEIGMK GERRRGKGHD GLYQGLSTAT KDTYDALHMQ ALPPR       715

SEQ ID NO: 30           moltype = AA  length = 715
FEATURE                 Location/Qualifiers
REGION                  1..715
                        note = synthesized
REGION                  1..715
                        note = misc_feature - Chimeric antigen receptor
source                  1..715
                        mol_type = protein
                        organism = synthetic construct
SEQUENCE: 30
MALPVTALLL PLALLLHAAR PEVQLQQSGA ELVKPGASVK MSCKASGYTF TSYNMHWVKQ  60
TPGQGLEWIG AIYPGNGDTS YNQKFKGKAT LTADKSSSTA YMQLSSLTSE DSADYYCARS  120
NYYGSSYWFF DVWGAGTTVT VSSGGGGSGG GGSGGGGSDI VLTQSPAILS ASPGEKVTMT  180
CRASSSVNYM DWYQKKPGSS PKPWIYATSN LASGVPARFS GSGSGTSYSL TISRVEAEDA  240
ATYYCQQWSF NPPTFGGGTK LEIKESKYGP PCPPCPAPEF LGGPSVFLFP PKPKDTLMIS  300
RTPEVTCVVV DVSQEDPEVQ FNWYVDGVEV HNAKTKPREE QFNSTYRVVS VLTVLHQDWL  360
NGKEYKCKVS NKGLPSSIEK TISKAKGQPR EPQVYTLPPS QEEMTKNQVS LTCLVKGFYP  420
SDIAVEWESN GQPENNYKTT PPVLDSDGSF FLYSRLTVDK SRWQEGNVFS CSVMHEALHN  480
HYTQKSLSLS LGKFWVLVVV GGVLACYSLL VTVAFIIFWV RSKRSRLLHS DYMNMTPRRP  540
GPTRKHYQPY APPRDFAAYR SKRGRKKLLY IFKQPFMRPV QTTQEEDGCS CRFPEEEEGG  600
CELRVKFSRS ADAPAYKQGQ NQLYNELNLG RREEYDVLDK RRGRDPEMGG KPRRKNPQEG  660
LYNELQKDKM AEAYSEIGMK GERRRGKGHD GLYQGLSTAT KDTYDALHMQ ALPPR       715

SEQ ID NO: 31           moltype = AA  length = 671
```

```
FEATURE               Location/Qualifiers
REGION                1..671
                      note = synthesized
REGION                1..671
                      note = misc_feature - Chimeric antigen receptor
source                1..671
                      mol_type = protein
                      organism = synthetic construct
SEQUENCE: 31
MALPVTALLL PLALLLHAAR PDIVLTQSPA ILSASPGEKV TMTCRASSSV NYMDWYQKKP  60
GSSPKPWIYA TSNLASGVPA RFSGSGSGTS YSLTISRVEA EDAATYYCQQ WSFNPPTFGG  120
GTKLEIKGGG GSGGGGSGGG GSEVQLQQSG AELVKPGASV KMSCKASGYT FTSYNMHWVK  180
QTPGQGLEWI GAIYPGNGDT SYNQKFKGKA TLTADKSSST AYMQLSSLTS EDSADYYCAR  240
SNYYGSSYWF FDVWGAGTTV TVSSESKYGP PCPPCPAPEF LGGPSVFLFP PKPKDTLMIS  300
RTPEVTCVVV DVSQEDPEVQ FNWYVDGVEV HNAKTKPREE QFNSTYRVVS VLTVLHQDWL  360
NGKEYKCKVS NKGLPSSIEK TISKAKGQPR EPQVYTLPPS QEEMTKNQVS LTCLVKGFYP  420
SDIAVEWESN GQPENNYKTT PPVLDSDGSF FLYSRLTVDK SRWQEGNVFS CSVMHEALHN  480
HYTQKSLSLS LGKIYIWAPL AGTCGVLLLS LVITLYCKRG RKKLLYIFKQ PFMRPVQTTQ  540
EEDGCSCRFP EEEEGGCELR VKFSRSADAP AYKQGQNQLY NELNLGRREE YDVLDKRRGR  600
DPEMGGKPRR KNPQEGLYNE LQKDKMAEAY SEIGMKGERR RGKGHDGLYQ GLSTATKDTY  660
DALHMQALPP R                                                      671

SEQ ID NO: 32         moltype = AA  length = 671
FEATURE               Location/Qualifiers
REGION                1..671
                      note = synthesized
REGION                1..671
                      note = misc_feature - Chimeric antigen receptor
source                1..671
                      mol_type = protein
                      organism = synthetic construct
SEQUENCE: 32
MALPVTALLL PLALLLHAAR PEVQLQQSGA ELVKPGASVK MSCKASGYTF TSYNMHWVKQ  60
TPGQGLEWIG AIYPGNGDTS YNQKFKGKAT LTADKSSSTA YMQLSSLTSE DSADYYCARS  120
NYYGSSYWFF DVWGAGTTVT VSSGGGGSGG GGSGGGGSDI VLTQSPAILS ASPGEKVTMT  180
CRASSSVNYM DWYQKKPGSS PKPWIYATSN LASGVPARFS GSGSGTSYSL TISRVEAEDA  240
ATYYCQQWSF NPPTFGGGTK LEIKESKYGP PCPPCPAPEF LGGPSVFLFP PKPKDTLMIS  300
RTPEVTCVVV DVSQEDPEVQ FNWYVDGVEV HNAKTKPREE QFNSTYRVVS VLTVLHQDWL  360
NGKEYKCKVS NKGLPSSIEK TISKAKGQPR EPQVYTLPPS QEEMTKNQVS LTCLVKGFYP  420
SDIAVEWESN GQPENNYKTT PPVLDSDGSF FLYSRLTVDK SRWQEGNVFS CSVMHEALHN  480
HYTQKSLSLS LGKIYIWAPL AGTCGVLLLS LVITLYCKRG RKKLLYIFKQ PFMRPVQTTQ  540
EEDGCSCRFP EEEEGGCELR VKFSRSADAP AYKQGQNQLY NELNLGRREE YDVLDKRRGR  600
DPEMGGKPRR KNPQEGLYNE LQKDKMAEAY SEIGMKGERR RGKGHDGLYQ GLSTATKDTY  660
DALHMQALPP R                                                      671

SEQ ID NO: 33         moltype = AA  length = 677
FEATURE               Location/Qualifiers
REGION                1..677
                      note = synthesized
REGION                1..677
                      note = misc_feature - Chimeric antigen receptor
source                1..677
                      mol_type = protein
                      organism = synthetic construct
SEQUENCE: 33
MALPVTALLL PLALLLHAAR PQVQLVQSGA EVKKPGSSVK VSCKASGYAF SYSWINWVRQ  60
APGQGLEWMG RIFPGDGDTD YNGKFKGRVT ITADKSTSTA YMELSSLRSE DTAVYYCARN  120
VFDGYWLVYW GQGTLVTVSS GGGGSGGGGS GGGGSDIVMT QTPLSLPVTP GEPASISCRS  180
SKSLLHSNGI TYLYWYLQKP GQSPQLLIYQ MSNLVSGVPD RFSGSGSGTD FTLKISRVEA  240
EDVGVYYCAQ NLELPYTFGG GTKVEIKRTV ESKYGPPCPP CPAPEFLGGP SVFLFPPKPK  300
DTLMISRTPE VTCVVVDVSQ EDPEVQFNWY VDGVEVHNAK TKPREEQFNS TYRVVSVLTV  360
LHQDWLNGKE YKCKVSNKGL PSSIEKTISK AKGQPREPQV YTLPPSQEEM TKNQVSLTCL  420
VKGFYPSDIA VEWESNGQPE NNYKTTPPVL DSDGSFFLYS RLTVDKSRWQ EGNVFSCSVM  480
HEALHNHYTQ KSLSLSLGKI YIWAPLAGTC GVLLLSLVIT LYCKRGRKKL LYIFKQPFMR  540
PVQTTQEEDG CSCRFPEEEE GGCELRVKFS RSADAPAYKQ GQNQLYNELN LGRREEYDVL  600
DKRRGRDPEM GGKPRRKNPQ EGLYNELQKD KMAEAYSEIG MKGERRRGKG HDGLYQGLST  660
ATKDTYDALH MQALPPR                                                677

SEQ ID NO: 34         moltype = AA  length = 672
FEATURE               Location/Qualifiers
REGION                1..672
                      note = synthesized
REGION                1..672
                      note = misc_feature - Chimeric antigen receptor
source                1..672
                      mol_type = protein
                      organism = synthetic construct
SEQUENCE: 34
MALPVTALLL PLALLLHAAR PEVQLVESGG GLVQPGRSLR LSCAASGFTF NDYAMHWVRQ  60
```

```
APGKGLEWVS TISWNSGSIG YADSVKGRFT ISRDNAKKSL YLQMNSLRAE DTALYYCAKD  120
IQYGNYYYGM DVWGQGTTVT VSSGGGGSGG GGSGGGGSEI VLTQSPATLS LSPGERATLS  180
CRASQSVSSY LAWYQQKPGQ APRLLIYDAS NRATGIPARF SGSGSGTDFT LTISSLEPED  240
FAVYYCQQRS NWPITFGQGT RLEIKESKYG PPCPPCPAPE FLGGPSVFLF PPKPKDTLMI  300
SRTPEVTCVV VDVSQEDPEV QFNWYVDGVE VHNAKTKPRE EQFNSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKIYIWAP LAGTCGVLLL SLVITLYCKR GRKKLLYIFK QPFMRPVQTT  540
QEEDGCSCRF PEEEEGGCEL RVKFSRSADA PAYKQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                     672

SEQ ID NO: 35          moltype = AA  length = 653
FEATURE                Location/Qualifiers
REGION                 1..653
                       note = synthesized
REGION                 1..653
                       note = misc_feature - Chimeric antigen receptor
source                 1..653
                       mol_type = protein
                       organism = synthetic construct
SEQUENCE: 35
MALPVTALLL PLALLLHAAR PGDVMGVDSG GGLVQPGGSR KLSCAAPGFT FSSFGMHWVR  60
QAPEKGLEWV AYISSPSSTL HYADRVKGRF TISRDNPKNT LFLQMKLPSL CYGLLGPRDH  120
VHRLLKGGGG SGGGGSGGGG SDIQLTQSPA ILSASPGEKV TMTCRASSSL SFMHWYQQKP  180
GSSPKPWIYA TSNLASGVPA RFSGSGSGTS YSLTISTVEA EDAASYFCHQ WSSNPLTFGA  240
GTKLEIESKY GPPCPPCPAP EFLGGPSVFL FPPKPKDTLM ISRTPEVTCV VVDVSQEDPE  300
VQFNWYVDGV EVHNAKTKPR EEQFNSTYRV VSVLTVLHQD WLNGKEYKCK VSNKGLPSSI  360
EKTISKAKGQ PREPQVYTLP PSQEEMTKNQ VSLTCLVKGF YPSDIAVEWE SNGQPENNYK  420
TTPPVLDSDG SFFLYSRLTV DKSRWQEGNV FSCSVMHEAL HNHYTQKSLS LSLGKIYIWA  480
PLAGTCGVLL LSLVITLYCK RGRKKLLYIF KQPFMRPVQT TQEEDGCSCR FPEEEEGGCE  540
LRVKFSRSAD APAYKQGQNQ LYNELNLGRR EEYDVLDKRR GRDPEMGGKP RRKNPQEGLY  600
NELQKDKMAE AYSEIGMKGE RRRGKGHDGL YQGLSTATKD TYDALHMQAL PPR         653

SEQ ID NO: 36          moltype = AA  length = 670
FEATURE                Location/Qualifiers
REGION                 1..670
                       note = synthesized
REGION                 1..670
                       note = misc_feature - Chimeric antigen receptor
source                 1..670
                       mol_type = protein
                       organism = synthetic construct
SEQUENCE: 36
MALPVTALLL PLALLLHAAR PQVQLQQPGA ELVKPGASVK MSCKASGYTF TSYNMHWVKQ  60
TPGRGLEWIG AIYPGNGDTS YNQKFKGKAT LTADKSSSTA YMQLSSLTSE DSAVYYCARS  120
TYYGGDWYFN VWGAGTTVTV SAGGGGSGGG GSGGGGSQIV LSQSPAILSA SPGEKVTMTC  180
RASSSVSYIH WFQQKPGSSP KPWIYATSNL ASGVPVRFSG SGSGTSYSLT ISRVEAEDAA  240
TYYCQQWTSN PPTFGGGTKL EIKESKYGPP CPPCPAPEFL GGPSVFLFPP KPKDTLMISR  300
TPEVTCVVVD VSQEDPEVQF NWYVDGVEVH NAKTKPREEQ FNSTYRVVSV LTVLHQDWLN  360
GKEYKCKVSN KGLPSSIEKT ISKAKGQPRE PQVYTLPPSQ EEMTKNQVSL TCLVKGFYPS  420
DIAVEWESNG QPENNYKTTP PVLDSDGSFF LYSRLTVDKS RWQEGNVFSC SVMHEALHNH  480
YTQKSLSLSL GKIYIWAPLA GTCGVLLLSL VITLYCKRGR KKLLYIFKQP FMRPVQTTQE  540
EDGCSCRFPE EEEGGCELRV KFSRSADAPA YKQGQNQLYN ELNLGRREEY DVLDKRRGRD  600
PEMGGKPRRK NPQEGLYNEL QKDKMAEAYS EIGMKGERRR GKGHDGLYQG LSTATKDTYD  660
ALHMQALPPR                                                        670

SEQ ID NO: 37          moltype = AA  length = 715
FEATURE                Location/Qualifiers
REGION                 1..715
                       note = synthesized
REGION                 1..715
                       note = misc_feature - Chimeric antigen receptor
source                 1..715
                       mol_type = protein
                       organism = synthetic construct
SEQUENCE: 37
MALPVTALLL PLALLLHAAR PEVQLQQSGA ELVKPGASVK MSCKASGYTF TSYNMHWVKQ  60
TPGQGLEWIG AIYPGNGDTS YNQKFKGKAT LTADKSSSTA YMQLSSLTSE DSADYYCARS  120
NYYGSSYWFF DVWGAGTTVT VSSGGGGSGG GGSGGGGSDI VLTQSPAILS ASPGEKVTMT  180
CRASSSVNYM DWYQKKPGSS PKPWIYATSN LASGVPARFS GSGSGTSYSL TISRVEAEDA  240
ATYYCQQWSF NPPTFGGGTK LEIKESKYGP PCPPCPAPEF EGGPSVFLFP PKPKDTLMIS  300
RTPEVTCVVV DVSQEDPEVQ FNWYVDGVEV HNAKTKPREE QFQSTYRVVS VLTVLHQDWL  360
NGKEYKCKVS NKGLPSSIEK TISKAKGQPR EPQVYTLPPS QEEMTKNQVS LTCLVKGFYP  420
SDIAVEWESN GQPENNYKTT PPVLDSDGSF FLYSRLTVDK SRWQEGNVFS CSVMHEALHN  480
HYTQKSLSLS LGKFWVLVVV GGVLACYSLL VTVAFIIFWV RSKRSRLLHS DYMNMTPRRP  540
```

-continued

```
GPTRKHYQPY APPRDFAAYR SKRGRKKLLY IFKQPFMRPV QTTQEEDGCS CRFPEEEEGG  600
CELRVKFSRS ADAPAYKQGQ NQLYNELNLG RREEYDVLDK RRGRDPEMGG KPRRKNPQEG  660
LYNELQKDKM AEAYSEIGMK GERRRGKGHD GLYQGLSTAT KDTYDALHMQ ALPPR       715

SEQ ID NO: 38          moltype = AA  length = 660
FEATURE                Location/Qualifiers
REGION                 1..660
                       note = synthesized
REGION                 1..660
                       note = misc_feature - Chimeric antigen receptor
source                 1..660
                       mol_type = protein
                       organism = synthetic construct
SEQUENCE: 38
MALPVTALLL PLALLLHAAR PEVQLQQSGA ELVKPGASVK MSCKASGYTF TSYNMHWVKQ  60
TPGQGLEWIG AIYPGNGDTS YNQKFKGKAT LTADKSSSTA YMQLSSLTSE DSADYYCARS  120
NYYGSSYWFF DVWGAGTTVT VSSGGGGSGG GGSGGGGSDI VLTQSPAILS ASPGEKVTMT  180
CRASSSVNYM DWYQKKPGSS PKPWIYATSN LASGVPARFS GSGSGTSYSL TISRVEAEDA  240
ATYYCQQWSF NPPTFGGGTK LEIKESKYGP PCPPCPAPEF EGGPSVFLFP PKPKDTLMIS  300
RTPEVTCVVV DVSQEDPEVQ FNWYVDGVEV HNAKTKPREE QFQSTYRVVS VLTVLHQDWL  360
NGKEYKCKVS NKGLPSSIEK TISKAKGQPR EPQVYTLPPS QEEMTKNQVS LTCLVKGFYP  420
SDIAVEWESN GQPENNYKTT PPVLDSDGSF FLYSRLTVDK SRWQEGNVFS CSVMHEALHN  480
HYTQKSLSLS LGKIYIWAPL AGTCGVLLLS LVITLYCKRG RKKLLYIFKQ PFMRPVQTTQ  540
EEDGCSCRFP EEEEGGCELR VKFSRSADAP AYKQGQNQLY NELNLGRREE YDVLDKRRGR  600
DPEMGGKPRR KNPQEGLYNE LQKDKMAEAY SEIGMKGERR RGKGHDGLYQ GLSTATKDTY  660

SEQ ID NO: 39          moltype = AA  length = 672
FEATURE                Location/Qualifiers
REGION                 1..672
                       note = synthesized
REGION                 1..672
                       note = misc_feature - Chimeric antigen receptor
source                 1..672
                       mol_type = protein
                       organism = synthetic construct
SEQUENCE: 39
MALPVTALLL PLALLLHAAR PEVQLVESGG GLVQPGRSLR LSCAASGFTF NDYAMHWVRQ  60
APGKGLEWVS TISWNSGSIG YADSVKGRFT ISRDNAKKSL YLQMNSLRAE DTALYYCAKD  120
IQYGNYYYGM DVWGQGTTVT VSSGGGGSGG GGSGGGGSEI VLTQSPATLS LSPGERATLS  180
CRASQSVSSY LAWYQQKPGQ APRLLIYDAS NRATGIPARF SGSGSGTDFT LTISSLEPED  240
FAVYYCQQRS NWPITFGQGT RLEIKESKYG PPCPPCPAPE FEGGPSVFLF PPKPKDTLMI  300
SRTPEVTCVV VDVSQEDPEV QFNWYVDGVE VHNAKTKPRE EQFQSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKIYIWAP LAGTCGVLLL SLVITLYCKR GRKKLLYIFK QPFMRPVQTT  540
QEEDGCSCRF PEEEEGGCEL RVKFSRSADA PAYKQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                      672
```